US011168052B2

(12) United States Patent
Choi

(10) Patent No.: US 11,168,052 B2
(45) Date of Patent: Nov. 9, 2021

(54) CARBAMATE DERIVATIVE COMPOUNDS, PROCESSES FOR PREPARING THEM AND THEIR USES

(71) Applicant: BIO-PHARM SOLUTIONS CO., LTD., Gyeonggi-do (KR)

(72) Inventor: Yong Moon Choi, Seoul (KR)

(73) Assignee: BIO-PHARM SOLUTIONS CO., LTD.

( * ) Notice: Subject to any disclaimer, the term of this patent is extended or adjusted under 35 U.S.C. 154(b) by 0 days.

(21) Appl. No.: 15/526,502

(22) PCT Filed: Feb. 28, 2017

(86) PCT No.: PCT/KR2017/002236
§ 371 (c)(1),
(2) Date: May 12, 2017

(87) PCT Pub. No.: WO2017/150904
PCT Pub. Date: Sep. 8, 2017

(65) Prior Publication Data
US 2018/0057449 A1  Mar. 1, 2018

Related U.S. Application Data

(60) Provisional application No. 62/300,984, filed on Feb. 29, 2016.

(51) Int. Cl.
| C07C 271/34 | (2006.01) |
| C07C 35/32  | (2006.01) |
| C07C 43/192 | (2006.01) |
| C07F 7/18   | (2006.01) |
| C07C 35/52  | (2006.01) |

(52) U.S. Cl.
CPC ............ *C07C 271/34* (2013.01); *C07C 35/32* (2013.01); *C07C 35/52* (2013.01); *C07C 43/192* (2013.01); *C07F 7/1804* (2013.01); *C07C 2602/08* (2017.05); *C07C 2602/10* (2017.05)

(58) Field of Classification Search
CPC .............................. C07C 271/34; C07C 35/32
See application file for complete search history.

(56) References Cited

U.S. PATENT DOCUMENTS

| 2002/0115570 A1 | 8/2002 | Back et al. |
| 2008/0090903 A1 | 4/2008 | Pandey et al. |
| 2012/0184762 A1 | 7/2012 | Choi |

FOREIGN PATENT DOCUMENTS

WO    WO 98/06866    2/1998

OTHER PUBLICATIONS

Roy Johnson, Organic Reactions, 117-264 (2004). (Year: 2004).*
Adam, W. et al. Dioxirane Oxidations of Compounds Other than Alkenes, Chapter 1, Organic Reactions (2007), 69, 1-346 (Year: 2007).*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/09/24/alzheimers.drug.ap/indexhtml>.*
Dafoe et al., "Bioproduction of cis-(1S, 2R)-indandiol, a chiral pharmaceutical intermediate, using a solid-liquid two-phase partitioning bioreactor for enhanced removal of inhibitors," Journal of Chemical Technology and Biotechnology, 2011, vol. 86(11), pp. 1379-1385.
Demizu et al., "Copper complex catalyzed asymmetric monosulfonylation of meso-vic-diols," Tetrahedron Letters, 2007, vol. 48(43), pp. 7605-7609.
Guo et al., "A Metal-Free Synthesis of N-Aryl Carbamates under Ambient Conditions," Angewandte Chem., 2015, vol. 127(40), pp. 11852-11856.
International Search Report for International (PCT) Patent Application No. PCT/KR2017/002236, dated Jun. 13, 2017, 4 pages.
"Hippocampus," Wikipedia, last edited Dec. 28, 2019, 18 pages [retrieved online from: en.wikipedia.org/wiki/Hippocampus].
Hirsch et al. "Ontogenic study of lithium-pilocarpine-induced status epilepticus in rats," Brain Research, 1992, vol. 583, pp. 120-126.
Hong et al. "Neuroprotective effect of lithium after pilocarpine-induced status epilepticus in mice," The Korean Journal of Physiology & Pharmacology, 2017, vol. 21, No. 1, pp. 125-131.
Rager "The Role of Apoptosis-Associated Pathways as Responders to Contaminants and in Disease Progression," Systems Biology in Toxicology and Environmental Health, Chapter 8, 2015, pp. 187-205.
Reddy et al. "Experimental Models of Status Epilepticus and Neuronal Injury for Evaluation of Therapeutic Interventions," International Journal of Molecular Sciences, 2013, vol. 14, pp. 18284-18318.
Scharfman "Alzheimer's disease and epilepsy: insight from animal models," Future Neurology, Mar. 2012, vol. 7, No. 2, pp. 177-192.
Wang et al. "Propofol effectively inhibits lithium-pilocarpine-induced status epilepticus in rats via downregulation of N-methyl-D-aspartate receptor 2B subunit expression," Neural Regeneration Research, Apr. 2012, vol. 7, No. 11, pp. 827-832.
"RN 1089318-93-3," Chemical Abstract Service, CA, STN Registry, Dec. 24, 2008, 5 pages.
Bamberger et al. "Studien über alicyclische Naphtalinderivate," Justus Liebigs Annalen Der Chemi, 1895, vol. 288, No. 1, pp. 74-133.
Böeseken et al. "On the Hydrindene-1.2. diols," Proceedings of the Section of Sciences of the Koninklijke Nederlandsche Akademie Van Wetenschappen, Aug. 1918, vol. 2, pp. 1186-1191.

(Continued)

Primary Examiner — Shawquia Jackson
(74) Attorney, Agent, or Firm — Sheridan Ross P.C.

(57) ABSTRACT

The present invention relates to a pharmaceutical composition for treating or preventing CNS disorders containing a carbamate derivative compound and/or pharmaceutically acceptable salt thereof as an active ingredient. Furthermore, the present invention relates to a method for treatment or prevention CNS disorders comprising administering a carbamate derivative compound in a pharmaceutically effective amount to a subject in need of treatment or prevention of CNS disorders.

16 Claims, 1 Drawing Sheet

(56) References Cited

OTHER PUBLICATIONS

Bowers et al. "Stereoselective benzylic hydroxylation of 2-substituted indanes using toluene dioxygenase as a biocatalyst," Journal of the Chemical Society, Perkin Transactions 1, 1999, Issue 11, pp. 1453-1462.

Dubois et al. "Dramatic influence of the substitution of alkylidene-5H-furan-2-ones in Diels-Alder cycloadditions with o-quinonedimethide as diene partner: en route to the CDEF polycyclic ring system of lactonamycin," Organic & Biomolecular Chemistry, 2012, vol. 10, pp. 4712-4719.

Jadhav et al. "Enantioselective α-Benzoyloxylation of Ketones Promoted by Primary Amine Catalyst," The Journal of Organic Chemistry, 2012, vol. 77, pp. 2667-2674.

Lautens et al. "Rhodium-catalysed asymmetric ring opening of oxabicyclic alkenes with heteroatom nucleophiles," Journal of Organometallic Chemistry, 2001, vol. 624, pp. 259-270.

Li et al. "Poly(4-Vinylpyridinium P-Toluenesulfonate) as a Polymer-Supported Catalyst for Hydrolysis of Tetrahydropyranyl Ethers," Synthetic Communications, 1998, vol. 28, No. 17, pp. 3209-3212.

Official Action with English Translation for China Patent Application No. 201780014181.5, dated Dec. 29, 2020, 11 pages.

Extended Search Report for European Patent Application No. 17760308.1, dated Aug. 8, 2019, 13 pages.

\* cited by examiner

[Fig. 1]
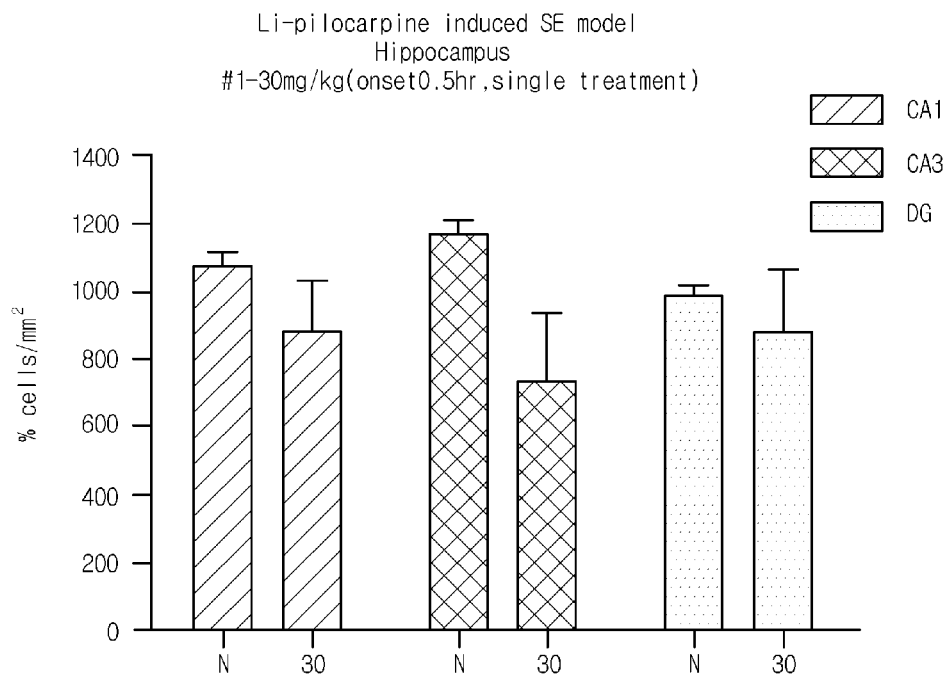
[Fig. 2]
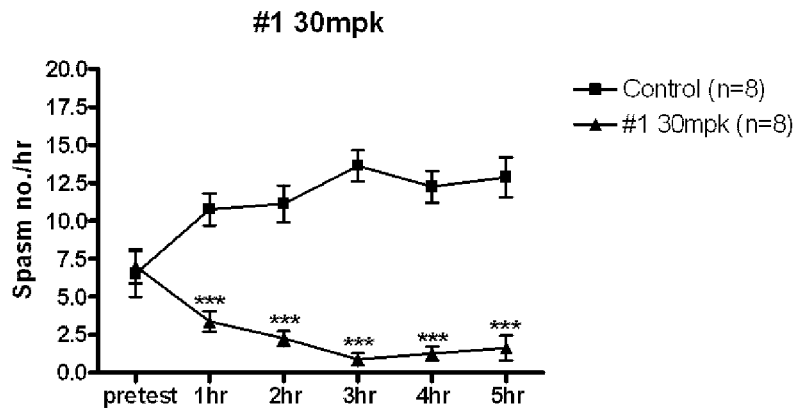

CARBAMATE DERIVATIVE COMPOUNDS, PROCESSES FOR PREPARING THEM AND THEIR USES

CROSS REFERENCE TO RELATED APPLICATIONS

This application is a national stage application under 35 U.S.C. 371 and claims the benefit of PCT Application No. PCT/KR2017/002236 having an international filing date of 28 Feb. 2017, which designated the United States, which PCT application claimed the benefit of U.S. Provisional Patent Application No. 62/300,984 filed Feb. 29, 2016, the disclosure of each of which are incorporated herein by reference.

TECHNICAL FIELD

The present invention relates to a carbamate derivative compound for treating or preventing CNS disorders and/or pain, and/or pharmaceutically acceptable salt thereof as an active ingredient. Furthermore, the present invention relates to a method for treatment or prevention of CNS disorders and/or pain comprising administering a carbamate derivative compound in a pharmaceutically effective amount to a subject in need of treatment or prevention of CNS disorders like epilepsy and/or pain.

BACKGROUND ART

Central nervous system (hereinafter referred to as "CNS") disorders nowadays concern large sections of the population. In particular on account of the increase in elderly people, the numbers of patients are increasing continuously.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a deficiency of choline, dopamine, norepinephrine and/or serotonin. Relatively common CNS disorders include or go along with pain, epilepsy or epilepsy-related syndrome, pediatric epilepsy or pediatric epilepsy-related syndrome, memory presenile dementia (early-onset Alzheimer's disease), senile dementia (dementia of the Alzheimer's type), micro-infarct dementia, AIDS-related dementia, Creutzfeld-Jakob disease, Picks disease, Parkinsonism including Parkinson's disease, Lewy body dementia, progressive supranuclear palsy, Huntington's chorea, tardive dyskinesia, hyperkinesia, mania, attention deficit disorder, anxiety, dyslexia, schizophrenia, depression, obsessive-compulsive disorders, and Tourette's syndrome.

Particularly, epilepsy is the most common CNS disorder, affecting about 1% of the population worldwide. Epilepsy describes a condition in which a person has recurrent seizures due to a chronic, underlying process. Epilepsy refers to a clinical phenomenon rather than a single disease entity, since there are many forms and causes of epilepsy. Using a definition of epilepsy as two or more unprovoked seizures, the incidence of epilepsy is estimated at 5 to 10 people per 1000. An essential step in the diagnosis and treatment of a patient with a seizure is to determine the type of seizure that has occurred. The main characteristic that distinguishes the different categories of seizure is whether the seizure activity is partial or generalized or unclassified.

For the general population there are approximately 20-70 new cases per 100,000 diagnosed each year with a 3-5% lifetime probability of developing the disease. The older established antiepileptic drugs (AEDs) phenytoin, carbamazepine, clonazepam, ethosuximide, valproic acid and barbiturates are widely prescribed but suffer from a range of side effects. Furthermore, there is a significant group of patients (20-30%) that are resistant to the currently available therapeutic agents. Since 1989 several new drugs have been launched, including felbamate, gabapentin, lamotrigine, oxcarbazepine, tiagabine, topiramate, vigabartrin, zonisamide and levetiracetam. While many of new AEDs show improved efficacies and side-effect profiles, about 30% of patients with epilepsy remain untreated. There is clearly a need for improved medication.

Pain is one of the most common reasons for a patient to seek medical care and in consequence, pain results in a tremendous number of lost work days per year.

Pain is an unpleasant feeling often caused by intense or damaging stimuli, such as stubbing a toe, burning a finger, putting alcohol on a cut, and bumping the funny bone. The International Association for the Study of Pain's widely used definition states: "Pain is an unpleasant sensory and emotional experience associated with actual or potential tissue damage, or described in terms of such damage". Pain motivates the individual to withdraw from damaging situations, to protect a damaged body part while it heals, and to avoid similar experiences in the future. Most pain resolves promptly once the painful stimulus is removed and the body has healed, but sometimes pain persists despite removal of the stimulus and apparent healing of the body; and sometimes pain arises in the absence of any detectable stimulus, damage or disease.

Pain is the most common reason for physician consultation. It is a major symptom in many medical conditions, and can significantly interfere with a person's quality of life and general functioning. Psychological factors such as social support, hypnotic suggestion, excitement, or distraction can significantly modulate pain's intensity or unpleasantness.

In 1994, responding to the need for a more useful system for describing chronic pain, the International Association for the Study of Pain (.IASP) classified pain according to specific characteristics: (1) region of the body involved (e.g., abdomen, lower limbs), (2) system whose dysfunction may be causing the pain (e.g., nervous, gastrointestinal), (3) duration and pattern of occurrence, (4) intensity and time since onset, and (5) etiology.

This system has been criticized by Clifford J. Woolf and others as inadequate for guiding research and treatment. According to Woolf, there are three classes of pain: nociceptive pain (see hereunder), inflammatory pain which is associated with tissue damage and the infiltration of immune cells, and pathological pain which is a disease state caused by damage to the nervous system or by its abnormal function (dysfunctional pain, irritable bowel syndrome, tension type headache, etc.).

In nociceptive pain, the stimulation of the sensory nerve endings called nociceptors causes the sensation of pain. Such pain often occurs after injury or surgery. The pain signals are transmitted by the nociceptors to the brain. Often the pain is localised, constant and has an aching or throbbing quality. Once the damage to the tissue heals the pain usually resolves. Treatment with opioids may resolve nociceptive pain. Psychogenic pain is a pain disorder that is associated with psychological factors. Some types of mental or emotional problems can cause pain. They can also increase or prolong pain. Stomach pain is one of the most common types of psychogenic pain. People with this pain disorder actually have real pain. The diagnosis is made when all physical causes of pain are ruled out.

Neuropathic pain is caused by abnormalities in the nerves, spinal cord or brain and is a chronic type of non-malignant pain with an estimated prevalence of over 1% of the population. Optimizing pain relief in these patients is crucial in helping a patient regain control of his or her life. The most common cause of neuropathic pain is injury or dysfunction of nerves. Injury or dysfunction of peripheral nerves or nerves descending from the spinal cord results in disinhibition of nerve impulses at the spinal cord which in consequence results in pain. Neuropathic pain can also be centrally mediated, rather than peripheral, in conditions such as spinal cord injury and multiple sclerosis.

Neuropathic pain can therefore be divided into two further classes; peripheral neuropathic pain and central neuropathic pain depending on whether the peripheral or central nervous system is affected.

Inadequate treatment of pain is widespread throughout surgical wards, intensive care units, accident and emergency departments, in general practice, in the management of all forms of chronic pain and in end of life care. This neglect is extended to all ages, from neonates to the frail elderly. African and Hispanic Americans are more likely than others to suffer needlessly in the hands of a physician; and women's pain is more likely to be undertreated than men's. Therefore, it is needed to develop therapeutic measures for treating or alleviating pain.

DISCLOSURE OF INVENTION

Technical Problem

The present inventor has done intensive studies to develop a novel drug with excellent activity and low toxicity which may be an effective treatment for CNS disorders and/or pain. As a result, the present inventors have discovered that the carbamate derivatives represented by the below Chemical formula I provide highly enhanced anti-epileptic activity with significantly decreased side effects.

The present inventor has done intensive studies to develop a novel drug with excellent activity and low toxicity which may be an effective treatment for CNS disorders and/or pain. As a result, the present inventors have discovered that the carbamate derivatives represented by the below Chemical formula I provide highly enhanced anti-epileptic activity with significantly decreased side effects.

Accordingly, it is an object of this invention is to provide a novel compound represented by the following formula 1 or pharmaceutically acceptable salt thereof.

Another object of this invention is to provide a novel pharmaceutical composition for treating or preventing CNS disorders and/or pain containing a carbamate derivative compound and/or pharmaceutically acceptable salt thereof as an active ingredient.

Another object of this invention is to provide a method for treatment or prevention of CNS disorders and/or pain comprising administering a carbamate derivative compound in a pharmaceutically effective amount to a subject in need of treatment or prevention of CNS disorders and/or pain.

Solution to Problem

As used herein, the below terms have the following meanings unless specified otherwise:
Definitions It is noted here that as used in this specification and the appended claims, the singular forms "a," "an," and "the" include plural reference unless the context clearly dictates otherwise.

"Alkyl," by itself or as part of another substituent, means, unless specified otherwise, a straight or branched chain, fully saturated aliphatic hydrocarbon radical having the number of carbon atoms designated. For example, "$C_1$-$C_{10}$alkyl" refers to a hydrocarbon radical straight or branched, containing from 1 to 10 carbon atoms that is derived by the removal of one hydrogen atom from a single carbon atom of a parent alkane. In the context of the invention, unless specified otherwise, the term "alkyl" means "$C_1$-$C_{10}$alkyl", preferably "$C_1$-$C_5$alkyl."

"Alkenyl" by itself or as part of another substituent refers to a straight or branched chain, which may be mono- or polyunsaturated, having the number of carbon atoms designated. For example, "$C_2$-$C_8$alkenyl" means an alkenyl radical having 2, 3, 4, 5, 6, 7 or 8 atoms that is derived by the removal of one hydrogen atom from a single carbon atom of a parent alkane. In the context of the invention, unless specified otherwise, the term "alkenyl" means "$C_2$-$C_{10}$alkenyl," preferably "$C_2$-$C_5$alkenyl."

"Alkynyl", by itself or as part of another substituent, means a straight or branched chain hydrocarbon radical, which may be mono- or polyunsaturated, having the number of carbon atoms designated. For example, "$C_2$-$C_8$alkynyl" means an alkynyl radical having from 2 to 8 carbon atoms that is derived by the removal of one hydrogen atom from a single carbon atom of a parent alkane. In the context of the invention, unless specified otherwise, the term "alkynyl" means "$C_2$-$C_{10}$alkynyl," preferably "$C_2$-$C_5$alkynyl."

"Cycloalkyl" by itself or as part of another substituent, represent, unless otherwise stated, cyclic versions of "alkyl", "alkenyl" and "alkynyl" in which all ring atoms are carbon. "Cycloalkyl" or "carbocycle" refers to a mono- or polycyclic group. When used in connection with cycloalkyl substituents, the term "polycyclic" refers herein to fused and non-fused alkyl cyclic structures. "Cycloalkyl" or "carbocycle" may form a bridged ring or a spiro ring. The cycloalkyl group may have one or more double or triple bond(s). The term "cycloalkenyl" refers to a cycloalkyl group that has at least one site of alkenyl unsaturation between the ring vertices. The term "cycloalkynyl" refers to a cycloalkyl group that has at least one site of alkynyl unsaturation between the ring vertices. When "cycloalkyl" is used in combination with "alkyl", as in $C_{3-8}$cycloalkyl$C_{3-8}$alkylene-, the cycloalkyl portion is meant to have the stated number of carbon atoms (e.g., from three to eight carbon atoms), while the alkylene portion has from one to eight carbon atoms. Typical cycloalkyl substituents have from 3 to 8 ring atoms. Examples of cycloalkyl include cyclopentyl, cyclohexyl, 1-cyclohexenyl, 3-cyclohexenyl, cycloheptyl, and the like.

"Heterocycle", "heterocyclyl" or "heterocyclic" refers to a saturated or unsaturated non-aromatic cyclic group containing at least one heteroatom. As used herein, the term "heteroatom" is meant to include oxygen (O), nitrogen (N), sulfur (S) and silicon (Si). Each heterocycle can be attached at any available ring carbon or heteroatom. Each heterocycle may have one or more rings. Each heterocycle typically contains independently selected 1, 2, 3, 4 or 5 heteroatoms. Preferably, these groups contain 1, 2, 3, 4, 5, 6, 7, 8, 9 or 10 carbon atoms, 0, 1, 2, 3, 4 or 5 nitrogen atoms, 0, 1 or 2 sulfur atoms and 0, 1 or 2 oxygen atoms. More preferably, these groups contain 1, 2 or 3 nitrogen atoms, 0-1 sulfur atoms and 0-1 oxygen atoms. Non-limiting examples of heterocycle groups include morpholin-3-one, piperazine-2-one, piperazin-1-oxide, pyridine-2-one, piperidine, morpholine, piperazine, isoxazoline, pyrazoline, imidazoline, pyrazol-5-one, pyrrolidine-2,5-dione, imidazolidine-2,4-dione, pyrrolidine, tetrahydrofuran, tetrahydroquinolinyl, decahydroquinolinyl, tetrahydrobenzoox-azepinyl dihydrodibenzo-oxepin and the like.

"Aryl" by itself or as part of another substituent refers to a polyunsaturated, aromatic, hydrocarbon group containing from 6 to 14 carbon atoms, which can be a single ring or multiple rings (up to three rings) which are fused together or linked covalently. Thus the phrase includes, but is not limited to, groups such as phenyl, biphenyl, anthracenyl, naphthyl by way of example. Non-limiting examples of unsubstituted aryl groups include phenyl, 1-naphthyl, 2-naphthyl and 4-biphenyl. In the context of the invention, unless specified otherwise, the term "aryl" means "$C_6$-$C_{12}$aryl," preferably "$C_6$-$C_{10}$aryl."

"Arylalkyl" or "aralkyl" refers to a monovalent alkyl group substituted with aryl. An example of arylalkyl includes, but is not limited to, benzyl. In certain embodiments, both alkyl and aryl may be optionally substituted with one or more substituents as described herein elsewhere. Example of arylalkyl is benzyl.

"Heteroaryl" refers to a cyclic or polycyclic aromatic radical that contains from one to five heteroatoms selected from N, O, and S, wherein the nitrogen and sulfur atoms are optionally oxidized, and the nitrogen atom(s) are optionally quaternized. In the context of the invention, unless specified otherwise, the term "heteroaryl" means "$C_1$-$C_{10}$heteroaryl," preferably "$C_1$-$C_8$heteroaryl." Non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl and 4-pyrimidyl. If not specifically stated, substituents for each of the above noted aryl and heteroaryl ring systems are selected from the group of acceptable substituents described herein.

"Alkoxy" refers to —$OR_d$ wherein $R_d$ is alkyl as defined herein. Representative examples of alkoxy groups include methoxy, ethoxy, t-butoxy, trifluoromethoxy, and the like. In the context of the invention, unless specified otherwise, the term "alkoxy" means "$C_1$-$C_{10}$alkoxy," preferably "$C_1$-$C_5$ alkoxy."

"Alkoxyalkyl" refers to a monovalent alkyl group substituted with alkoxy. For example, "$C_1$-$C_5$alkoxy$C_1$-$C_5$alkyl" means an alkyl radical having from 1 to 5 carbon atoms that is derived by the substitution of one hydrogen atom with $C_1$-$C_5$alkoxy. An example of alkoxyalkyl includes, but is not limited to, methoxymethyl, ethoxymethyl, ethoxyethyl and 2-methoxyethyl. Particularly preferred is methoxymethyl.

"Aryloxyalkyl" or "arylalkyloxyalkyl" refers to a monovalent alkyl group substituted with aryloxy or arylalkyloxy. For example, "$C_6$-$C_{10}$arylalkyloxy$C_1$-$C_5$alkyl" means an alkyl radical having from 1 to 5 carbon atoms that is derived by the substitution of one hydrogen atom with $C_6$-$C_{10}$arylalkyloxy. An example of arylalkyloxyalkyl includes, but is not limited to benzyloxymethyl.

"Alkoxyalkoxyalkyl" refers to a divalent alkyl group substituted with alkoxy groups. For example, "$C_1$-$C_5$alkoxy ($C_1$-$C_5$alkoxy)$C_1$-$C_5$alkyl" means an alkyl radical having from 1 to 5 carbon atoms that is derived by the substitutions of two hydrogen atom with $C_1$-$C_5$alkoxy groups respectively. An example of alkoxyalkoxyalky includes, but is not limited to methoxyethoxymethyl.

"Acyl" refers to the group —C(=O)$R^C$ wherein $R^c$ is alkyl, alkenyl, alkynyl, cycloalkyl, cycloalkenyl, aryl, heteroaryl or heterocyclyl. Acyl includes the "acetyl" group —C(=O)CH$_3$. "Acylamino-" refers to the group —NR$^a$C(=O)$R^c$ wherein $R^c$ is alkyl, alkenyl, alkynyl, cycloalkyl, cycloalkenyl, aryl, heteroaryl or heterocyclyl.

"Amino" refers to a monovalent radical —NR$^a$R$^b$ or divalent radical —NR$^a$—. The term "alkylamino" refers to the group —NR$^a$R$^b$ wherein R$^a$ is alkyl and R$^b$ is H or alkyl.

"Alkylamino-" refers to the group —NR$^a$R$^b$ wherein R$^c$ is alkyl, alkenyl or alkynyl.

"Alkylsulfanyl", "alkylthio", or "thioalkoxy" refers to the group S—R$^d$, wherein R$^d$ is alkyl.

"Carbonyl" refers to the divalent group —C(=O)—.

"Carboxy" or "carboxyl" refers to the group —CO$_2$H.

"Carboxyl ester" or "carboxy ester" refers to the groups —C(=O)OR$^C$ wherein R$^c$ is alkyl, alkenyl, alkynyl, cycloalkyl, cycloalkenyl, aryl, heteroaryl or heterocyclyl.

"Alkoxycarbonyl" refers to —C(=O)OR$^d$ wherein R$^d$ is alkyl.

Each of the terms herein (e.g., "alkyl," "heteroalkyl," "aryl" and "heteroaryl") is meant to include both "unsubstituted" and optionally "substituted" forms of the indicated radical, unless otherwise indicated. Typically each radical is substituted with 0, 1, 2 3 4 or 5 substituents, unless otherwise indicated. Examples of substituents for each type of radical are provided below.

"Substituted" refers to a group as defined herein in which one or more bonds to a carbon(s) or hydrogen(s) are replaced by a bond to non-hydrogen and non-carbon atom "substituents" such as, but not limited to, a halogen atom such as F, Cl, Br, and I; an oxygen atom in groups such as hydroxyl groups, alkoxy groups, aryloxy, and acyloxy groups; a sulfur atom in groups such as thiol groups, alkyl and aryl sulfide groups, sulfone groups, sulfonyl groups, and sulfoxide groups; a nitrogen atom in groups such as amino, alkylamines, dialkylamines, arylamines, alkylarylamines, diarylamines, alkoxyamino, hydroxyamino, acylamino, sulfonylamino, N-oxides, imides, and enamines; and other heteroatoms in various other groups. "Substituents" also include groups in which one or more bonds to a carbon(s) or hydrogen(s) atom is replaced by a higher-order bond (e.g., a double- or triple-bond) to a heteroatom such as oxygen in oxo, acyl, amido, alkoxycarbonyl, aminocarbonyl, carboxyl, and ester groups; nitrogen in groups such as imines, oximes, hydrazones, and nitriles. "Substituents" further include groups in which one or more bonds to a carbon(s) or hydrogen(s) atoms is replaced by a bond to a cycloalkyl, heterocyclyl, aryl, and heteroaryl groups. Representative "substituents" include, among others, groups in which one or more bonds to a carbon or hydrogen atom is/are replaced by one or more bonds to fluoro, chloro, or bromo group. Another representative "substituent" is the trifluoromethyl group and other groups that contain the trifluoromethyl group. Other representative "substituents" include those in which one or more bonds to a carbon or hydrogen atom is replaced by a bond to an oxygen atom such that the substituted alkyl group contains a hydroxyl, alkoxy, or aryloxy group. Other representative "substituents" include alkyl groups that have an amine, or a substituted or unsubstituted alkylamine, dialkylamine, arylamine, (alkyl) (aryl) amine, diarylamine, heterocyclylamine, diheterocyclylamine, (alkyl) (heterocyclyl) amine, or (aryl) (heterocyclyl) amine group. Still other representative "substituents" include those in which one or more bonds to a carbon(s) or hydrogen(s) atoms is replaced by a bond to an alkyl, cycloalkyl, aryl, heteroaryl, or heterocyclyl group. The herein-defined groups may include prefixes and/or suffixes that are commonly used in the art to create additional well-recognized substituent groups.

In one aspect of this invention, there is provided a compound represented by the following formula 1 or pharmaceutically acceptable salt thereof:

[Chemical formula 1]

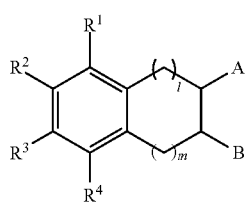

Wherein,
$R^1$, $R^2$, $R^3$ and $R^4$ are each independently selected from the group consisting of hydrogen and halogen;
A and B are each independently selected from the group consisting of

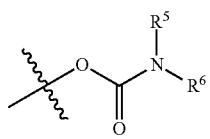

and —$OR^7$;
$R^5$ and $R^6$ are each independently selected from the group consisting of hydrogen, $C_1$-$C_{10}$alkyl, $C_3$-$C_8$cycloalkyl and $C_6$-$C_{10}$aryl; $R^7$ is selected from hydrogen, $C_1$-$C_{10}$alkyl, $C_1$-$C_5$alkoxyC$_1$-$C_5$alkyl, $C_6$-$C_{10}$arylalkyloxyC$_1$-$C_5$alkyl, $C_1$-$C_5$alkoxy($C_1$-$C_5$alkoxy)C$_1$-$C_5$alkyl, $C_3$-$C_5$heterocyclyl, $C_1$-$C_5$alkylthioC$_1$-$C_5$alkyl; trialkyl silyl groups and trialkylaryl silyl groups (in trialkyl silyl groups and trialkylaryl silyl groups, each alkyl group is independently selected from the group consisting of linear, branched, or cyclic a $C_1$-$C_5$alkyl groups and each aryl group is independently selected from the group consisting of $C_6$-$C_{10}$aryl groups); and l and m are each independently selected from an integer from 0 to 4.

In one embodiment of the present invention, $R^1$, $R^2$, $R^3$ and $R^4$ are each independently selected from the group consisting of hydrogen, F, Br, Cl and I; however, if $R^1$, $R^2$, $R^3$ and $R^4$ are hydrogen, l+m is not 1. For example, when $R^1$, $R^2$, $R^3$ and $R^4$ are all the same as hydrogen, the cycloalkyl ring attached to the benzene ring in the Chemical formula 1 may be a 4, 6, 7 or 8 membered cycloalkyl ring. If at least one hydrogen of $R^1$, $R^2$, $R^3$ and $R^4$ is replaced with halogen, the cycloalkyl ring attached to the benzene ring may be a 4-8 membered ring.

In one embodiment of the present invention, in Chemical Formula 1, A and B can be the same or different from each other and at least one of A and B is

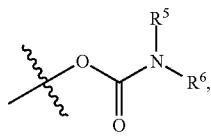

and $R^5$ and $R^6$ are the same as defined as above.

In one particular embodiment of the present invention, in Chemical Formula 1, $R^5$ and $R^6$ are each independently selected from the group consisting of hydrogen, $C_1$-$C_{10}$alkyl, $C_3$-$C_8$cycloalkyl and $C_6$-$C_{10}$aryl; preferably $R^5$ and $R^6$ may be hydrogen, hydrogen, methyl, ethyl, propyl, iso-propyl, t-butyl, cyclopropyl, cyclohexyl, bicycloheptanyl, phenyl and benzyl.

In one particular embodiment of the present invention, in Chemical Formula 1, $R^7$ are selected from hydrogen, $C_1$-$C_{10}$alkyl, $C_1$-$C_5$alkoxyC$_1$-$C_5$alkyl, $C_6$-$C_{10}$aryloxyC$_1$-$C_5$alkyl, $C_1$-$C_5$alkoxy($C_1$-$C_5$alkoxy)C$_1$-$C_5$alkyl, $C_3$-$C_5$heterocyclyl, $C_1$-$C_5$alkylthioC$_1$-$C_5$alkyl, trialkyl silyl groups and trialkylaryl silyl groups. For example, $R^7$ may be hydrogen, trimethyl silyl, triethyl silyl, triisopropyl silyl, t-butyl dimethyl silyl, trimethylsilylethoxymethyl (SEM), methoxymethyl (MOM), methoxyethoxymethyl (MEM), ethoxyethyl (EE), therahydropyranyl (THP) methylthiomethyl (MTM) and benzyloxymethyl (BOM). When $R^7$ is trialkyl silyl groups or trialkylaryl silyl groups, each alkyl group may be independently selected from the group consisting of linear, branched, or cyclic a $C_1$-$C_5$alkyl groups and each aryl group may be independently selected from the group consisting of $C_6$-$C_{10}$aryl groups. For example, $R^7$ may be selected from hydrogen, trimethyl silyl, triethyl silyl, triisopropyl silyl, and t-butyl dimethyl silyl.

In one particular embodiment of the present invention, in Chemical Formula 1, A and B may be independently selected from the group consisting of

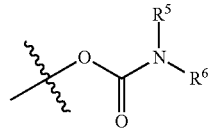

and —$OR^7$; wherein $R^5$ and $R^6$ are each independently selected from the group consisting of hydrogen, methyl, ethyl, propyl, iso-propyl and t-butyl; and $R^7$ is selected from hydrogen, methyl, ethyl, propyl, iso-propyl, t-butyl and methoxymethyl (MOM) and l and m are independently an integer from 0 to 2.

In a preferred embodiment of the present invention, in Chemical Formula 1, at least one of A and B is

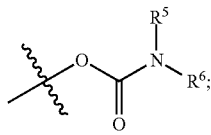

when l is an integer 0, m is an integer from 1 or 2; or when m is an integer 0, l is an integer from 1 or 2.

In one embodiment of the present invention, the compound of Chemical Formula 1 may be selected from the group consisting of:

(1) (1S, 2R)-8-chloro-1-hydroxy-1,2,3,4-tetrahydronaphthalen-2-yl carbamate
(2) (1R, 2S)-8-chloro-1-hydroxy-1,2,3,4-tetrahydronaphthalen-2-yl carbamate
(3) racemate of (1S, 2R)-8-chloro-1-hydroxy-1,2,3,4-tetrahydronaphthalen-2-yl carbamate and (1R, 2S)-8-chloro-1-hydroxy-1,2,3,4-tetrahydronaphthalen-2-yl carbamate
(4) (1R, 2R)-8-chloro-1-hydroxy-1,2,3,4-tetrahydronaphthalen-2-yl carbamate
(5) (1S, 2S)-8-chloro-1-hydroxy-1,2,3,4-tetrahydronaphthalen-2-yl carbamate
(6) (1S, 2R)-7-chloro-1-hydroxy-1,2,3,4-tetrahydronaphthalen-2-yl carbamate
(7) (1R, R)-7-chloro-1-hydroxy-1,2,3,4-tetrahydronaphthalen-2-yl carbamate
(8) (1S, 2R)-6-chloro-1-hydroxy-1,2,3,4-tetrahydronaphthalen-2-yl carbamate
(9) (1R, 2S)-6-chloro-1-hydroxy-1,2,3,4-tetrahydronaphthalen-2-yl carbamate
(10) (1S, 2R)-8-fluoro-1-hydroxy-1,2,3,4-tetrahydronaphthalen-2-yl carbamate
(11) (1R, 2S)-8-fluoro-1-hydroxy-1,2,3,4-tetrahydronaphthalen-2-yl carbamate
(12) (1S, 2R)-1-hydroxy-8-iodo-1,2,3,4-tetrahydronaphthalen-2-yl carbamate
(13) (1R, 2S)-1-hydroxy-8-iodo-1,2,3,4-tetrahydronaphthalen-2-yl carbamate
(14) (1S, 2R)-1-hydroxy-1,2,3,4-tetrahydronaphthalen-2-yl carbamate
(15) (1R, 2S)-1-hydroxy-1,2,3,4-tetrahydronaphthalen-2-yl carbamate
(16) (1S, 2R)-2-hydroxy-1,2,3,4-tetrahydronaphthalen-1-yl carbamate
(17) (1R, 2S)-2-hydroxy-1,2,3,4-tetrahydronaphthalen-1-yl carbamate
(18) (1S, 2R)-8-chloro-2-hydroxy-1,2,3,4-tetrahydronaphthalen-1-yl carbamate
(19) (1R, 2S)-8-chloro-2-hydroxy-1,2,3,4-tetrahydronaphthalen-1-yl carbamate
(20) racemate of (1S, 2R)-8-chloro-2-hydroxy-1,2,3,4-tetrahydronaphthalen-1-yl carbamate and (1R, 2S)-8-chloro-2-hydroxy-1,2,3,4-tetrahydronaphthalen-1-yl carbamate
(21) (1S, 2R)-7-chloro-2-hydroxy-1,2,3,4-tetrahydronaphthalen-1-yl carbamate
(22) (1R, 2S)-7-chloro-2-hydroxy-1,2,3,4-tetrahydronaphthalen-1-yl carbamate
(23) (1S, 2R)-6-chloro-2-hydroxy-1,2,3,4-tetrahydronaphthalen-1-yl carbamate
(24) (1R, 2S)-6-chloro-2-hydroxy-1,2,3,4-tetrahydronaphthalen-1-yl carbamate
(25) (1S, 2R)-8-fluoro-2-hydroxy-1,2,3,4-tetrahydronaphthalen-1-yl carbamate
(26) (1R, 2S)-8-fluoro-2-hydroxy-1,2,3,4-tetrahydronaphthalen-1-yl carbamate
(27) (1S, 2R)-2-hydroxy-8-iodo-1,2,3,4-tetrahydronaphthalen-1-yl carbamate
(28) (1R, 2S)-2-hydroxy-8-iodo-1,2,3,4-tetrahydronaphthalen-1-yl carbamate
(29) (1S, 2R)-8-chloro-1,2,3,4-tetrahydronaphthalen-1,2-diyl dicarbamate
(30) (1R, 2S)-8-chloro-1,2,3,4-tetrahydronaphthalen-1,2-diyl dicarbamate
(31) (1R, 2R)-8-chloro-1,2,3,4-tetrahydronaphthalen-1,2-diyl dicarbamate
(32) (1S, 2R)-7-chloro-1,2,3,4-tetrahydronaphthalen-1,2-diyl dicarbamate
(33) (1R, 2S)-6-chloro-1,2,3,4-tetrahydronaphthalen-1,2-diyl dicarbamate
(34) (1S, 2R)-8-fluoro-1,2,3,4-tetrahydronaphthalen-1,2-diyl dicarbamate
(35) (1R, 2S)-8-fluoro-1,2,3,4-tetrahydronaphthalen-1,2-diyl dicarbamate
(36) (1S, 2R)-8-iodo-1,2,3,4-tetrahydronaphthalen-1,2-diyl dicarbamate
(37) (1R, 2S)-8-iodo-1,2,3,4-tetrahydronaphthalen-1,2-diyl dicarbamate
(38) (1S, 2R)-1,2,3,4-tetrahydronaphthalen-1,2-diyl dicarbamate
(39) (1R, 2S)-1,2,3,4-tetrahydronaphthalen-1,2-diyl dicarbamate
(40) (1S, 2R)-8-chloro-1-(methoxymethoxy)-1,2,3,4-tetrahydronaphthalen-2-yl carbamate
(41) (1R, 2S)-8-chloro-1-(methoxymethoxy)-1,2,3,4-tetrahydronaphthalen-2-yl carbamate
(42) (1R, 2R)-8-chloro-1-(methoxymethoxy)-1,2,3,4-tetrahydronaphthalen-2-yl carbamate
(43) (1S, 2R)-8-fluoro-1-(methoxymethoxy)-1,2,3,4-tetrahydronaphthalen-2-yl carbamate
(44) (1R, 2S)-8-fluoro-1-(methoxymethoxy)-1,2,3,4-tetrahydronaphthalen-2-yl carbamate
(45) (1S, 2R)-8-chloro-2-(methoxymethoxy)-1,2,3,4-tetrahydronaphthalen-1-yl carbamate
(46) (1R, 2S)-8-chloro-2-(methoxymethoxy)-1,2,3,4-tetrahydronaphthalen-1-yl carbamate
(47) (1S, 2R)-8-fluoro-2-(methoxymethoxy)-1,2,3,4-tetrahydronaphthalen-1-yl carbamate
(48) (1R, 2S)-8-fluoro-2-(methoxymethoxy)-1,2,3,4-tetrahydronaphthalen-1-yl carbamate
(49) (1S, 2R)-8-iodo-2-(methoxymethoxy)-1,2,3,4-tetrahydronaphthalen-1-yl carbamate
(50) (1R, 2S)-8-iodo-2-(methoxymethoxy)-1,2,3,4-tetrahydronaphthalen-1-yl carbamate
(51) (1S, 2R)-7-chloro-1-hydroxy-2,3-dihydro-1H-inden-2-yl carbamate
(52) (1R, 2S)-7-chloro-1-hydroxy-2,3-dihydro-1H-inden-2-yl carbamate
(53) (1R, 2R)-7-chloro-1-hydroxy-2,3-dihydro-1H-inden-2-yl carbamate
(54) (1S, 2S)-7-chloro-1-hydroxy-2,3-dihydro-1H-inden-2-yl carbamate
(55) (1S, 2R)-7-fluoro-1-hydroxy-2,3-dihydro-1H-inden-2-yl carbamate
(56) (1R, 2S)-7-fluoro-1-hydroxy-2,3-dihydro-1H-inden-2-yl carbamate
(57) (1S, 2R)-6-chloro-1-hydroxy-2,3-dihydro-1H-inden-2-yl carbamate
(58) (1R, 2S)-6-chloro-1-hydroxy-2,3-dihydro-1H-inden-2-yl carbamate
(59) (1S, 2R)-5,7-dichloro-1-hydroxy-2,3-dihydro-1H-inden-2-yl carbamate
(60) (1R, 2S)-5,7-dichloro-1-hydroxy-2,3-dihydro-1H-inden-2-yl carbamate
(61) (1R, 2S)-4-chloro-2-hydroxy-2,3-dihydro-1H-inden-1-yl carbamate
(62) (1S, 2R)-4-chloro-2-hydroxy-2,3-dihydro-1H-inden-1-yl carbamate
(63) (1S, 2R)-7-chloro-2-hydroxy-2,3-dihydro-1H-inden-1-yl carbamate
(64) (1R, 2S)-7-chloro-2-hydroxy-2,3-dihydro-1H-inden-1-yl carbamate
(65) (1S, 2R)-5,7-dichloro-2-hydroxy-2,3-dihydro-1H-inden-1-yl carbamate

(66) (1R, 2S)-5,7-dichloro-2-hydroxy-2,3-dihydro-1H-inden-1-yl carbamate
(67) (1R, 2S)-4-chloro-1-hydroxy-2,3-dihydro-1H-inden-2-yl carbamate
(68) (1S, 2R)-4-chloro-1-hydroxy-2,3-dihydro-1H-inden-2-yl carbamate
(69) (1S, 2R)-7-fluoro-2-hydroxy-2,3-dihydro-1H-inden-1-yl carbamate
(70) (1R, 2S)-7-chloro-2-hydroxy-2,3-dihydro-1H-inden-1-yl carbamate
(71) (1S, 2R)-7-chloro-1-(methoxymethoxy)-2,3-dihydro-1H-inden-2-yl carbamate
(72) (1R, 2S)-7-chloro-1-(methoxymethoxy)-2,3-dihydro-1H-inden-2-yl carbamate
(73) (1S, 2R)-7-fluoro-1-(methoxymethoxy)-2,3-dihydro-1H-inden-2-yl carbamate
(74) (1R, 2S)-7-fluoro-1-(methoxymethoxy)-2,3-dihydro-1H-inden-2-yl carbamate
(75) (1S, 2R)-7-chloro-2-(methoxymethoxy)-2,3-dihydro-1H-inden-1-yl carbamate
(76) (1R, 2S)-7-chloro-2-(methoxymethoxy)-2,3-dihydro-1H-inden-1-yl carbamate
(77) (1S, 2R)-7-chloro-2,3-dihydro-1H-inden-1,2-diyl dicarbamate
(78) (1R, 2S)-7-chloro-2,3-dihydro-1H-inden-1,2-diyl dicarbamate
(79) (1R, 2S)-4-chloro-2,3-dihydro-1H-inden-1,2-diyl dicarbamate
(80) (1S, 2R)-4-chloro-2,3-dihydro-1H-inden-1,2-diyl dicarbamate
(81) (1S, 2R)-6-chloro-2,3-dihydro-1H-inden-1,2-diyl dicarbamate
(82) (1R, 2S)-6-chloro-2,3-dihydro-1H-inden-1,2-diyl dicarbamate
(83) (1S, 2R)-5,7-dichloro-2,3-dihydro-1H-inden-1,2-diyl dicarbamate
(84) (1R, 2S)-5,7-dichloro-2,3-dihydro-1H-inden-1,2-diyl dicarbamate
(85) (1S, 2R)-7-fluoro-2,3-dihydro-1H-inden-1,2-diyl dicarbamate
(86) (1R, 2S)-7-fluoro-2,3-dihydro-1H-inden-1,2-diyl dicarbamate
(87) (1S ,2R)-8-chloro-1-methoxy-1,2,3,4-tetrahydronaphthalen-2-yl carbamate
(88) (1S ,2R)-8-chloro-1-methoxy-1,2,3,4-tetrahydronaphthalen-2-yl isopropylcarbamate
(89) (1S ,2R)-8-chloro-1-(methoxymethoxy)-1,2,3,4-tetrahydronaphthalen-2-yl isopropylcarbamate
(90) (1S ,2R)-8-chloro-1-hydroxy-1,2,3,4-tetrahydronaphthalen-2-yl isopropylcarbamate
(91) (1S ,2R)-8-chloro-2-hydroxy-1,2,3,4-tetrahydronaphthalen-1-yl isopropylcarbamate
(92) (1S ,2R)-8-chloro-2-methoxy-1,2,3,4-tetrahydronaphthalen-1-yl isopropylcarbamate
(93) (1S ,2R)-8-chloro-2-(methoxymethoxy)-1,2,3,4-tetrahydronaphthalen-1-yl isopropylcarbamate In another embodiment of the present invention, there is provided a method of preventing or treating disease comprising administering a therapeutically effective amount of the compound having the formula 1 or a pharmaceutically acceptable salt thereof as an active ingredient, to a subject in need of treatment, wherein the disease is CNS disorder and/or and pain.

In one particular embodiment of the present invention, the compound having the formula 1 is in the form of racemate, enantiomer, diastereomer, a mixture of enantiomer, or a mixture of diastereomer.

In one particular embodiment of the present invention, the CNS disorders may include epilepsy or epilepsy-related syndrome, pediatric epilepsy or pediatric epilepsy-related syndrome, memory loss related disease, psychiatric disorder, movement disorder, neurodegenerative disease, Autism spectrum disease, prion disease, stroke, epileptogenesis, cerebral ischemia, myotonia, neonatal cerebral hemorrhage, amyotrophic lateral sclerosis and so on.

In one particular embodiment of the present invention, the pain is one or more selected from nociceptive pain, psychogenic pain, inflammatory pain, pathological pain, neuropathic pain, cancer pain, postoperative pain, trigeminal neuralgia pain, idiopathic pain, diabetic neuropathic pain, and migraine.

In one particular embodiment of the present invention, the epilepsy is an intractable epilepsy.

In one particular embodiment of the present invention, wherein the intractable epilepsy is selected from the group consisting of the group consisting of localization-related epilepsy, generalized epilepsy and syndromes thereof.

In one particular embodiment of the present invention, the localization-related epilepsy is cortical epilepsy or temporal lobe epilepsy.

In one particular embodiment of the present invention, the cortical epilepsy is a frontal lobe epilepsy, parietal lobe epilepsy, or occipital lobe epilepsy.

In one particular embodiment of the present invention, the epilepsy-related syndrome is an epileptic seizure.

In one particular embodiment of the present invention, the epileptic seizure is an intractable localization-related epilepsy, an intractable secondary generalized seizure, an intractable complex partial seizure or an intractable status epilepticus.

In one particular embodiment of the present invention, the memory loss related disease is Alzheimer's disease.

In one particular embodiment of the present invention, the movement disorder may include CBGD (Corticobasal Ganglionic Degeneration) Diskinesia, Dystonia, Tremors, Essential tremor, Parkinsonian tremor, Hereditary spastic paraplegia, Multiple system atrophy, Myoclonus, Parkinson's disease, Progressive supranuclear palsy, Restless legs syndrome, Rett syndrome, Spasticity, Sydenham's chorea, other choreas, Athetosis, Ballism Sterotypy, Tardive dyskinesia/dystonia, Tics, Tourette's syndrome, OPCA (Olivopontocerebellar atrophy), Hemibalisus, Hemi-facial spasm, Wilson's disease, Stiff man syndrome, Akinetic mutism, Psychomotor retardation, Painful legs moving toes syndrome, A gait disorder, Drug induced movement disorder.

In one particular embodiment of the present invention, the pediatric epilepsy or pediatric epilepsy-related syndrome is selected from the group consisting of Benign Myoclonic Epilepsy (BME), Severe Myoclonic Epilepsy of Infancy Borderland (SMEB), Severe Infantile Multifocal Epilepsy (SIMFE), and Intractable Childhood Epilepsy with Generalized Tonic Clonic Seizures (ICE-GTC), Dravet syndrome (Ds), Severe Myoclonic Epilepsy of Infancy (SMEI), Benign neonatal convulsions, Benign neonatal familial convulsions, Miscellaneous neonatal seizures, Febrile seizures, Early infantile epileptic encephalopathy, Early myoclonic encephalopathy, Infantile spasm, West syndromes, Severe myoclonic epilepsy of infancy, Benign myoclonic epilepsy of infancy, Benign partial epilepsy of infancy, Benign infantile familial convulsion, Symptomatic/cryptogenic partial epilepsies, Epilepsy with myoclonic absences, Lennox-Gastaut syndrome, Epilepsy with myoclonic-astatic seizures (Doose syndrome), Acquired epileptic aphasia (Landaw-Kleffner syndrome), Epilepsy with continuous spike-wave during low-wave sleep, Epilepsy with gastric seizures and hypothalamic hamartoma, Symptomatic/cryptogenic partial epilepsies and Childhood absence epilepsy.

In one particular embodiment of the present invention, the psychiatric disorder may include depressive disorder, bipolar disorder, anxiety disorder, mania, cocaine abuse, and so on.

In one particular embodiment of the present invention, the neurodegenerative disease may include Huntington's disease, Pick's disease, Diffuse Lewy body disease, Drug intoxication or withdrawal, Steel-Richardson syndrome, Shy-Drager syndrome, Cortical basal degeneration, Subacute sclerosing panencephalitis, Synucleinopathies, Primary progressive aphasia, Striatonigral degeneration, Machado-Joseph disease, Spinocerebellar ataxia, Olivopontocerebellar degenerations, Macular degeneration, Bulbar and Pseudobulbar palsy, Spinal and Spinobulbar muscular atrophy, Systemic lupus erythematosus, Primary lateral sclerosis, Familial spastic paraplegia, Werdnig-Hoffmann disease, Kugelberg-Welander disease, Tay-Sach's disease, Sandhoff disease, Familial spastic disease, Wohlfart-Kugelberg-Welander disease, Spastic paraparesis, Progressive multifocal leuko-encephalopathy, Familial dysautonomia and so on.

In one particular embodiment of the present invention, the stroke may include ischemic stroke or a hemorrhagic stroke and so on.

In one particular embodiment of the present invention, the Autism spectrum disease may include Autism, Asperger syndrome, PDD-NOS (Pervasive Developmental Disorder) and so on.

In one particular embodiment of the present invention, the prion disease may include Creutzfeldt-Jakob disease, Gerstmann-Straussler-Scheinker disease, Kuru disease, Fatal familial insomnia and so on.

In other embodiment of the present invention, a pharmaceutical composition comprising a therapeutically effective amount of the compound having the formula 1 or a pharmaceutically acceptable salt thereof as an active ingredient.

Advantageous Effects of Invention

The present invention provides a carbamate derivative compound for treating or preventing CNS disorders and/or pain, and/or pharmaceutically acceptable salt thereof as an active ingredient.

Furthermore, the present invention provides a method for treatment or prevention of CNS disorders and/or pain comprising administering a carbamate derivative compound in a pharmaceutically effective amount to a subject in need of treatment or prevention of CNS disorders like epilepsy and/or pain.

BRIEF DESCRIPTION OF DRAWINGS

FIG. 1 illustrates the number of cells in the region of interest (dorsal hippocampus-CA1, CA3, DG) in the Neuroprotection SE Model test.

FIG. 2 illustrates an effect of suppressing spasm in a rat model of symptomatic infantile spasms.

MODE FOR THE INVENTION

The carbamate derivative compound of the present invention having the formula 1 may be prepared by the following reaction schemes.

[Reaction scheme 1] Synthesis of cyclic carbonyl compound

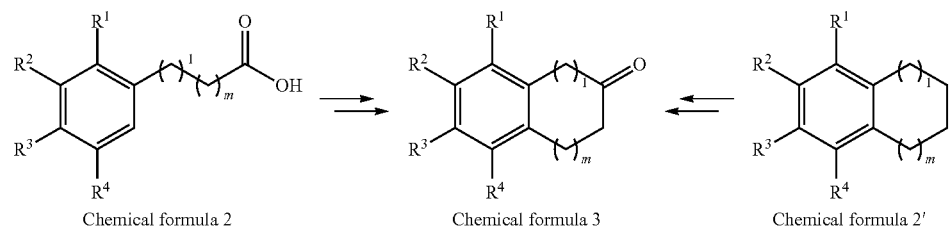

Chemical formula 2     Chemical formula 3     Chemical formula 2'

Cyclic carbonyl compound (Chemical formula 3) has commercially available materials based on the location of the substituent and carbonyl functional group, and the unsold compounds may be made through by ring closed reaction using acid compound (Chemical formula 2) or cyclic carbonyl compound (Chemical formula 3) may be synthesized by oxidation reaction on a compound of Chemical formula 2'.

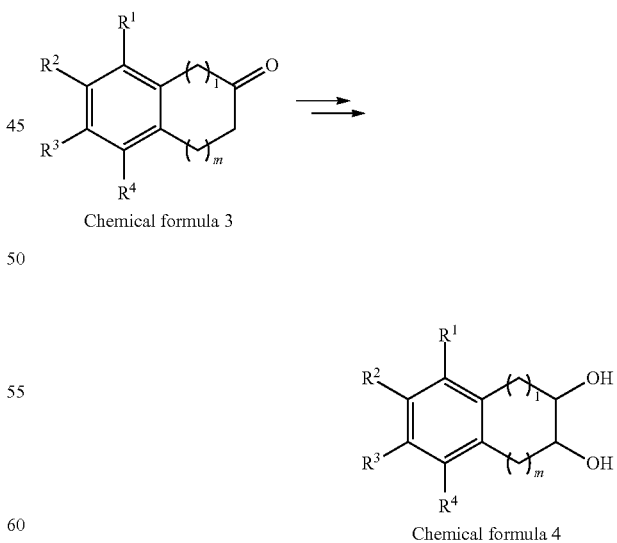

[Reaction scheme 2] Synthesis of diol compound

Chemical formula 3

Chemical formula 4

Diol compound (Chemical formula 4) may be synthesized by various reactions using cyclic carbonyl compound (Chemical formula 3). The reaction can go through, for examples, Oxidation/Reduction, Dihydroxylation, Epoxide opening and so on.

[Reaction scheme 3] Synthesis of carbamate derivative compound of the present invention

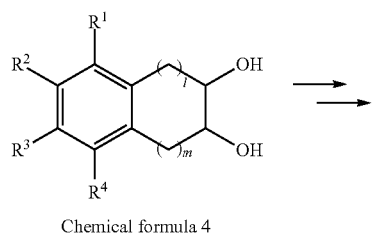

Chemical formula 4

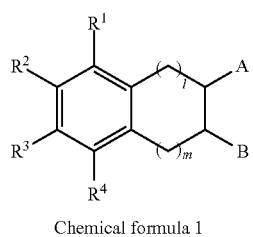

Chemical formula 1

The carbamate derivative compound (Chemical formula 1) may be synthesized by various reactions that are available to adopt various substituents applicable to A and B through Diol Compound (Chemical Formula 4).

In the above Chemical formula 2, 2', 3 and 4, the definitions of $R^1$, $R^2$, $R^3$ and $R^4$, A and B, l and m are the same as described in Chemical formula 1.

The following illustrate embodiments of the present invention but should not unduly limit the scope of the claims.

PREPARATION EXAMPLE 1

N-(5,6,7,8-tetrahydronaphthalen-1-yl)acetamide

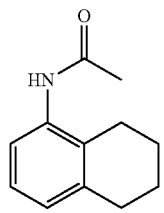

5,6,7,8-tetrahydronaphthalen-1-amine (100 g, 0.68 mol) in EtOH was added acetic anhydride (128 mL, 1.36 mol) and then the mixture was stirred at 0° C. for 3 hr. The solids were precipitated, filtered, and washed with n-hexanes to obtain the title compound (126 g, 80-99%). $^1$H NMR (400 MHz, CDCl$_3$) δ 1.77 (m, 2H), 1.83 (m, 2H), 2.20 (s, 3H), 2.59 (d, 2H, J=5.92), 2.78 (d, 2H, J=6.12), 6.88 (bs, 1H), 6.92 (d, 1H, J=7.68), 7.12 (t, 1H, J=7.72), 7.59 (d, 1H, J=7.88).

PREPARATION EXAMPLE 2

N-(8-oxo-5,6,7,8-tetrahydronaphthalen-1-yl)acetamide

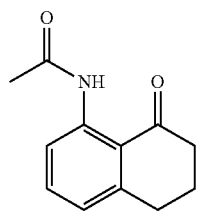

To a suspension of 15% aq. MgSO$_4$ (120 g in 680 mL of H$_2$O) in acetone (6 L) was added N-(5,6,7,8-tetrahydronaphthalen-1-yl)acetamide (Preparation example 1, 126 g, 0.68 mol) and KMnO$_4$ (251 g, 1.59 mol). The reaction mixture was stirred at room temperature for 5 hr. The mixture was filtered through Celite and solids were washed with DCM (~15 L). The filtrate was washed with water. The organic layer was separated, dried over MgSO$_4$, filtered, and concentrated under reduced pressure to obtain the title compound (130 g, 80-95%). $^1$H NMR (400 MHz, CDCl$_3$) δ 1.99-2.09 (m, 2H), 2.23 (s, 3H), 2.70 (t, 2H, J=6.36), 2.97 (t, 2H, J=6.04), 6.93 (d, 1H, J=6.72), 7.44 (t, 1H, J=7.92), 8.60 (d, 1H, J=8.44), 12.15 (bs, 1H).

PREPARATION EXAMPLE 3

8-amino-3,4-dihydronaphthalen-1(2H)-one

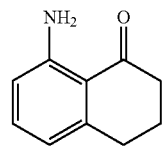 [SMILES: Nc1cccc2c1C(=O)CCC2]

N-(8-oxo-5,6,7,8-tetrahydronaphthalen-1-yl)acetamide (Preparation example 2, 130 g, 0.64 mol) in 6 N aq. HCl (1.5 L) was stirred vigorously at 90° C. for 2 hr. The reaction mixture was cooled to room temperature and pH of the mixture was raised up to pH 8 by adding NaHCO$_3$. The aqueous layer was extracted with EtOAc (5 L×2). The combined organic layer was washed with H$_2$O (3 L), dried over MgSO$_4$, and concentrated under reduced pressure. The crude compound was purified by a silica gel column to produce the title compound (80 g, 65-80%). $^1$H NMR (400 MHz, CDCl$_3$) δ 1.98-2.07 (m, 2H), 2.62 (t, 2H, J=6.36), 2.86 (t, 2H, J=6.08), 6.45 (m, 4H), 7.14 (t, 1H, J=7.56).

PREPARATION EXAMPLE 4

8-chloro-3,4-dihydronaphthalen-1(2H)-one

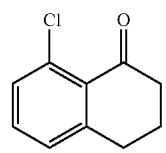

A mixture of copper(II) chloride (75.6 g, 0.56 mol) in acetonitrile was added t-butyl nitrite (82.4 mL, 0.69 mol). The mixture was stirred at 65° C., for 10 min The reaction mixture was added to a solution of 8-amino-3,4-hydronaphthalen-1(2H)-one (Preparation example 3, 70 g, 0.43 mol) in acetonitrile at 65° C. and then stirred for 15 min. The mixture was extracted with EtOAc at 3 times. The organic layer was washed with sat'NH$_4$Cl solution and water. The combined organic layer was dried over MgSO$_4$ and the solvent was concentrated under reduced pressure. The crude compound was purified by a silica gel column to produce the title compound (41 g, 40-60%). $^1$H NMR (400 MHz, CDCl$_3$) δ 2.07-2.14 (m, 2H), 2.69 (t, 2H, J=6.48), 2.97 (t, 2H, J=6.04), 7.14-7.18 (m, 1H), 7.31-7.34 (m, 2H).

PREPARATION EXAMPLE 5

8-chloro-1-oxo-1,2,3,4-tetrahydronaphthalen-2-yl acetate

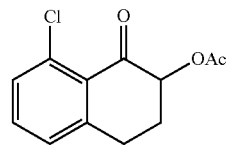

A mixture of 8-chloro-3,4-dihydronaphthalen-1(2H)-one (Preparation example 4, 5 g, 27.7 mmol) and Pb(OAc)$_4$ (24.5 g, 55.4 mmol) in benzene was refluxed for 3 days. The reaction mixture was quenched with water, diluted with EtOAc, and filtered through Celite. The organic layer was washed with water, dried over MgSO$_4$, and concentrated under reduced pressure. The crude compound was purified by recrystallization with EtOAc/n-Hexane to obtain the title compound (5.2 g, 60-85%). $^1$H NMR (400 MHz, CDCl$_3$) δ 2.22(s, 3H), 2.26-2.34 (m, 1H), 2.36-2.42 (m, 1H), 3.12-3.18 (m, 1H), 3.20-3.29 (m, 1H), 5.46 (dd, 1H, J=5.28, 13.24), 7.16-7.18 (m, 1H), 7.33-7.40 (m, 2H).

PREPARATION EXAMPLE 6

(1S, 2R)-8-chloro-1,2,3,4-tetrahydronaphthalen-1,2-diol

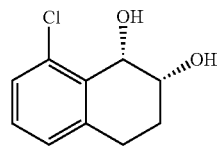

To a solution of 8-chloro-1-oxo-1,2,3,4-tetrahydronaphthalen-2-yl acetate (Preparation example 5, 5.16 g, 21.6 mmol) and (R,R)-[RuCl(TsDPEN)(p-cymene)] (69 mg, 0.1 mmol) in HCO$_2$H/Et$_3$N (10.9 mL/33.1 mL, 0.28 mol/0.24 mol) was stirred at room temperature for 3 days. The reaction mixture was diluted with DCM, washed with water, dried over MgSO$_4$, and concentrated under reduced pressure. The residue was filtered through silica gel pad, and concentrated. To a solution of the residue in MeOH was added 1N aq. NaOH, and stirred for 1 hr at room temperature. The mixture was neutralized by 1N aq. HCl to pH 7, extracted with DCM. The combined organic layer was washed with water, dried over MgSO$_4$, filtered and concentrated under reduced pressure. The crude product was purified by recrystallization with DCM/petroleum ether to obtain the title compound (3.6 g, 70-90%). $^1$H NMR (400 MHz, CDCl$_3$) δ 1.95 (m, 1H), 2.03 (m, 1H), 2.61 (s, 1H), 2.62 (s, 1H), 2.82 (m, 1H), 2.96 (m, 1H), 3.88 (m, 1H), 5.05 (t, 1H, J=3.60), 7.07 (d, 1H, J=7.64), 7.19 (t, 1H, J=7.72), 7.27 (d, 1H, J=6.88).

PREPARATION EXAMPLE 7

(1R, 2S)-8-chloro-1,2,3,4-tetrahydronaphthalen-1,2-diol

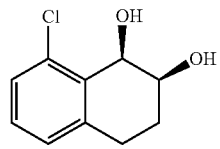 [SMILES: O[C@@H]1c2c(Cl)cccc2CC[C@@H]1O]

The substantially same method as described in Preparation example 6 was conducted, except that (S,S)-[RuCl(TsDPEN)(p-cymene)], was used instead of (R,R)-[RuCl(TsDPEN)(p-cymene)], to obtain the title compound (13.8 g, 70-90%). $^1$H NMR (400 MHz, CDCl$_3$) δ 1.95 (m, 1H), 2.03 (m, 1H), 2.61 (s, 1H), 2.62 (s, 1H), 2.82 (m, 1H), 2.96 (m, 1H), 3.88 (m, 1H), 5.05 (t, 1H, J=3.60), 7.07 (d, 1H, J=7.64), 7.19 (t, 1H, J=7.72), 7.27 (d, 1H, J=6.88).

PREPARATION EXAMPLE 8

7-chloro-2,3-dihydro-1H-inden-1-one

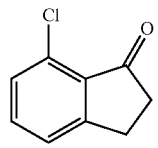

2-chlorobenzoic acid (100 g, 638.9 mmol) and thionyl chloride (70 mL, 958.0 mmol) in benzene were refluxed until no more gas evolution was observed. After being cooled to room temperature the mixture was concentrated under vacuum. The mixture was diluted with dichloroethane and added to a solution of AlCl$_3$ (93.7 g, 702.6 mmol) in dichloroethane at room temperature. Ethylene was bubbled through the mixture for 4 h and the mixture was stirred 20 h. The mixture was quenched with 3N aq. HCl. The resulting layers were separated and the aqueous layer was extracted with EtOAc. The combined organic layer was washed with H$_2$O, sat. NaHCO$_3$, brine, dried over MgSO$_4$, filtered and concentrated under reduced pressure. The material was added to a slurry of AlCl$_3$ (84.7 g, 1584.3 mol) and NaCl (352.1 g, 2640.5 mol) at 130° C. The mixture was stirred at 180° C. for 2 h, cooled to room temperature and quenched with ice followed by concentrated HCl. The resulting mixture was extracted with dichloromethane. Combined organic layer was dried over MgSO$_4$, filtered and concentrated under reduced pressure. The crude product was purified by silica gel column chromatography to produce the title compound (30.4 g, 25-45%). $^1$H NMR (400 MHz, CDCl$_3$) δ 2.71-2.77 (m, 2H) 3.109 (t, J=6.2, 2H), 7.28-7.32 (m, 1H), 7.34-7.39 (m, 1H), 7.47 (t, J=7.8, 1H).

PREPARATION EXAMPLE 9

7-chloro-2-hydroxy-2,3-dihydro-1H-inden-1-one

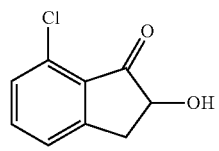 [SMILES: O=C1c2c(Cl)cccc2CC1O]

To a MeOH was added slowly KOH (20.2 g, 120.1 mol) at 0° C. and stirred for 0.5 h until the solution became a clear solution. To the solution was added portionwise 7-chloro-2,3-dihydro-1H-indan-1-one (Preparation example 8, 20.0 g, 120.1 mmol) and PhI(OAc)$_2$ (47.8 g, 144.1 mmol) at room temperature sequentially. The reaction mixture was stirred for 20 h at room temperature. The mixture was quenched by H$_2$O and removed MeOH under reduced pressure. The mixture was diluted with EtOAc, washed with H$_2$O and aqueous layer was extracted with EtOAc. Combined organic layer was washed with H$_2$O and concentrated under reduced pressure. The material was dissolved in EtOH, cooled to 0° C., 3N aq. HCl (20 mL, 60 mmol) was added dropwise and stirred for 0.5 h at 0° C. to room temperature. EtOH was removed under reduced pressure, diluted with EtOAc, washed with H$_2$O and aqueous layer was extracted with EtOAc. Combined organic layer was washed with sat. NaHCO$_3$, H$_2$O, dried over MgSO$_4$, filtered and concentrated. The crude product was purified by silica gel column chromatography to produce the title compound (10.2 g, 40-60%). $^1$H NMR (400 MHz, CDCl$_3$) δ 2.95-3.02 (m, 1H), 3.03 (s, 1H), 3.51-3.68 (m, 1H), 4.50-4.57 (m, 1H), 7.33-7.39 (m, 2H), 7.54 (t, J=7.8, 1H).

PREPARATION EXAMPLE 10

7-chloro-1-oxo-2,3-dihydro-1H-inden-2-yl acetate

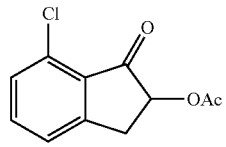

To a solution of 7-chloro-2-hydroxy-2,3-dihydro-1H-inden-1-one (Preparation example 9, 10.2 g, 56.0 mmol) in dichloromethane (280 mL) was added 4-dimethylaminopyridine (680 mg, 5.6 mmol) and triethylamine (47 mL, 336.1 mmol) at 0° C. Acetic anhydride (15.9 mL, 168.1 mmol) was added at the same temperature. The reaction mixture was stirred for 2 h. The reaction mixture was quenched with H$_2$O and aqueous layer was extracted with dichloromethane. Combined organic layer was washed with H$_2$O, dried over MgSO$_4$, filtered and concentrated under reduced pressure. The crude product was purified by silica gel column chromatography to produce the title compound (11.7 g, 80-95%). $^1$H NMR (400 MHz, CDCl$_3$) δ 2.18 (s, 3H), 2.95-3.07 (m, 1H), 3.57-3.65 (m, 1H), 5.38-5.45 (m, 1H), 7.32-7.37 (m, 2H), 7.54 (t, J=7.8, 1H).

PREPARATION EXAMPLE 11

(1S,2R)-7-chloro-2,3-dihydro-1H-inden-1,2-diol

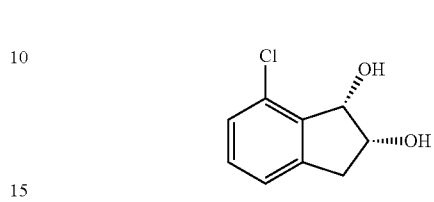

To a solution of 7-chloro-1-oxo-2,3-dihydro-1H-inden-2-yl acetate (Preparation example 10, 3.9 g, 17.2 mmol) in HCO$_2$H/triethylamine (8.7 mL/26.3 mL, 13.2 equiv./11.0 equiv.) was added (R,R)-[RuCl(TsDPEN)(p-cymene)] (55 mg, 0.16 mmol, 0.005 equiv.) and stirred for 20 h at room temperature. The reaction mixture was diluted with EtOAc then washed with H$_2$O, dried over MgSO$_4$, filtered and concentrated under reduced pressure. To a solution of the residue in MeOH (77.0 mL) was added 1N aq. NaOH (8.6 mL, 8.6 mmol) and stirred for 1 h at room temperature. The mixture was neutralized by 1N aq. HCl to pH 7 then extracted with EtOAc. The combined organic layer was washed with H$_2$O, dried over MgSO$_4$, filtered and concentrated under reduced pressure. The crude product was purified by silica gel column chromatography to produce the title compound (2.5 g, 70-90%). $^1$H NMR (400 MHz, CDCl$_3$) δ 2.64 (d, J=4.0, 1H), 2.80 (d, J=6.4, 1H), 2.97-3.06 (m, 1H), 3.13-3.22 (m, 1H), 4.48-4.56 (m, 1H), 5.13-5.19 (m, 1H), 7.12-7.17 (m, 1H), 7.20-7.25 (m, 2H).

PREPARATION EXAMPLE 12

(1S,2R)-2-(tert-butyldimethylsilyloxy)-7-chloro-2,3-dihydro-1H-inden-1-ol

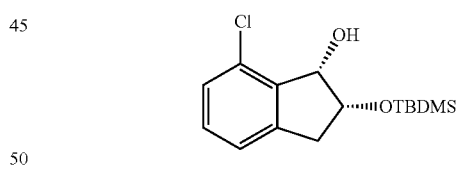

To a solution of (1S,2R)-7-chloro-2,3-dihydro-1H-indene-1,2-diol (Preparation example 11, 2.5 g, 13.7 mmol) in dichloromethane (135 mL) was added triethylamine (2.0 mL, 14.3 mmol) at −78° C., Stirred for 5 min and tert-butyldimethylsilyl trifluoromethanesulfonate (3.0 mL, 13.0 mmol) was added dropwise at −78° C. Reaction mixture was stirred for 0.5 h at −78° C. to 0° C. The reaction mixture was quenched with H$_2$O at 0° C. and aqueous layer was extracted with dichloromethane. Combined organic layer was washed with H$_2$O, dried over MgSO$_4$, filtered and concentrated under reduced pressure. The crude product was purified by silica gel column chromatography to produce the title compound (3.2 g, 70-90%). $^1$H NMR (400 MHz, CDCl$_3$) δ 0.17 (s, 3H) 0.18 (s, 3H), 0.95 (s, 9H), 2.98-3.15 (m, 2H), 3.15-3.18 (m, 1H), 4.45-4.52 (m, 1H), 4.95-5.0 (m, 1H), 7.06-7.12 (m, 1H), 7.17-7.23 (m, 2H).

PREPARATION EXAMPLE 13

(1S,2R)-2-(tert-butyldimethylsilyloxy)-7-chloro-2,3-dihydro-1H-inden-1-yl carbamate

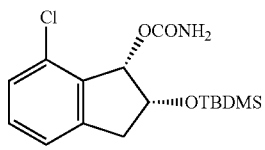

To a solution of (1S,2R)-2-(tert-butyldimethylsilyloxy)-7-chloro-2,3-dihydro-1H-inden-1-ol (Preparation example 12, 3.2 g, 10.8 mmol) in tetrahydrofuran (50 mL), cooled to −78° C. and chlorosulfonyl isocyanate (1.0 mL, 11.9 mmol) was added dropwise and stirred for 0.5 h at −78° C. The reaction mixture was warmed to 0° C., and quenched with $H_2O$ and aqueous layer was extracted with EtOAc. Combined organic layer was washed with sat. $NaHCO_3$, $H_2O$, dried over $MgSO_4$, filtered and concentrated under reduced pressure. The crude product was purified by silica gel column chromatography to produce the title compound (3.2 g, 80-95%). $^1$H NMR (400 MHz, $CDCl_3$) δ 0.14 (s, 3H) 0.16 (s, 3H), 0.93 (s, 9H), 3.0-3.16 (m, 2H), 4.45-4.55 (m, 1H), 4.62 (s, 2H), 6.16 (d, J=5.6, 1H), 7.11 (d, J=6.8, 1H), 7.20-7.28 (m, 2H).

PREPARATION EXAMPLE 14

(1R,2S)-7-chloro-2,3-dihydro-1H-inden-1,2-diol

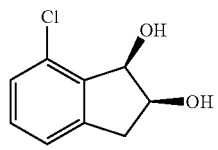 [SMILES: O[C@@H]1c2c(Cl)cccc2C[C@@H]1O]

The substantially same method as described in Preparation example 11 was conducted, except that (S,S)-[RuCl(TsDPEN)(p-cymene)], was used instead of (R,R)-[RuCl(TsDPEN)(p-cymene)], to obtain the title compound (8.0 g, 70-90%). $^1$H NMR (400 MHz, $CDCl_3$) δ 2.66 (d, J=4.4, 1H), 2.81 (d, J=6.8, 1H), 2.97-3.06 (m, 1H), 3.14-3.23 (m, 1H), 4.48-4.55 (m, 1H), 5.14-5.18 (m, 1H), 7.12-7.16 (m, 1H), 7.20-7.24 (m, 2H).

PREPARATION EXAMPLE 15

(1R,2S)-2-((tert-butyldimethylsilyl)oxy)-7-chloro-2,3-dihydro-1H-inden-1-ol

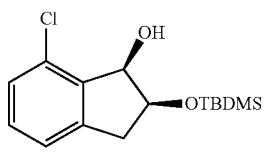 [SMILES: CC(C)(C)[Si](C)(C)O[C@H]1Cc2cccc(Cl)c2[C@H]1O]

The substantially same method as described in Preparation example 12 was conducted, except that (1R,2S)-7-chloro-2,3-dihydro-1H-inden-1,2-diol (Preparation example 14), was used instead of (1S,2R)-7-chloro-2,3-dihydro-1H-inden-1,2-diol (Preparation example 11), to obtain the title compound (5.7 g, 70-90%). $^1$H NMR (400 MHz, $CDCl_3$) δ 0.17 (s, 3H), 0.18 (s, 3H), 0.95 (s, 9H), 3.10-3.15 (m, 1H), 4.44-4.52 (m, 1H), 4.95-5.00 (m, 1H), 7.06-7.12 (m, 1H), 7.17-7.23 (m, 2H).

PREPARATION EXAMPLE 16

(1R,2S)-2-((tert-butyldimethylsilyl)oxy)-7-chloro-2,3-dihydro-1H-inden-1-yl carbamate

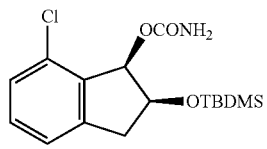

The substantially same method as described in Preparation example 13 was conducted, except that (1R,2S)-2-((tert-butyldimethylsilyl)oxy)-7-chloro-2,3-dihydro-1H-inden-1-ol (Preparation example 15), was used instead of (1S,2R)-2-((tert-butyldimethylsilyl)oxy)-7-chloro-2,3-dihydro-1H-inden-1-ol (Preparation example 12), to obtain the title compound (6.4 g, 80-95) $^1$H NMR (400 MHz, $CDCl_3$) δ 0.14 (s, 3H) 0.16 (s, 3H), 0.93 (s, 9H), 3.0-3.16 (m, 2H), 4.45-4.55 (m, 1H), 4.62 (s, 2H), 6.16 (d, J=5.6, 1H), 7.11 (d, J=6.8, 1H), 7.20-7.28 (m, 2H).

PREPARATION EXAMPLE 17 tert-butyl(((1R,2S)-7-chloro-1-(methoxymethoxy)-2,3-dihydro-1H-inden-2-yl)oxy)dimethylsilsne

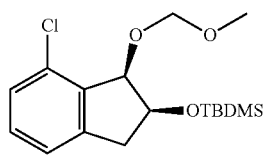 [SMILES: COCO[C@@H]1c2c(Cl)cccc2C[C@@H]1O[Si](C)(C)C(C)(C)C]

(1R,2S)-2-(tert-butyldimethylsilyloxy)-7-chloro-2,3-dihydro-1H-inden-1-ol (Preparation example 15, 5.7 g, 19.0 mmol) was dissolved in dichloromethane (95 mL) and cooled to 0. Diisopropylethylamine (6.6 mL, 95.0 mmol) was added and stirred for 5 min Chloromethyl methyl ether (7.2 mL 95.0 mmol) was added dropwise at 0° C. and stirred for 5 h at 0° C. to room temperature. The reaction mixture was quenched with $H_2O$, dilute with EtOAc and aqueous layer was extracted with EtOAc. Combined organic layer was washed with $H_2O$, dried over $MgSO_4$, filtered and concentrated under reduced pressure. The crude product was purified by silica gel column chromatography to give as a colorless oil (6.4 g, 80-95%). $^1$H NMR (400 MHz, $CDCl_3$) δ 0.15 (d, J=2.0, 6H), 0.94 (s, 9H), 2.94-3.01 (m, 1H), 3.12-3.20 (m, 1H), 3.48 (s, 3H), 4.34-4.41 (m, 1H), 4.80 (d, J=6.8 1H), 5.05 (t, J=5.6, 2H), 7.08-7.13 (m, 1H), 7.18-7.24 (m, 2H).

PREPARATION EXAMPLE 18

(1R,2S)-7-chloro-1-(methoxymethoxy)-2,3-dihydro-1H-inden-2-ol

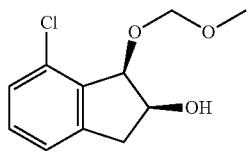

To a solution of tert-butyl((1R,2S)-7-chloro-1-(methoxymethoxy)-2,3-dihydro-1H-inden-2-yloxy)dimethylsilane (Preparation example 17, 6.4 g, 18.7 mmol) in tetrahydrofuran (187 mL) was added dropwise 1 M tetra-n-butylammonium fluoride solution (22.5 mL 22.5 mmol) at 0° C. and stirred for 1 h at 0° C. to room temperature. The reaction mixture was quenched with H$_2$O, dilute with EtOAc and aqueous layer was extracted with EtOAc. Combined organic layer was washed with H$_2$O, dried over MgSO$_4$, filtered and concentrated under reduced pressure. The crude product was purified by silica gel column chromatography to give as a white solid (3.2 g, 70-90%). $^1$H NMR (400 MHz, CDCl$_3$) δ 2.9-3.07 (m, 1H), 3.11-3.19 (m, 1H), 3.23 (d, J=8.4, 1H), 3.48 (s, 3H), 4.4-4.48 (m, 1H), 4.83 (d, J=6.8, 1H), 5.00-5.08 (m, 2H), 7.11-7.15 (m, 1H), 7.19-7.26 (m, 2H).

PREPARATION EXAMPLE 19 tert-butyl(((1S,2R)-7-chloro-1-(methoxymethoxy)-2,3-dihydro-1H-inden-2-yl)oxy)dimethylsilsne

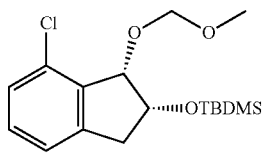 [SMILES: COCO[C@H]1c2c(Cl)cccc2C[C@H]1O[Si](C)(C)C(C)(C)C]

The substantially same method as described in Preparation example 17 was conducted, except that ((1S,2R)-2-(tert-butyldimethylsilyloxy)-7-chloro-2,3-dihydro-1H-inden-1-ol (Preparation example 12), was used instead of (1R,2S)-2-(tert-butyldimethylsilyloxy)-7-chloro-2,3-dihydro-1H-inden-1-ol (Preparation example 15), to obtain the title compound (5.7 g, 80-95%). $^1$H NMR (400 MHz, CDCl$_3$) δ 0.15 (d, J=2.0, 6H), 0.94 (s, 9H), 2.94-3.01 (m, 1H), 3.12-3.20 (m, 1H), 3.48 (s, 3H), 4.34-4.41 (m, 1H), 4.80 (d, J=6.8 1H), 5.05 (t, J=5.6, 2H), 7.08-7.13 (m, 1H), 7.18-7.24 (m, 2H).

PREPARATION EXAMPLE 20

(1S,2R)-7-chloro-1-(methoxymethoxy)-2,3-dihydro-1H-inden-2-ol

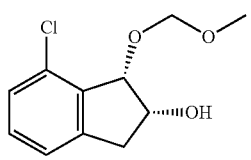

The substantially same method as described in Preparation example 18 was conducted, except that tert-butyl(((1S,2R)-7-chloro-1-(methoxymethoxy)-2,3-dihydro-1H-inden-2-yl)oxy)dimethylsilsne (Preparation example 19), was used instead of tert-butyl(((1R,2S)-7-chloro-1-(methoxymethoxy)-2,3-dihydro-1H-inden-2-yl)oxy)dimethylsilane (Preparation example 17), to obtain the title compound (4.4 g, 70-90%). $^1$H NMR (400 MHz, CDCl$_3$) δ 2.9-3.07 (m, 1H), 3.11-3.19 (m, 1H), 3.23 (d, J=8.4, 1H), 3.48 (s, 3H), 4.4-4.48 (m, 1H), 4.83 (d, J=6.8, 1H), 5.00-5.08 (m, 2H), 7.11-7.15 (m, 1H), 7.19-7.26 (m, 2H).

PREPARATION EXAMPLE 21

8-chloro-1,2,3,4-tetrahydronaphthalen-1-ol

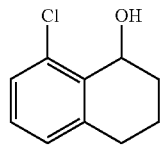 [SMILES: OC1CCCc2cccc(Cl)c21]

To a stirred solution of 8-chloro-3,4-dihydronaphthalen-1(2H)-one (Preparation example 4, 15.0 g, 83.0 mmol) in MeOH (150 mL) was added sodium borohydride (3.5 g, 91.3 mmol) at 0° C. The mixture was stirred for 3 h at rt. TLC showed complete consumption of SM. The resulting mixture was quenched with H$_2$O, extracted with EtOAc, washed with H$_2$O, dried over MgSO$_4$, filtered and concentrated under reduced pressure. The crude product was purified by silica gel column chromatography to produce the title compound (12.9 g, 85%). $^1$H NMR (400 MHz, CDCl$_3$) δ 1.74-1.84 (m, 2H), 1.94-2.06 (m, 1H), 2.18-2.24 (m, 1H), 2.40 (s, 1H), 2.76-2.76 (m, 1H), 2.85-2.89 (m, 1H), 5.10 (t, J=3.2, 1H), 7.06 (d, J=7.6, 1H), 7.16 (t, J=7.6, 1H), 7.25 (d, J=8.0, 1H).

PREPARATION EXAMPLE 22

5-chloro-1,2-dihydronaphthalene

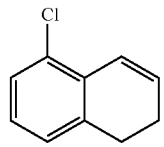 [SMILES: Clc1cccc2c1C=CCC2]

To a solution of 8-chloro-1,2,3,4-tetrahydronaphthalen-1-ol (Preparation example 21, 6.5 g, 35.6 mmol) and p-toluenesulfonic acid (1.4 g, 7.1 mmol) in toluene (180 mL) were heated at 110° C. for 6 h under Dean-Stark equipment. The resulting mixture was quenched with sat. NaHCO$_3$, diluted with EtOAc, washed with H$_2$O, dried over MgSO$_4$, filtered and concentrated under reduced pressure. The crude product was purified by silica gel column chromatography to produce the title compound (4.68 g, 80%). $^1$H NMR (400 MHz, CDCl$_3$) δ 2.29-2.35 (m, 2H), 2.81 (t, J=8.0, 2H), 6.17-6.22 (m, 1H), 6.90 (dt, J=6.0, 2.0, 1H), 7.01-7.07 (m, 2H), 7.20-7.22 (m, 1H).

PREPARATION EXAMPLE 23

8-chloro-1,2,3,4-tetrahydronaphthalene-1,2-diol

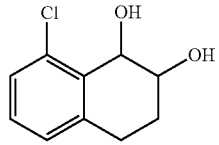 [SMILES: OC1CCc2cccc(Cl)c2C1O]

To a stirred solution of 5-chloro-1,2-dihydronaphthalene (Preparation example 22, 4.6 g, 28.0 mmol) in a mixture of acetone/H$_2$O/tert-butanol (77/15.4/15.4 mL, respectively) was added osmium tetroxide (142 mg, 0.56 mmol) and N-methylmorpholine N-oxide (4.9 g, 42.0 mmol) at room temperature then stirred for 5 h. The resulting mixture was diluted with EtOAc, washed with H$_2$O, dried over MgSO$_4$, filtered and concentrated under reduced pressure. The crude product was purified by silica gel column chromatography to produce the title compound (4.22 g, 76%). $^1$H NMR (400 MHz, CDCl$_3$) δ 1.92-1.99 (m, 1H), 2.01-2.10 (m, 1H), 2.60 (s, 1H), 2.68 (s, 1H), 2.82-2.90 (m, 1H), 2.96-3.04 (m, 1H), 3.88-3.95 (m, 1H), 5.05 (t, J=3.6, 1H), 7.07 (d, J=7.6, 1H), 7.19 (t, J=7.7, 1H), 7.27 (d, J=6.9, 1H).

PREPARATION EXAMPLE 24 tert-butyl((8-chloro-3,4-dihydronaphthalen-1-yl)oxy)diphenylsilane

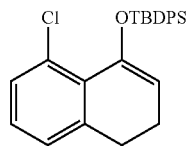

To a stirred solution of 8-chloro-3,4-dihydronaphthalen-1(2H)-one (Preparation example 4, 1.0 g, 5.53 mmol) in THF (28 mL) was added KHMDS (1 M in THF, 8.9 mL, 8.85 mmol) at −78° C. under N$_2$. The mixture was stirred for 30 min. The mixture was added TBDPS-Cl (1.3 mL, 4.98 mmol) then slowly warmed to room temperature. The mixture was stirred for 13 h. The resulting mixture was diluted with EtOAc, washed with H$_2$O and brine, dried over MgSO$_4$, filtered and concentrated under reduced pressure. The crude product was purified by silica gel column chromatography to produce the title compound (1.57 g, 68%). $^1$H NMR (400 MHz, CDCl$_3$) δ 1.05 (s, 9H), 1.82-1.87 (m, 2H), 2.45 (t, J=7.2, 2H), 4.88 (t, J=5.4, 1H), 7.01-7.09 (m, 2H), 7.28 (dd, J=1.4, 7.8, 1H), 7.35-7.45 (m, 7H), 7.80 (dd, J=1.6, 8.0, 3H).

PREPARATION EXAMPLE 25 tert-butyl(((1aR,7bR)-7-chloro-1a,2,3,7b-tetrahydronaphtho[1,2-b]oxiren-7b-yl)oxy)diphenylsilane

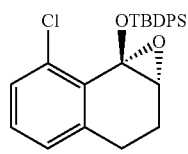

tert-butyl((8-chloro-3,4-dihydronaphthalen-1-yl)oxy)diphenylsilane (Preparation example 24, 1.57 g, 3.75 mmol) was added to a 250 mL round-bottom flask. The flask was cooled to 0° C. Acetonitrile (23 mL), dimethoxymethane (46 mL), and sodium borate-ethylenediaminetetraacetic acid disodium salt (46 mL) were added to the cooled flask. D-Fructose-derived Shi catalyst (0.29 g, 1.12 mmol) and tetrabutylammonium bisulfate (51 mg, 0.15 mmol) were added in sequence to the stirring mixture at 0° C. Separately, oxone (3.18 g, 5.17 mmol) was added ethylenediaminetetraacetic acid disodium salt (29 mL) and the resulting solution was drawn into a 50 mL disposable plastic syringe. A solution of potassium carbonate (3.0 g, 21.72 mmol) in water (29 mL) was drawn into a second 50 mL disposable plastic syringe. The contents of both syringes were added simultaneously over 90 min using a syringe drive to the ice-cooled, stirring reaction mixture. After the addition was complete, the reaction mixture was stirred for 30 min at 0° C., then was diluted with ice-cold pentane and ice-cold water, producing a biphasic mixture. The layers were separated. The aqueous layer was extracted with ice-cold pentane. The organic extracts were combined and the combined solution was washed with brine, then was dried over sodium sulfate. The dried solution was filtered and the filtrate was concentrated. The crude product was purified by silica gel column chromatography to produce the title compound (1.3 g, 80%). $^1$H NMR (400 MHz, CDCl$_3$) δ 1.11 (s, 9H), 2.10-2.22 (m, 2H), 2.81-2.89 (m, 1H), 3.10 (td, J=5.2, 17.2, 1H), 4.35 (q, J=4.9, 1H), 7.06-7.08 (m, 1H), 7.26-7.29 (m, 2H), 7.34-7.46 (m, 6H), 7.70-7.72 (m, 4H).

PREPARATION EXAMPLE 26

(1R,2R)-1-((tert-butyldiphenylsilyl)oxy)-8-chloro-1,2,3,4-tetrahydronaphthalen-2-ol

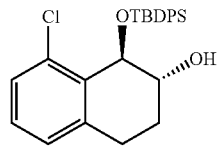

To a stirred solution of tert-butyl(((1aR,7bR)-7-chloro-1a,2,3,7b-tetrahydronaphtho[1,2-b]oxiren-7b-yl)oxydiphenylsilane (Preparation example 25, 0.1 g, 0.23 mmol) in THF (4 mL) was added borane dimethylsulfide (2 M in THF, 0.23 mL, 0.46 mmol) then heated to reflux. The mixture was stirred for 5 h. The resulting mixture was diluted with EtOAc, washed with H$_2$O and brine, dried over MgSO$_4$, filtered and concentrated under reduced pressure. The crude product was purified by silica gel column chromatography to produce the title compound (0.05 g, 50%). $^1$H NMR (400 MHz, CDCl$_3$) δ 0.94 (s, 9H), 1.81-1.86 (m, 1H), 1.93-2.00 (m, 1H), 2.09 (d, J=4.4, 1H), 2.66-2.72 (m, 1H), 3.13-3.21 (m, 1H), 4.25-4.27 (m, 1H), 4.78 (t, J=3.4, 1H), 7.10 (d, J=7.2, 1H), 7.18 (t, J=7.8, 1H), 7.26-7.47 (m, 7H), 7.55-7.57 (m, 2H), 7.65-7.67 (m, 2H).

PREPARATION EXAMPLE 27

(1R,2R)-1-((tert-butyldiphenylsilyl)oxy)-8-chloro-1,2,3,4-tetrahydronaphthalen-2-yl carbamate

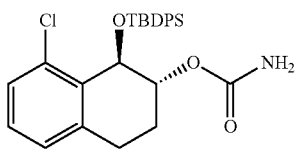

To a stirred solution of (1R,2R)-1-((tert-butyldiphenylsilyl)oxy)-8-chloro-1,2,3,4-tetrahydronaphthalen-2-ol (Preparation example 26, 0.44 g, 1.01 mmol) in THF (10 mL) was added chlorosulfonyl isocyanate (0.08 mL, 1.01 mmol) at 0° C. then stirred for 1 h. The resulting mixture was diluted with EtOAc, washed with H$_2$O and brine, dried over MgSO$_4$, filtered and concentrated under reduced pressure. The crude product was purified by silica gel column chromatography to produce the title compound (0.38 g, 78%). $^1$H NMR (400 MHz, CDCl$_3$) δ 1.00 (s, 9H), 1.62-1.68 (m, 1H), 1.74-1.83 (m, 1H), 2.65 (dd, J=4.4, 16.8, 1H), 3.10-3.19 (m, 1H), 4.39-4.41 (m, 1H), 4.53 (br s, 2H), 5.89 (d, J=2.0, 1H), 7.11 (d, J=7.6, 1H), 7.20-7.30 (m, 2H), 7.30-7.45 (m, 6H), 7.63-7.66 (m, 4H).

PREPARATION EXAMPLE 28 tert-butyl(((1aS,7bS)-7-chloro-1a,2,3,7b-tetrahydronaphtho[1,2-b]oxiren-7b-yl)oxy)diphenylsilane

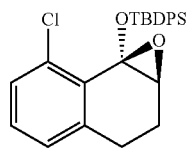

The substantially same method as described in Preparation example 25 was conducted, except that L-Fructose-derived Shi catalyst, was used instead of D-Fructose-derived Shi catalyst, to obtain the title compound (1.3 g, 80%). $^1$H NMR (400 MHz, CDCl$_3$) δ 1.11 (s, 9H), 2.10-2.22 (m, 2H), 2.81-2.89 (m, 1H), 3.10 (td, J=5.2, 17.2, 1H), 4.35 (q, J=4.9, 1H), 7.06-7.08 (m, 1H), 7.26-7.29 (m, 2H), 7.34-7.46 (m, 6H), 7.70-7.72 (m, 4H).

PREPARATION EXAMPLE 29

(1S,2S)-1-((tert-butyldiphenylsilyl)oxy)-8-chloro-1,2,3,4-tetrahydronaphthalen-2-ol

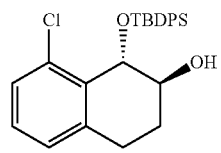

The substantially same method as described in Preparation example 26 was conducted, except that tert-butyl(((1aS,7bS)-7-chloro-1a,2,3,7b-tetrahydronaphtho[1,2-b]oxiren-7b-yl)oxy)diphenylsilane (Preparation example 28), was used instead of tert-butyl(((1aR,7bR)-7-chloro-1a,2,3,7b-tetrahydronaphtho[1,2-b]oxiren-7b-yl)oxy)diphenylsilane (Preparation example 25), to obtain the title compound (0.05 g, 50%). $^1$H NMR (400 MHz, CDCl$_3$) δ 0.94 (s, 9H), 1.81-1.86 (m, 1H), 1.93-2.00 (m, 1H), 2.09 (d, J=4.4, 1H), 2.66-2.72 (m, 1H), 3.13-3.21 (m, 1H), 4.25-4.27 (m, 1H), 4.78 (t, J=3.4, 1H), 7.10 (d, J=7.2, 1H), 7.18 (t, J=7.8, 1H), 7.26-7.47 (m, 7H), 7.55-7.57 (m, 2H), 7.65-7.67 (m, 2H).

PREPARATION EXAMPLE 30

(1S,2S)-1-((tert-butyldiphenylsilyl)oxy)-8-chloro-1,2,3,4-tetrahydronaphthalen-2-yl carbamate

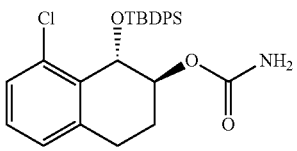

The substantially same method as described in Preparation example 27 was conducted, except that (1S,2S)-1-((tert-butyldiphenylsilyl)oxy)-8-chloro-1,2,3,4-tetrahydronaphthalen-2-ol (Preparation example 29), was used instead of (1R,2R)-1-((tert-butyldiphenylsilyl)oxy)-8-chloro-1,2,3,4-tetrahydronaphthalen-2-ol (Preparation example 26), to obtain the title compound (0.38 g, 78%). $^1$H NMR (400 MHz, CDCl$_3$) δ 1.00 (s, 9H), 1.62-1.68 (m, 1H), 1.74-1.83 (m, 1H), 2.65 (dd, J=4.4, 16.8, 1H), 3.10-3.19 (m, 1H), 4.39-4.41 (m, 1H), 4.53 (br s, 2H), 5.89 (d, J=2.0, 1H), 7.11 (d, J=7.6, 1H), 7.20-7.30 (m, 2H), 7.30-7.45 (m, 6H), 7.63-7.66 (m, 4H).

PREPARATION EXAMPLE 31

4-(4-chlorophenyl)butanoic acid

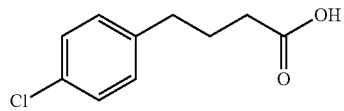 [SMILES: O=C(O)CCCc1ccc(Cl)cc1]

A heterogeneous mixture of 3-(4-chlorobenzoyl)-propionic acid (20 g, 188.1 mmol), potassium hydroxide (11.7 g, 208.7 mmol), hydrazine monohydrate (10 mL, 205.1 mmol), and diethylene glycol (84 mL) were heated in a flask equipped with a Dean-Stark trap and condenser. The mixture became homogeneous on heating. The mixture maintained at 120-130° C. for 1.5 h and raised to 180° C. for 3 h. The reaction mixture was cooled to room temperature, diluted with water and added 2.5M HCl. The mixture was allowed to stand for 16 h and the white solid collected by filtration. To remove the residual diethylene glycol, the solid dissolved in sat. K$_2$CO$_3$ and water. The clear solution was poured into stirred 2.5M HCl. White solid was collected by filtration, washed with water (30.0 g, 79%). $^1$H NMR (400 MHz, CDCl$_3$) δ 2.12-2.14 (m, 2H), 2.37 (t, J=9.0, 2H), 2.56 (t, J=6.0, 2H), 7.12 (s, 2H), 7.26 (s, 2H).

PREPARATION EXAMPLE 32

7-chloro-3,4-dihydronaphthalen-1(2H)-one

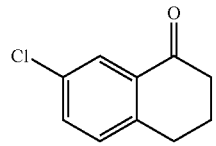 [SMILES: O=C1CCCc2ccc(Cl)cc21]

Polyphosphoric acid (20 g, excess) was place in a beaker and heated to 90° C. 4-(4-chlorophenyl)butanoic acid (Preparation example 31, 3 g, 17 mmol) was added in portions. The mixture was stirred for 5 min an additional portion of polyphosphoric acid (20 g, excess) was added and heated to 90° C. for 5 min The thick, homogenous viscous orange oil was cooled to 60° C. before water was added. When the reaction was completed, the mixture was cooled to room temperature and extracted with EtOAc. The organic layer was washed with water, 1N NaOH and water, dried over MgSO$_4$, and evaporated under reduced pressure. The crude product was purified by silica gel column chromatography to give as a white solid (2.5 g, 81%). $^1$H NMR (400 MHz, CDCl$_3$) δ 2.12-2.18 (m, 2H), 2.67 (t, J=6.8, 2H), 2.95 (t, J=6.8, 2H), 7.22 (d, J=8.0, 1H), 7.42 (dd, J=10.2, 2.4, 1H), 7.85 (d, J=2.4, 1H).

PREPARATION EXAMPLE 33

7-chloro-1-oxo-1,2,3,4-tetrahydronaphthalen-2-yl acetate

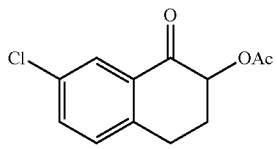 [SMILES: CC(=O)OC1CCc2ccc(Cl)cc2C1=O]

The substantially same method as described in Preparation example 5 was conducted, except that 7-chloro-3,4-dihydronaphthalen-1(2H)-one (Preparation example 32), was used instead of 8-chloro-3,4-dihydronaphthalen-1(2H)-one (Preparation example 4), to obtain the title compound (7.5 g, 79%). $^1$H NMR (400 MHz, CDCl$_3$) δ 2.23 (s, 3H), 2.27-2.34 (m, 1H), 2.38-2.45 (m, 1H), 3.05-3.11 (m, 1H), 3.14-3.23 (m, 1H), 5.54 (dd, J=13.2, 2.6, 1H), 7.24 (d, J=8.0, 1H), 7.48 (dd, J=10.2, 2.4, 1H), 8.0 (d, J=2.4, 1H).

PREPARATION EXAMPLE 34

(1S ,2R)-7-chloro-1,2,3,4-tetrahydronaphthalene-1,2-diol

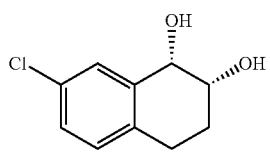 [SMILES: O[C@@H]1CCc2ccc(Cl)cc2[C@@H]1O]

The substantially same method as described in Preparation example 11 was conducted, except that 7-chloro-1-oxo-1,2,3,4-tetrahydronaphthalen-2-yl acetate (Preparation example 33), was used instead of 7-chloro-1-oxo-2,3-dihydro-1H-inden-2-yl acetate (Preparation example 10), to obtain the title compound (4.5 g, 86%). $^1$H NMR (400 MHz, CDCl$_3$) δ 1.94-1.95 (m, 1H), 2.04-2.13 (m, 1H), 2.17-2.18 (m, 1H), 2.35-2.37 (m, 1H), 2.71-2.79 (m, 1H), 2.88-2.98 (m, 1H), 4.07-4.09 (m, 1H), 4.66-4.71 (m, 1H), 7.07 (d, J=8.0, 1H), 7.20 (dd, J=10.2, 2.4, 1H), 7.47 (d, J=2.4, 1H).

PREPARATION EXAMPLE 35

(1R,2S)-7-chloro-1,2,3,4-tetrahydronaphthalene-1,2-diol

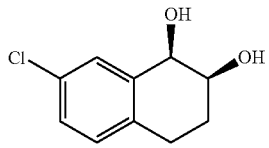 [SMILES: O[C@@H]1c2cc(Cl)ccc2CC[C@@H]1O]

The substantially same method as described in Preparation example 11 was conducted, except that 7-chloro-1-oxo-1,2,3,4-tetrahydronaphthalen-2-yl acetate (Preparation example 33) and (R,R)-[RuCl(TsDPEN)(p-cymene)], was used instead of 7-chloro-1-oxo-2,3-dihydro-1H-inden-2-yl acetate (Preparation example 10) and (S,S)-[RuCl(TsDPEN)(p-cymene)], to obtain the title compound (5.5 g, 89%). $^1$H NMR (400 MHz, CDCl$_3$) δ 1.94-1.95 (m, 1H), 2.04-2.13 (m, 1H), 2.17-2.18 (m, 1H), 2.35-2.37 (m, 1H), 2.71-2.79 (m, 1H), 2.88-2.98 (m, 1H), 4.07-4.09 (m, 1H), 4.66-4.71 (m, 1H), 7.07 (d, J=8.0, 1H), 7.20 (dd, J=10.2, 2.4, 1H), 7.47 (d, J=2.4, 1H).

PREPARATION EXAMPLE 36 ethyl 4-(3-chlorophenyl)butanoate

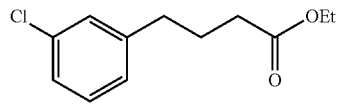 [SMILES: CCOC(=O)CCCc1cccc(Cl)c1]

To a stirred solution of diethyl malonate (6.92 g, 43.2 mmol) in THF (160 mL) was added NaH (1.73 g, 43.2 mmol, 60% in mineral oil) then heated to reflux. The mixture was added 3-chloropentyl bromide (7.9 g, 36.0 mmol) in THF (20 mL) then stirred for 2 h. The resulting mixture was cooled to room temperature, quenched with water, extracted with EtOAc, washed with water, dried over MgSO$_4$, filtered and concentrated. The crude product was dissolved in DMSO (70 mL). The mixture was added NaCl (1.32 g, 22.66 mmol) and water (0.82 g, 45.32 mmol) then heated to reflux. The mixture was stirred for 8 h. The resulting mixture was cooled to room temperature, quenched with water, extracted with EtOAc, washed with water, dried over MgSO$_4$, filtered and concentrated under reduced pressure. The crude product was purified by silica gel column chromatography to produce the title compound (2.87 g, 59%). $^1$H NMR (400 MHz, CDCl$_3$) δ 1.26 (t, J=7.2, 3H), 1.94-1.96 (m, 2H), 2.31 (t, J=7.6, 2H), 2.63 (t, J=7.6, 2H), 4.12 (q, J=7.2, 2H), 7.05 (d, J=6.8, 1H), 7.15-7.23 (m, 3H).

PREPARATION EXAMPLE 37

6-chloro-3,4-dihydronaphthalen-1(2H)-one

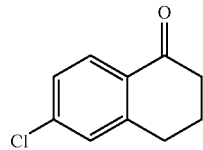 [SMILES: O=C1CCCc2cc(Cl)ccc21]

To a solution of ethyl 4-(3-chlorophenyl)butanoate (Preparation example 36, 2.87 g, 13.5 mmol) in H$_2$SO$_4$ (53.9 mL) and water (17.4 mL) was heated to reflux. The mixture was stirred for 6 h. The resulting mixture was cooled to room temperature, quenched with water, extracted with EtOAc, washed with water, dried over MgSO$_4$, filtered and concentrated under reduced pressure. The crude product was purified by silica gel column chromatography to produce the title compound (1.46 g, 60%). $^1$H NMR (400 MHz, CDCl$_3$) δ 2.12-2.19 (m, 2H), 2.67 (t, J=6.4, 2H), 2.96 (t, J=6.4, 2H), 7.28-7.30 (m, 2H), 7.98 (d, J=8.4, 1H).

PREPARATION EXAMPLE 38

6-chloro-1-oxo-1,2,3,4-tetrahydronaphthalen-2-yl acetate

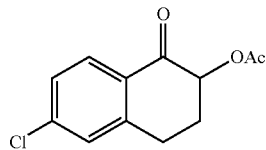 [SMILES: CC(=O)OC1CCc2cc(Cl)ccc2C1=O]

The substantially same method as described in Preparation example 5 was conducted, except that 6-chloro-3,4-dihydronaphthalen-1(2H)-one (Preparation example 37), was used instead of 8-chloro-3,4-dihydronaphthalen-1(2H)-one (Preparation example 4), to obtain the title compound (1.48 g, 45%). $^1$H NMR (400 MHz, CDCl$_3$) δ 2.23 (s, 3H), 2.28-2.33 (m, 1H), 2.37-2.43 (m, 1H), 3.03-3.09 (m, 1H), 3.15-3.23 (m, 1H), 5.53 (dd, J=5.2, 23.4, 1H), 7.27-7.32 (m, 2H), 7.96 (d, J=8.4, 1H).

PREPARATION EXAMPLE 39

(1S,2R)-6-chloro-1,2,3,4-tetrahydronaphthalene-1,2-diol

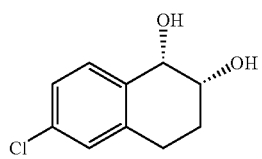 [SMILES: O[C@@H]1CCc2cc(Cl)ccc2[C@@H]1O]

The substantially same method as described in Preparation example 11 was conducted, except that 6-chloro-1-oxo-1,2,3,4-tetrahydronaphthalen-2-yl acetate (Preparation example 38), was used instead of 7-chloro-1-oxo-2,3-dihydro-1H-inden-2-yl acetate (Preparation example 10), to obtain the title compound (0.52 g, 88%). $^1$H NMR (400 MHz, CDCl$_3$) δ 1.92-1.96 (m, 1H), 2.01-2.10 (m, 1H), 2.19 (d, J=6.4, 1H), 2.29 (d, J=6.4, 1H), 2.72-2.80 (m, 1H), 2.92-2.99 (m, 1H), 4.04 (ddd, J=3.6, 8.0, 12.0, 1H), 4.68 (dd, J=4.0, 4.0, 1H), 7.13 (d, J=2.0, 1H), 7.20 (dd, J=2.0, 8.0, 1H), 7.39 (d, J=8.0, 1H).

PREPARATION EXAMPLE 40

(1R,2S)-6-chloro-1,2,3,4-tetrahydronaphthalene-1,2-diol

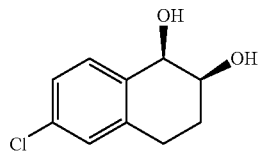 [SMILES: O[C@@H]1c2ccc(Cl)cc2CC[C@@H]1O]

The substantially same method as described in Preparation example 11 was conducted, except that 6-chloro-1-oxo-1,2,3,4-tetrahydronaphthalen-2-yl acetate (Preparation example 38) and (R,R)-[RuCl(TsDPEN)(p-cymene)], was used instead of 7-chloro-1-oxo-2,3-dihydro-1H-inden-2-yl acetate (Preparation example 10) and (S,S)-[RuCl(TsDPEN)(p-cymene)], to obtain the title compound (0.44 g, 75%). $^1$H NMR (400 MHz, CDCl$_3$) δ 1.92-1.96 (m, 1H), 2.01-2.10 (m, 1H), 2.19 (d, J=6.4, 1H), 2.29 (d, J=6.4, 1H), 2.72-2.80 (m, 1H), 2.92-2.99 (m, 1H), 4.04 (ddd, J=3.6, 8.0, 12.0, 1H), 4.68 (dd, J=4.0, 4.0, 1H), 7.13 (d, J=2.0, 1H), 7.20 (dd, J=2.0, 8.0, 1H), 7.39 (d, J=8.0, 1H).

PREPARATION EXAMPLE 41

8-fluoro-3,4-dihydronaphthalen-1(2H)-one

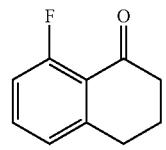

8-amino-3,4-dihydronaphthalen-1(2H)-one (Preparation example 3, 1.24 g, 7.7 mmol) in acetone (20mL) was added to a mixture of NOBF$_4$ (1.18 g, 10.2 mmol) in acetone (20mL) at −20° C. After 1 h, more NOBF$_4$ (1.34 g, 11.5 mmol) was added to the mixture. After 1 h, the resulting mixture was poured into CHCl$_3$ and stirred for 30 min. The mixture was dried over MgSO$_4$ and the solvent was removed under vacuum. The solids were added portionwise to a solution of toluene at reflux. Heating was continued for 15 min. The resulting mixture was cooled to room temperature and filtered through celite. The crude product was purified by silica gel column chromatography to produce the title compound (0.26 g, 41%). $^1$H NMR (400 MHz, CDCl$_3$) δ

2.13-2.05 (m, 2H), 2.63 (t, J=6.3, 2H), 2.95 (t, J=5.7, 2H), 6.96 (dd, J=8.7, 11.4, 1H), 7.03 (d, J=7.5, 1H), 7.39 (dt, J=4.8, 7.8, 1H)

PREPARATION EXAMPLE 42

8-fluoro-1-oxo-1,2,3,4-tetrahydronaphthalen-2-yl acetate

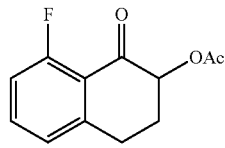

The substantially same method as described in Preparation example 5 was conducted, except that 8-fluoro-3,4-dihydronaphthalen-1(2H)-one (Preparation example 41), was used instead of 8-chloro-3,4-dihydronaphthalen-1(2H)-one (Preparation example 4), to obtain the title compound (10.9 g, 62%). $^1$H NMR (400 MHz, CDCl$_3$) δ 2.09 (s, 3H), 2.16-2.27 (m, 2H), 2.72-2.77 (m, 2H), 6.28 (dd, J=2.4, 10.2, 1H), 7.24 (dd, J=1.0, 7.7, 1H), 7.38 (dd, J=1.0, 8.3, 1H), 7.59 (dd, J=7.7, 8.3, 1H)

PREPARATION EXAMPLE 43

(1S,2R)-8-fluoro-1,2,3,4-tetrahydronaphthalene-1,2-diol

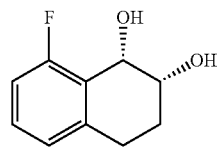 [SMILES: O[C@@H]1CCc2cccc(F)c2[C@@H]1O]

The substantially same method as described in Preparation example 11 was conducted, except that 8-fluoro-1-oxo-1,2,3,4-tetrahydronaphthalen-2-yl acetate (Preparation example 42), was used instead of 7-chloro-1-oxo-2,3-dihydro-1H-inden-2-yl acetate (Preparation example 10), to obtain the title compound (0.11 g, 45%). $^1$H NMR (400 MHz, CDCl$_3$) δ 2.08 (br s, 2H), 3.01-3.04 (m, 4H), 4.10-4.13 (m, 2H), 6.84 (t, J=7.7, 1H), 7.10 (d, J=7.5, 1H), 7.71 (d, J=7.7, 1H)

PREPARATION EXAMPLE 44

(1R,2S)-8-fluoro-1,2,3,4-tetrahydronaphthalene-1,2-diol

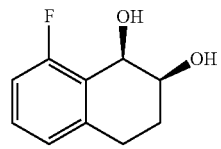 [SMILES: O[C@@H]1c2c(F)cccc2CC[C@@H]1O]

The substantially same method as described in Preparation example 11 was conducted, except that 8-fluoro-1-oxo-1,2,3,4-tetrahydronaphthalen-2-yl acetate (Preparation example 42) and (R,R)-[RuCl(TsDPEN)(p-cymene)], was used instead of 7-chloro-1-oxo-2,3-dihydro-1H-inden-2-yl acetate (Preparation example 10) and (S,S)-[RuCl(TsDPEN)(p-cymene)], to obtain the title compound (0.25 g, 45%). $^1$H NMR (400 MHz, CDCl$_3$) δ 2.08 (br s, 2H), 3.01-3.04 (m, 4H), 4.10-4.13 (m, 2H), 6.84 (t, J=7.7, 1H), 7.10 (d, J=7.5, 1H), 7.71 (d, J=7.7, 1H)

PREPARATION EXAMPLE 45

8-iodo-3,4-dihydronaphthalen-1(2H)-one

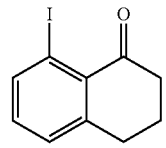 [SMILES: O=C1CCCc2cccc(I)c21]

To a stirred solution of 8-amino-3,4-dihydronaphthalen-1(2H)-one (Preparation example 3, 37.2 g, 231.0 mmol) in 32% aq. H$_2$SO$_4$ was added sodium nitrate (16.4 g, 238.0 mmol) and potassium iodide (57.5 g, 346.5 mmol) at 0° C. The mixture was stirred for 7 h. The reaction mixture was quenched with H$_2$O then extracted with EtOAc. The aqueous layer was extracted with EtOAc and separated. The combined organic layer was washed with sat. NaHCO$_3$ and H$_2$O, then dried over MgSO$_4$ and evaporated under reduced pressure and silicagel column isolation with EtOAc/n-hexanes to give product as a white solid (32.6 g, 52%). $^1$H NMR (400 MHz, CDCl$_3$) δ 2.13 (qt, J=6.4, 2H), 2.73 (t, J=6.4, 2H), 3.0 (t, J=6.4, 2H), 7.05 (t, J=7.6, 1H), 7.16 (dd, J=7.6, 0.8, 1H), 7.97 (d, J=8.0, 1H).

PREPARATION EXAMPLE 46

2-hydroxy-8-iodo-3,4-dihydronaphthalen-1(2H)-one

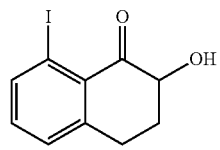 [SMILES: O=C1c2c(I)cccc2CCC1O]

The substantially same method as described in Preparation example 9 was conducted, except that 8-iodo-3,4-dihydronaphthalen-1(2H)-one (Preparation example 45), was used instead of 7-chloro-2,3-dihydro-1H-indan-1-one (Preparation example 8), to obtain the title compound (10.1 g, 65.0%). $^1$H NMR (400 MHz, CDCl$_3$) δ 1.98-2.09 (m, 1H), 2.52-2.58 (m, 1H), 3.04-3.11 (m, 1H), 3.17-3.26 (m, 1H), 4.02 (br s, 1H), 4.37-4.42 (m, 1H), 7.12 (t, J=8.0, 1H), 7.29 (d, J=6.8, 1H), 8.0 (d, J=7.6, 1H).

PREPARATION EXAMPLE 47

8-iodo-1-oxo-1,2,3,4-tetrahydronaphthalen-2-yl acetate

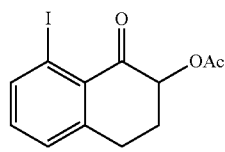 [SMILES: CC(=O)OC1CCc2cccc(I)c2C1=O]

The substantially same method as described in Preparation example 10 was conducted, except that 2-hydroxy-8-iodo-3,4-dihydronaphthalen-1(2H)-one (Preparation example 46), was used instead of 7-chloro-2-hydroxy-2,3-dihydro-1H-inden-1-one (Preparation example 9), to obtain the title compound (15.7 g, 78.0%). $^1$H NMR (400 MHz, CDCl$_3$) δ 2.24 (s, 3H), 2.27-2.34 (m, 1H), 2.37-2.45 (m, 1H), 3.10-3.17 (m, 1H), 3.22-3.30 (m, 1H), 5.50 (dd, J=13.2, 5.2, 1H), 7.09 (t, J=8.0, 1H), 7.26 (d, J=6.8, 1H), 7.99 (d, J=8.0, 1H).

PREPARATION EXAMPLE 48

(1S,2R)-8-iodo-1,2,3,4-tetrahydronaphthalene-1,2-diol

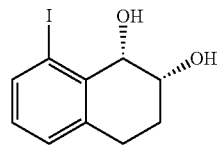 [SMILES: O[C@@H]1CCc2cccc(I)c2[C@@H]1O]

The substantially same method as described in Preparation example 11 was conducted, except that 8-iodo-1-oxo-1,2,3,4-tetrahydronaphthalen-2-yl acetate (Preparation example 47), was used instead of 7-chloro-1-oxo-2,3-dihydro-1H-inden-2-yl acetate (Preparation example 10), to obtain the title compound (3.8 g, 85%). $^1$H NMR (400 MHz, CDCl$_3$) δ 1.92-1.94 (m, 1H), 1.95-2.08 (m, 1H), 2.57 (d, J=8.8, 1H), 2.64 (d, J=4.4, 1H), 2.81-2.96 (m, 2H), 3.86-3.93 (m, 1H), 4.85 (t, J=3.2, 1H), 6.96 (t, J=7.6, 1H), 7.20 (d, J=7.6, 1H), 7.47 (d, J=8.0, 1H).

PREPARATION EXAMPLE 49

(1R,2S)-8-iodo-1,2,3,4-tetrahydronaphthalene-1,2-diol

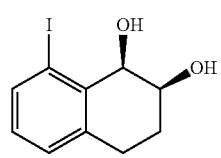 [SMILES: O[C@@H]1c2c(I)cccc2CC[C@@H]1O]

The substantially same method as described in Preparation example 11 was conducted, except that 8-iodo-1-oxo-1,2,3,4-tetrahydronaphthalen-2-yl acetate (Preparation example 47) and (R,R)-[RuCl(TsDPEN)(p-cymene)], was used instead of 7-chloro-1-oxo-2,3-dihydro-1H-inden-2-yl acetate (Preparation example 10) and (S,S)-[RuCl(TsDPEN)(p-cymene)], to obtain the title compound (4.4 g, 88%). $^1$H NMR (400 MHz, CDCl$_3$) δ 1.92-1.94 (m, 1H), 1.95-2.08 (m, 1H), 2.57 (d, J=8.8, 1H), 2.64 (d, J=4.4, 1H), 2.81-2.96 (m, 2H), 3.86-3.93 (m, 1H), 4.85 (t, J=3.2, 1H), 6.96 (t, J=7.6, 1H), 7.20 (d, J=7.6, 1H), 7.47 (d, J=8.0, 1H).

PREPARATION EXAMPLE 50

1-oxo-1,2,3,4-tetrahydronaphthalen-2-yl acetate

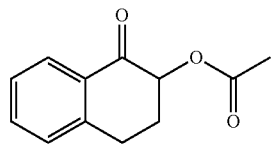

The substantially same method as described in Preparation example 5 was conducted, except that α-tetralone, was used instead of 8-chloro-3,4-dihydronaphthalen-1(2H)-one (Preparation example 4), to obtain the title compound (4.89 g, 70%). $^1$H NMR (400 MHz, CDCl$_3$) δ 2.23 (s, 3H), 2.39 (m, 2H), 3.21 (m, 2H), 5.56 (m, 1H), 7.28 (d, J=7.5, 1H), 7.33 (dd, J=7.5, 7.8, 1H), 7.51 (dd, J=7.5, 7.8, 1H), 8.03 (d, J=7.5, 1H)

PREPARATION EXAMPLE 51

(1S ,2R)-1,2,3,4-tetrahydronaphthalene-1,2-diol

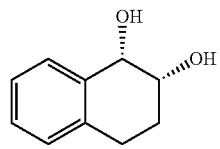 [SMILES: O[C@@H]1CCc2ccccc2[C@@H]1O]

The substantially same method as described in Preparation example 11 was conducted, except that 1-oxo-1,2,3,4-tetrahydronaphthalen-2-yl acetate (Preparation example 50), was used instead of 7-chloro-1-oxo-2,3-dihydro-1H-inden-2-yl acetate (Preparation example 10), to obtain the title compound (2.36 g, 60%). $^1$H NMR (400 MHz, CDCl$_3$) δ 1.91-2.10 (m, 1H), 2.12-2.24 (m, 1H), 2.69-2.86 (m, 1H), 2.98-3.04 (m, 1H), 3.82 (ddd, J=3.7, 8.0, 11.4, 1H), 4.72 (d, J=8.0, 1H), 7.11-7.45 (m, 4H)

PREPARATION EXAMPLE 52

(1R,2S)-1,2,3,4-tetrahydronaphthalene-1,2-diol

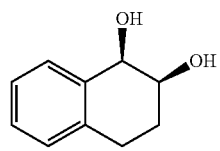 [SMILES: O[C@@H]1c2ccccc2CC[C@@H]1O]

The substantially same method as described in Preparation example 11 was conducted, except that 1-oxo-1,2,3,4-tetrahydronaphthalen-2-yl acetate (Preparation example 50) and (R,R)-[RuCl(TsDPEN)(p-cymene)], was used instead of 7-chloro-1-oxo-2,3-dihydro-1H-inden-2-yl acetate (Preparation example 10) and (S,S)-[RuCl(TsDPEN)(p-cymene)], to obtain the title compound (2.58 g, 62%). $^1$H NMR (400 MHz, CDCl$_3$) δ 1.91-2.10 (m, 1H), 2.12-2.24 (m, 1H), 2.69-2.86 (m, 1H), 2.98-3.04 (m, 1H), 3.82 (ddd, J=3.7, 8.0, 11.4, 1H), 4.72 (d, J=8.0, 1H), 7.11-7.45 (m, 4H)

PREPARATION EXAMPLE 53 tert-Butyl(7-chloro-3H-inden-1-yloxy)diphenylsilane

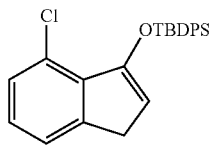

The substantially same method as described in Preparation example 24 was conducted, except that 7-chloro-2,3-dihydro-1H-inden-1-one (Preparation example 8), was used instead of 8-chloro-3,4-dihydronaphthalen-1(2H)-one (Preparation example 4), to obtain the title compound (4.64 g, 78%). $^1$H NMR (400 MHz, CDCl$_3$) δ 0.74 (s, 9H), 3.27 (d, 2H, J=2.53 Hz), 5.11 (dd, 1H, J=2.54, 2.54 Hz), 7.19-7.28 (m, 3H), 7.34-7.44 (m, 9H).

PREPARATION EXAMPLE 54

(1R,2R)-1-((tert-butyldiphenylsilyl)oxy)-7-chloro-2,3-dihydro-1H-inden-2-ol

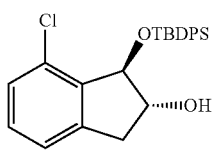

The substantially same method as described in Preparation example 25-26 was conducted, except that tert-Butyl (7-chloro-3H-inden-1-yloxy)diphenylsilane (Preparation example 53), was used instead of tert-butyl((8-chloro-3,4-dihydronaphthalen-1-yl)oxy)diphenylsilane (Preparation example 24), to obtain the title compound (1.68 g, 55%). $^1$H NMR (400 MHz, CDCl$_3$) δ 0.74 (s, 9H), 3.07-3.14 (m, 2H), 4.18-4.20 (m, 1H), 5.53 (d, 1H, J=6.58 Hz), 7.01-7.03 (m, 1H), 7.22-7.26 (m, 3H), 7.28-7.36 (m, 5H), 7.54-7.61 (m, 4H).

PREPARATION EXAMPLE 55

(1R,2R)-1-((tert-butyldiphenylsilyl)oxy)-7-chloro-2,3-dihydro-1H-inden-2-yl carbamate

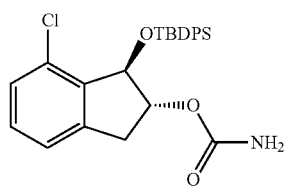

The substantially same method as described in Preparation example 27 was conducted, except that (1R,2R)-1-((tert-butyldiphenylsilyl)oxy)-7-chloro-2,3-dihydro-1H-inden-2-ol (Preparation example 54), was used instead of (1R,2R)-1-((tert-butyldiphenylsilyl)oxy)-8-chloro-1,2,3,4-tetrahydronaphthalen-2-ol (Preparation example 26), to obtain the title compound (1.54 g, 55%). $^1$H NMR (400 MHz, CDCl$_3$) δ 0.74 (s, 9H), 3.13-3.18 (m, 2H), 4.95-4.98 (m, 1H), 5.59 (d, 1H, J=6.57 Hz), 6.02 (br s, 2H), 6.29-6.31 (m, 1H), 7.22-7.25 (m, 3H), 7.29-7.38 (m, 5H), 7.44-7.53 (m, 4H).

PREPARATION EXAMPLE 56

(1S,2S)-1-((tert-butyldiphenylsilyl)oxy)-7-chloro-2,3-dihydro-1H-inden-2-ol

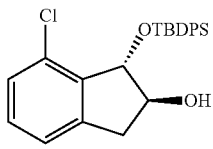

The substantially same method as described in Preparation example 25-26 was conducted, except that tert-Butyl (7-chloro-3H-inden-1-yloxy)diphenylsilane (Preparation example 53) and L-Fructose-derived Shi catalyst, was used instead of tert-butyl((8-chloro-3,4-dihydronaphthalen-1-yl)oxy)diphenylsilane (Preparation example 24) and D-Fructose-derived Shi catalyst, to obtain the title compound (1.44 g, 51%). $^1$H NMR (400 MHz, CDCl$_3$) δ 0.74 (s, 9H), 3.07-3.14 (m, 2H), 4.18-4.20 (m, 1H), 5.53 (d, 1H, J=6.58 Hz), 7.01-7.03 (m, 1H), 7.22-7.26 (m, 3H), 7.28-7.36 (m, 5H), 7.54-7.61 (m, 4H).

PREPARATION EXAMPLE 57

(1S,2S)-1-((tert-butyldiphenylsilyl)oxy)-7-chloro-2,3-dihydro-1H-inden-2-yl carbamate

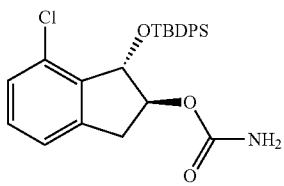

The substantially same method as described in Preparation example 27 was conducted, except that (1S,2S)-1-((tert-butyldiphenylsilyl)oxy)-7-chloro-2,3-dihydro-1H-inden-2-ol (Preparation example 56), was used instead of (1R,2R)-1-((tert-butyldiphenylsilyl)oxy)-8-chloro-1,2,3,4-tetrahydronaphthalen-2-ol (Preparation example 26), to obtain the title compound (1.31 g, 54%). $^1$H NMR (400 MHz, CDCl$_3$) δ 0.74 (s, 9H), 3.13-3.18 (m, 2H), 4.95-4.98 (m, 1H), 5.59 (d, 1H, J =6.57 Hz), 6.02 (br s, 2H), 6.29-6.31 (m, 1H), 7.22-7.25 (m, 3H), 7.29-7.38 (m, 5H), 7.44-7.53 (m, 4H).

PREPARATION EXAMPLE 58

7-fluoro-2,3-dihydro-1H-inden-1-one

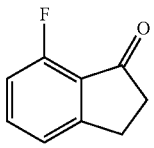

The substantially same method as described in Preparation example 8 was conducted, except that 2-fluorobenzoic acid, was used instead of 2-chlorobenzoic acid, to obtain the title compound (0.43 g, 27%). $^1$H NMR (400 MHz, CDCl$_3$) δ 2.67-2.80 (m, 2H), 3.20 (t, J=5.9, 2H), 7.00 (t, J=8.5, 1H), 7.30 (d, J=7.6, 1H), 7.60 (m, 1H).

PREPARATION EXAMPLE 59

7-fluoro-1-oxo-2,3-dihydro-1H-inden-2-yl acetate

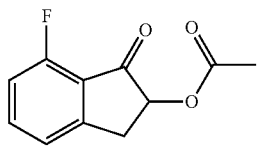

The substantially same method as described in Preparation example 5 was conducted, except that 7-fluoro-2,3-dihydro-1H-inden-1-one (Preparation example 58), was used instead of 8-chloro-3,4-dihydronaphthalen-1(2H)-one (Preparation example 4), to obtain the title compound (1.01 g, 80%). $^1$H NMR (400 MHz, CDCl$_3$) δ 2.22 (s, 3H), 3.09 (dd, J=5.2, 17.2, 1H), 3.68 (dd, J=8.0, 17.2, 1H), 5.38-5.46 (m, 1H), 6.99-7.10 (m, 1H), 7.25-7.27 (m, 1H), 7.64-7.69 (m, 1H)

PREPARATION EXAMPLE 60

(1S,2R)-7-fluoro-2,3-dihydro-1H-indene-1,2-diol

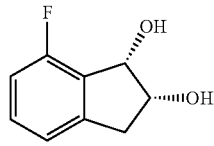

The substantially same method as described in Preparation example 11 was conducted, except that 7-fluoro-1-oxo-2,3-dihydro-1H-inden-2-yl acetate (Preparation example 59), was used instead of 7-chloro-1-oxo-2,3-dihydro-1H-inden-2-yl acetate (Preparation example 10), to obtain the title compound (0.33 g, 61%). $^1$H NMR (400 MHz, CDCl$_3$) δ 2.60 (d, J=4.8, 1H), 2.75 (d, J=6.4, 1H), 3.02 (dd, J=5.4, 16.2, 1H), 3.18 (dd, J=6.2, 16.2, 1H), 4.51-4.57 (m, 1H), 5.26 (t, J=5.2, 1H), 6.92-6.97 (m, 1H), 7.01-7.06 (m, 1H), 7.23-7.32 (m, 1H).

PREPARATION EXAMPLE 61

(1R,2S)-7-fluoro-2,3-dihydro-1H-indene-1,2-diol

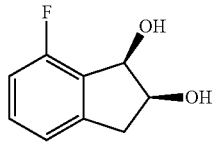 [SMILES: O[C@@H]1c2c(F)cccc2C[C@@H]1O]

The substantially same method as described in Preparation example 11 was conducted, except that 7-fluoro-1-oxo-2,3-dihydro-1H-inden-2-yl acetate (Preparation example 59) and (R,R)-[RuCl(TsDPEN)(p-cymene)], was used instead of 7-chloro-1-oxo-2,3-dihydro-1H-inden-2-yl acetate (Preparation example 10) and (S,S)-[RuCl(TsDPEN)(p-cymene)], to obtain the title compound (0.24 g, 59%). $^1$H NMR (400 MHz, CDCl$_3$) δ 2.60 (d, J=4.8, 1H), 2.75 (d, J=6.4, 1H), 3.02 (dd, J=5.4, 16.2, 1H), 3.18 (dd, J=6.2, 16.2, 1H), 4.51-4.57 (m, 1H), 5.26 (t, J=5.2, 1H), 6.92-6.97 (m, 1H), 7.01-7.06 (m, 1H), 7.23-7.32 (m, 1H).

PREPARATION EXAMPLE 62

6-chloro-2,3-dihydro-1H-inden-1-one

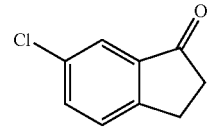 [SMILES: O=C1CCc2ccc(Cl)cc21]

To a stirred solution of 4-chlorocinnamic acid (1.0 g, 5.46 mmol) in EtOAc (20 mL) was added Pd on carbon (0.12 g, 0.11 mmol) at room temperature under H$_2$ atmosphere. The mixture was stirred for 10 h. The resulting mixture was filtered through celite and the solvent of the filtrate was removed in vacuo. The concentrated product was employed without further purification in the next reaction. Oxalyl chloride (0.96 mL, 10.92 mmol) was cautiously added to a solution of the 3-(4-chlorophenyl)propanoic acid in CH$_2$Cl$_2$ (20 mL). The mixture was stirred for 8 h and then the solvent was removed vacuo. The appropriate acid chloride was employed without further workup in the next reaction step. To a stirred solution of acid chloride in CH$_2$Cl$_2$ (20 mL) was added portionwise AlCl$_3$ (0.82 g, 6.22 mmol) at room temperature and heated under reflux for 6 h. The resulting mixture was poured into ice-water and the aq. phase was extracted with CH$_2$Cl$_2$, washed with 1N aq. NaOH and brine, dried over MgSO$_4$, filtered and concentrated under reduced pressure. The crude product was purified by silica gel column chromatography to produce the title compound (0.59 g, 66%). $^1$H NMR (400 MHz, CDCl$_3$) δ 2.64-2.78 (m, 2H), 3.04-3.17 (m, 2H), 7.41 (d, J=7.9, 1H), 7.55 (dd, J=8.2, 1H), 7.65-7.75 (m, 1H).

PREPARATION EXAMPLE 63

6-chloro-1-oxo-2,3-dihydro-1H-inden-2-yl acetate

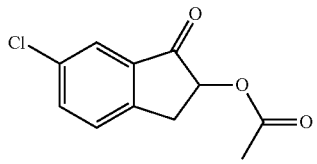

The substantially same method as described in Preparation example 5 was conducted, except that 6-chloro-2,3-dihydro-1H-inden-1-one (Preparation example 62), was used instead of 8-chloro-3,4-dihydronaphthalen-1(2H)-one (Preparation example 4), to obtain the title compound (3.29 g, 80%). $^1$H NMR (400 MHz, CDCl$_3$) δ 2.06 (s, 3H), 3.37 (dd, J=4.1, 15.6, 1H), 3.41 (dd, J=8.1, 15.7, 1H), 6.27 (dd, J=4.1, 8.1, 1H), 7.02 (dd, J=1.3, 7.8, 1H), 7.56 (dd, J=1.7, 7.8, 1H), 8.18 (dd, J=1.3, 1.7, 1H).

PREPARATION EXAMPLE 64

(1S,2R)-6-chloro-2,3-dihydro-1H-indene-1,2-diol

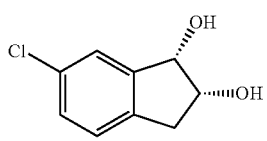 [SMILES: O[C@@H]1Cc2ccc(Cl)cc2[C@@H]1O]

The substantially same method as described in Preparation example 11 was conducted, except that 6-chloro-1-oxo-2,3-dihydro-1H-inden-2-yl acetate (Preparation example 63), was used instead of 7-chloro-1-oxo-2,3-dihydro-1H-inden-2-yl acetate (Preparation example 10), to obtain the title compound (0.74 g, 23%). $^1$H NMR (400 MHz, CDCl$_3$) δ 2.94 (dd, J=8.1, 15.8, 1H), 3.00 (dd, J=6.6, 15.8, 1H), 4.28-4.32 (m, 1H), 4.95 (d, J=8.0, 1H), 7.23 (dd, J=1.6, 7.8, 1H), 7.28 (dd, J=1.6, 5.1, 1H), 7.35 (dd, J=1.6, 5.1, 1H).

PREPARATION EXAMPLE 65

(1R,2S)-6-chloro-2,3-dihydro-1H-indene-1,2-diol

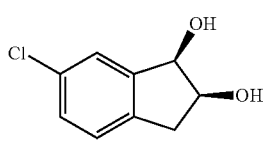 [SMILES: O[C@@H]1c2cc(Cl)ccc2C[C@@H]1O]

The substantially same method as described in Preparation example 11 was conducted, except that 6-chloro-1-oxo-2,3-dihydro-1H-inden-2-yl acetate (Preparation example 63) and (R,R)-[RuCl(TsDPEN)(p-cymene)], was used instead of 7-chloro-1-oxo-2,3-dihydro-1H-inden-2-yl acetate (Preparation example 10) and (S,S)-[RuCl(TsDPEN)(p-cymene)], to obtain the title compound (0.78 g, 24%). $^1$H NMR (400 MHz, CDCl$_3$) δ 2.94 (dd, J=8.1, 15.8, 1H), 3.00 (dd, J=6.6, 15.8, 1H), 4.28-4.32 (m, 1H), 4.95 (d, J=8.0, 1H), 7.23 (dd, J=1.6, 7.8, 1H), 7.28 (dd, J=1.6, 5.1, 1H), 7.35 (dd, J=1.6, 5.1, 1H).

PREPARATION EXAMPLE 66

5,7-dichloro-2,3-dihydro-1H-inden-1-one

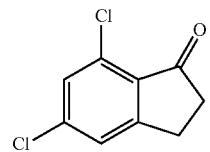 [SMILES: O=C1CCc2cc(Cl)cc(Cl)c21]

The substantially same method as described in Preparation example 8 was conducted, except that 2,4-dichlorobenzoic acid, was used instead of 2-chlorobenzoic acid, to obtain the title compound (0.86 g, 41%). $^1$H NMR (400 MHz, CDCl$_3$) δ 2.62 (t, 2H, J=7.5 Hz), 2.84 (t, 2H, J=7.5 Hz), 7.04 (m, 2H), 7.66 (s, 1H).

PREPARATION EXAMPLE 67

5,7-dichloro-1-oxo-2,3-dihydro-1H-inden-2-yl acetate

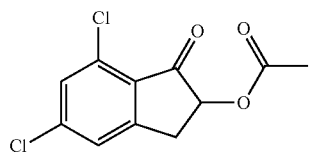 [SMILES: CC(=O)OC1Cc2cc(Cl)cc(Cl)c2C1=O]

The substantially same method as described in Preparation example 5 was conducted, except that 5,7-dichloro-2,3-dihydro-1H-inden-1-one (Preparation example 66), was used instead of 8-chloro-3,4-dihydronaphthalen-1(2H)-one (Preparation example 4), to obtain the title compound (1.38 g, 59%). $^1$H NMR (400 MHz, CDCl$_3$) δ 2.06 (s, 3H), 3.46 (dd, J=8.0, 15.5, 1H), 3.47 (dd, J=4.1, 15.5, 1H), 6.29 (dd, J=4.1, 8.0, 1H), 6.89 (d, J=1.6, 1H), 7.61-7.65 (m, 1H).

PREPARATION EXAMPLE 68

(1S,2R)-5,7-dichloro-2,3-dihydro-1H-indene-1,2-diol

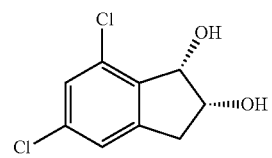 [SMILES: O[C@@H]1Cc2cc(Cl)cc(Cl)c2[C@@H]1O]

The substantially same method as described in Preparation example 11 was conducted, except that 5,7-dichloro-1-oxo-2,3-dihydro-1H-inden-2-yl acetate (Preparation example 67), was used instead of 7-chloro-1-oxo-2,3-dihydro-1H-inden-2-yl acetate (Preparation example 10), to obtain the title compound (1.02 g, 91%). $^1$H NMR (400

PREPARATION EXAMPLE 69

(1R,2S)-5,7-dichloro-2,3-dihydro-1H-indene-1,2-diol

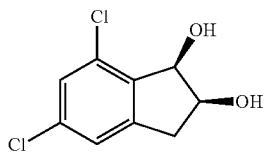

The substantially same method as described in Preparation example 11 was conducted, except that 5,7-dichloro-1-oxo-2,3-dihydro-1H-inden-2-yl acetate (Preparation example 67) and (R,R)-[RuCl(TsDPEN)(p-cymene)], was used instead of 7-chloro-1-oxo-2,3-dihydro-1H-inden-2-yl acetate (Preparation example 10) and (S,S)-[RuCl(TsDPEN)(p-cymene)], to obtain the title compound (0.95 g, 86%). $^1$H NMR (400 MHz, CDCl$_3$) δ 2.93 (dd, J=8.0, 15.8, 1H), 3.06 (dd, J=6.6, 15.8, 1H), 4.31-4.40 (m, 1H), 5.01 (d, J=8.0, 1H), 7.09 (d, J=1.6, 1H), 7.57 (d, J=1.6, 1H).

PREPARATION EXAMPLE 70

4-chloro-2,3-dihydro-1H-inden-1-one

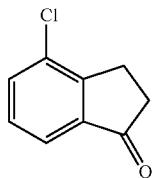

The substantially same method as described in Preparation example 62 was conducted, except that 2-chlorocinnamic acid, was used instead of 4-chlorocinnamic acid, to obtain the title compound (0.27 g, 60%). $^1$H NMR (400 MHz, CDCl$_3$) δ 2.70-2.78 (m, 2H), 3.10 (t, J=5.9, 2H), 7.31 (t, J=7.6, 1H), 7.58 (d, J=7.6, 1H), 7.63 (d, J=7.6, 1H).

PREPARATION EXAMPLE 71

4-chloro-1-oxo-2,3-dihydro-1H-inden-2-yl acetate

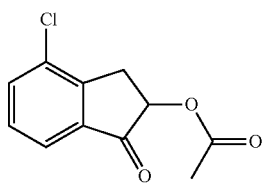

The substantially same method as described in Preparation example 5 was conducted, except that 4-chloro-2,3-dihydro-1H-inden-1-one (Preparation example 70), was used instead of 8-chloro-3,4-dihydronaphthalen-1(2H)-one (Preparation example 4), to obtain the title compound (1.68 g, 60%). $^1$H NMR (400 MHz, CDCl$_3$) δ 2.06 (s, 3H), 3.34 (dd, J=4.1, 15.7, 1H), 3.40 (dd, J=8.0, 15.7, 1H), 6.30 (dd, J=4.1, 8.1, 1H), 7.34 (dd, J=1.59, 7.79, 1H), 7.38 (dd, J=7.5, 7.9, 1H), 7.56 (dd, J=1.6, 7.5, 1H)

PREPARATION EXAMPLE 72

(1R,2S)-4-chloro-2,3-dihydro-1H-indene-1,2-diol

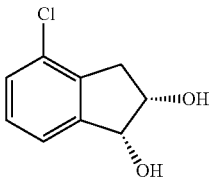 [SMILES: O[C@@H]1c2cccc(Cl)c2C[C@@H]1O]

The substantially same method as described in Preparation example 11 was conducted, except that 4-chloro-1-oxo-2,3-dihydro-1H-inden-2-yl acetate (Preparation example 71), was used instead of 7-chloro-1-oxo-2,3-dihydro-1H-inden-2-yl acetate (Preparation example 10), to obtain the title compound (1.02 g, 69%). $^1$H NMR (400 MHz, CDCl$_3$) δ 2.88 (dd, J=8.0, 15.8, 1H), 3.06 (dd, J=6.6, 15.8, 1H), 3.22 (dd, J=5.4, 16.2, 1H), 3.38 (dd, J=6.2, 16.2, 1H), 4.30-4.35 (m, 1H), 4.97 (d, J=8.0, 1H), 7.11 (dd, J=1.7, 8.0, 1H), 7.23 (dd, J=1.7, 7.7, 1H), 7.26 (dd, J=7.7, 8.0, 1H).

PREPARATION EXAMPLE 73

(1S,2R)-4-chloro-2,3-dihydro-1H-indene-1,2-diol

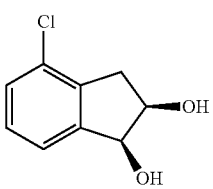

The substantially same method as described in Preparation example 11 was conducted, except that 4-chloro-1-oxo-2,3-dihydro-1H-inden-2-yl acetate (Preparation example 71) and (R,R)-[RuCl(TsDPEN)(p-cymene)], was used instead of 7-chloro-1-oxo-2,3-dihydro-1H-inden-2-yl acetate (Preparation example 10) and (S,S)-[RuCl(TsDPEN)(p-cymene)], to obtain the title compound (1.15 g, 68%). $^1$H NMR (400 MHz, CDCl$_3$) δ 2.88 (dd, J=8.0, 15.8, 1H), 3.06 (dd, J=6.6, 15.8, 1H), 3.22 (dd, J=5.4, 16.2, 1H), 3.38 (dd, J=6.2, 16.2, 1H), 4.30-4.35 (m, 1H), 4.97 (d, J=8.0, 1H), 7.11 (dd, J=1.7, 8.0, 1H), 7.23 (dd, J=1.7, 7.7, 1H), 7.26 (dd, J=7.7, 8.0, 1H).

PREPARATION EXAMPLE 74

(1S,2R)-2-((tert-butyldimethylsilyl)oxy)-8-chloro-1,2,3,4-tetrahydronaphthalen-1-ol

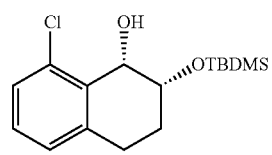 [SMILES: CC(C)(C)[Si](C)(C)O[C@@H]1CCc2cccc(Cl)c2[C@@H]1O]

To a stirred solution of (1S, 2R)-8-chloro-1,2,3,4-tetrahydronaphthalen-1,2-diol (Preparation example 6, 10.6 g, 53.36 mmol) in dichloromethane (530 mL) was added triethylamine (8.2 mL, 58.67 mmol) at −78° C. The mixture was stirred for 15 min and then dropwise added tert-butyldimethylsilyl trifluoromethanesulfonate (12.3 mL, 53.36 mmol) at −78° C. The reaction mixture was stirred for 0.5 h at −78° C. to 0° C. The resulting mixture was quenched with water 0° C. and then aqueous layer was extracted with dichloromethane. Combined organic layer was washed with water, dried over MgSO$_4$, filtered and concentrated under reduced pressure. The crude product was purified by silica gel column chromatography to produce the title compound (13.0 g, yield 78%). $^1$H NMR (400 MHz, CDCl$_3$) δ 0.16 (d, J=4.0 Hz, 6H), 0.96 (s, 9H), 1.74-1.78 (m, 1H), 2.04-2.19 (m, 1H), 2.77-2.85 (m, 1H), 2.91-2.98 (m, 2H), 3.93 (td, J=12.0, 3.8 Hz, 1H), 4.90 (d, J=3.6 Hz, 1H), 7.02-7.04 (m, 1H), 7.16 (t, J=7.6 Hz, 1H), 7.25-7.27 (m, 1H).

PREPARATION EXAMPLE 75 tert-butyl(((1S,2R)-8-chloro-1-methoxy-1,2,3,4-tetrahydronaphthalen-2-yl)oxy)dimethylsilane

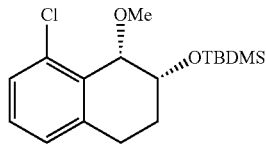 [SMILES: CO[C@H]1c2c(Cl)cccc2CC[C@H]1O[Si](C)(C)C(C)(C)C]

To a stirred solution of (1S,2R)-2-((tert-butyldimethylsilyl)oxy)-8-chloro-1,2,3,4-tetrahydronaphthalen-1-ol (Preparation example 74, 3.0 g, 9.59 mmol) in THF (30 mL) was portionwise added potassium tert-butoxide (1.6 g, 14.38 mmol) at 0° C. then allowed to stir for 10 min. The mixture was added CH$_3$I (3.0 mL, 47.94 mmol) at 0° C. When the reaction was completed, the resulting mixture was diluted with EtOAc, washed with water, dried over Na$_2$SO$_4$, filtered, and concentrated under reduced pressure to produce the title compound (3.1 g, yield 95%). $^1$H NMR (400 MHz, CDCl$_3$) δ 0.16 (d, J=4.0 Hz, 6H), 0.96 (s, 9H), 1.76-1.80 (m, 1H), 2.22-2.33 (m, 1H), 2.75-2.84 (m, 1H), 2.93-3.00 (m, 1H), 3.78 (s, 3H), 3.91-3.96 (m, 1H), 4.55-4.56 (m, 1H), 7.00-7.02 (m, 1H), 7.11-7.15 (m, 1H), 7.23-7.26 (m, 1H).

PREPARATION EXAMPLE 76

(1S,2R)-8-chloro-1-methoxy-1,2,3,4-tetrahydronaphthalen-2-ol

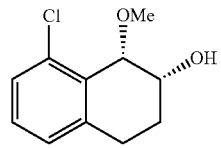 [SMILES: CO[C@H]1c2c(Cl)cccc2CC[C@H]1O]

To a stirred solution of tert-butyl(((1S,2R)-8-chloro-1-methoxy-1,2,3,4-tetrahydronaphthalen-2-yl)oxy)dimethylsilane (Preparation example 75, 3.2 g, 9.79 mmol) in THF (98 mL) was dropwise added TBAF (1 M solution, 11.8 mL, 11.80 mmol) at room temperature. When the reaction was completed, the resulting mixture was diluted with EtOAc, washed with sat. NaHCO$_3$ and brine, dried over Na$_2$SO$_4$, filtered, and concentrated under reduced pressure to produce the title compound (2.0 g, yield 94%). $^1$H NMR (400 MHz, CDCl$_3$) δ 1.92-1.95 (m, 1H), 2.04-2.15 (m, 1H), 2.34 (d, J=8.8 Hz, 1H), 2.74-2.83 (m, 1H), 3.00-3.07 (m, 1H), 3.65 (s, 3H), 3.88-3.95 (m, 1H), 4.74 (d, J=3.2 Hz, 1H), 7.03-7.05 (m, 1H), 7.14-7.18 (m, 1H), 7.25-7.27 (m, 1H).

PREPARATION EXAMPLE 77 tert-butyl(((1S,2R)-8-chloro-1-(methoxymethoxy)-1,2,3,4-tetrahydronaphthalen-2-yl)oxy)dimethylsilane

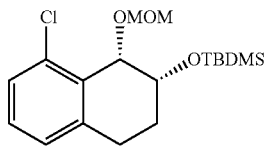

To a stirred solution of (1S,2R)-2-((tert-butyldimethylsilyl)oxy)-8-chloro-1,2,3,4-tetrahydronaphthalen-1-ol (Preparation example 74, 3.0 g, 9.59 mmol) in dichloromethane (48 mL) was added diisopropylethylamine (8.4 mL, 47.94 mmol) at 0° C. then allowed to stir for 20 min The mixture was added chloromethyl methyl ether (3.6 mL, 47.94 mmol) 0° C. When the reaction was completed, the resulting mixture was quenched with water, diluted with EtOAc, washed with water and brine, dried over MgSO$_4$, filtered and concentrated under reduced pressure to obtain the title compound (3.3 g, yield 96%). $^1$H NMR (400 MHz, CDCl$_3$) δ 0.12 (d, J=8.8 Hz, 6H), 0.94 (s, 9H), 1.78-1.83 (m, 1H), 2.27-2.38 (m, 1H), 2.79-2.88 (m, 1H), 3.01-3.07 (m, 1H), 3.43 (s, 3H), 3.90-3.94 (m, 1H), 4.95-4.96 (m, 1H), 5.00 (q, J=7.5 Hz, 2H), 7.03 (dd, J=7.6, 0.4 Hz, 1H), 7.15 (t, J=7.8 Hz, 1H), 7.24 (dd, J=7.6, 0.4 Hz, 1H).

PREPARATION EXAMPLE 78

(1S,2R)-8-chloro-1-(methoxymethoxy)-1,2,3,4-tetrahydronaphthalen-2-ol

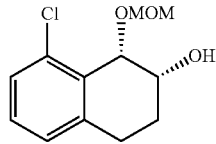

To a stirred solution of tert-butyl(((1S,2R)-8-chloro-1-(methoxymethoxy)-1,2,3,4-tetrahydronaphthalen-2-yl)oxy)dimethylsilane (Preparation example 77, 3.3 g, 9.24 mmol) in THF (92 mL) was dropwise added TBAF (1 M solution, 11.0 mL, 11.10 mmol) at room temperature. When the reaction was completed, the resulting mixture was diluted with EtOAc, washed with sat. NaHCO$_3$ and brine, dried over Na$_2$SO$_4$, filtered, and concentrated under reduced pressure to produce the title compound (2.2 g, yield 100%). $^1$H NMR (400 MHz, CDCl$_3$) δ 1.93-1.96 (m, 1H), 1.97-2.09 (m, 1H), 2.83-2.92 (m, 1H), 2.96-3.02 (m, 1H), 3.49 (s, 3H), 3.73-3.81 (m, 1H), 4.37 (d, J=10.4 Hz, 1H), 4.84 (d, J=7.2 Hz, 1H), 4.88-4.89 (m, 1H), 5.05 (d, J=7.2 Hz, 1H), 7.05-7.07 (m, 1H), 7.18 (t, J=7.8 Hz, 1H), 7.26-7.28 (m, 1H).

PREPARATION EXAMPLE 79

(1S,2R)-2-((tert-butyldimethylsilyl)oxy)-8-chloro-1,2,3,4-tetrahydronaphthalen-1-yl isopropylcarbamate

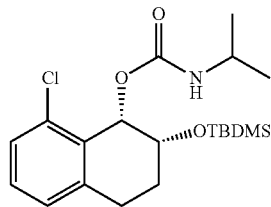 [SMILES: CC(C)NC(=O)O[C@H]1c2c(Cl)cccc2CC[C@H]1O[Si](C)(C)C(C)(C)C]

To a stirred solution of (1S,2R)-2-((tert-butyldimethylsilyl)oxy)-8-chloro-1,2,3,4-tetrahydronaphthalen-1-ol (Preparation example 74, 2.5 g, 7.83 mmol) in THF (39 mL) was added 1,1'-carbonyldiimidazole (2.5 g, 15.66 mmol) at room temperature for 14 hr. The mixture was added isopropylamine (6.1 mL, 68.80 mmol) then the mixture was stirred at room temperature for 14 hr. The resulting mixture was diluted with EtOAc, washed with water, dried over $MgSO_4$, and evaporated under reduced pressure to obtain the title compound (2.6 g, yield 95%). $^1$H NMR (400 MHz, $CDCl_3$) δ 0.16 (d, J=10.8 Hz, 6H), 0.92 (s, 9H), 0.14 (d, J=6.4 Hz, 6H), 1.81-1.84 (m, 1H), 2.00-2.11 (m, 1H), 2.78-2.87 (m, 1H), 2.94-3.00 (m, 1H), 3.82-3.83 (m, 1H), 3.95 (td, J=12.0, 3.6 Hz, 1H), 4.44 (br s, 1H), 6.19 (d, J=2.8 Hz, 1H), 7.04 (d, J=7.6 Hz, 1H), 7.17 (t, J=7.6 Hz, 1H), 7.25 (d, J=7.2 Hz, 1H).

TABLE 1

| Ex. No. | X | Position | n | l | m | A | B | Chiral-1 | Chiral-2 |
|---|---|---|---|---|---|---|---|---|---|
| 1 | Cl | 8 | 1 | 0 | 2 | OH | $OCONH_2$ | S | R |
| 2 | Cl | 8 | 1 | 0 | 2 | OH | $OCONH_2$ | R | S |
| 3 | Cl | 8 | 1 | 0 | 2 | OH | $OCONH_2$ | syn-rac. | syn-rac. |
| 4 | Cl | 8 | 1 | 0 | 2 | OH | $OCONH_2$ | R | R |
| 5 | Cl | 8 | 1 | 0 | 2 | OH | $OCONH_2$ | S | S |
| 6 | Cl | 7 | 1 | 0 | 2 | OH | $OCONH_2$ | S | R |
| 7 | Cl | 7 | 1 | 0 | 2 | OH | $OCONH_2$ | R | S |
| 8 | Cl | 6 | 1 | 0 | 2 | OH | $OCONH_2$ | S | R |
| 9 | Cl | 6 | 1 | 0 | 2 | OH | $OCONH_2$ | R | S |
| 10 | F | 8 | 1 | 0 | 2 | OH | $OCONH_2$ | S | R |
| 11 | F | 8 | 1 | 0 | 2 | OH | $OCONH_2$ | R | S |
| 12 | I | 8 | 1 | 0 | 2 | OH | $OCONH_2$ | S | R |
| 13 | I | 8 | 1 | 0 | 2 | OH | $OCONH_2$ | R | S |
| 14 | H | — | — | 0 | 2 | OH | $OCONH_2$ | S | R |
| 15 | H | — | — | 0 | 2 | OH | $OCONH_2$ | R | S |
| 16 | H | — | — | 0 | 2 | $OCONH_2$ | OH | S | R |
| 17 | H | — | — | 0 | 2 | $OCONH_2$ | OH | R | S |
| 18 | Cl | 8 | 1 | 0 | 2 | $OCONH_2$ | OH | S | R |
| 19 | Cl | 8 | 1 | 0 | 2 | $OCONH_2$ | OH | R | S |
| 20 | Cl | 8 | 1 | 0 | 2 | $OCONH_2$ | OH | syn-rac. | syn-rac. |
| 21 | Cl | 7 | 1 | 0 | 2 | $OCONH_2$ | OH | S | R |
| 22 | Cl | 7 | 1 | 0 | 2 | $OCONH_2$ | OH | R | S |
| 23 | Cl | 6 | 1 | 0 | 2 | $OCONH_2$ | OH | S | R |
| 24 | Cl | 6 | 1 | 0 | 2 | $OCONH_2$ | OH | R | S |
| 25 | F | 8 | 1 | 0 | 2 | $OCONH_2$ | OH | S | R |
| 26 | F | 8 | 1 | 0 | 2 | $OCONH_2$ | OH | R | S |
| 27 | I | 8 | 1 | 0 | 2 | $OCONH_2$ | OH | S | R |
| 28 | I | 8 | 1 | 0 | 2 | $OCONH_2$ | OH | R | S |
| 29 | Cl | 8 | 1 | 0 | 2 | $OCONH_2$ | $OCONH_2$ | S | R |
| 30 | Cl | 8 | 1 | 0 | 2 | $OCONH_2$ | $OCONH_2$ | R | S |
| 31 | Cl | 8 | 1 | 0 | 2 | $OCONH_2$ | $OCONH_2$ | R | R |
| 32 | Cl | 7 | 1 | 0 | 2 | $OCONH_2$ | $OCONH_2$ | S | R |
| 33 | Cl | 6 | 1 | 0 | 2 | $OCONH_2$ | $OCONH_2$ | R | S |
| 34 | F | 8 | 1 | 0 | 2 | $OCONH_2$ | $OCONH_2$ | S | R |
| 35 | F | 8 | 1 | 0 | 2 | $OCONH_2$ | $OCONH_2$ | R | S |
| 36 | I | 8 | 1 | 0 | 2 | $OCONH_2$ | $OCONH_2$ | S | R |
| 37 | I | 8 | 1 | 0 | 2 | $OCONH_2$ | $OCONH_2$ | R | S |
| 38 | H | — | — | 0 | 2 | $OCONH_2$ | $OCONH_2$ | S | R |
| 39 | H | — | — | 0 | 2 | $OCONH_2$ | $OCONH_2$ | R | S |
| 40 | Cl | 8 | 1 | 0 | 2 | OMOM | $OCONH_2$ | S | R |
| 41 | Cl | 8 | 1 | 0 | 2 | OMOM | $OCONH_2$ | R | S |
| 42 | Cl | 8 | 1 | 0 | 2 | OMOM | $OCONH_2$ | R | R |
| 43 | F | 8 | 1 | 0 | 2 | OMOM | $OCONH_2$ | S | R |
| 44 | F | 8 | 1 | 0 | 2 | OMOM | $OCONH_2$ | R | S |
| 45 | Cl | 8 | 1 | 0 | 2 | $OCONH_2$ | OMOM | S | R |
| 46 | Cl | 8 | 1 | 0 | 2 | $OCONH_2$ | OMOM | R | S |
| 47 | F | 8 | 1 | 0 | 2 | $OCONH_2$ | OMOM | S | R |
| 48 | F | 8 | 1 | 0 | 2 | $OCONH_2$ | OMOM | R | S |
| 49 | I | 8 | 1 | 0 | 2 | $OCONH_2$ | OMOM | S | R |
| 50 | I | 8 | 1 | 0 | 2 | $OCONH_2$ | OMOM | R | S |
| 51 | Cl | 7 | 1 | 0 | 1 | OH | $OCONH_2$ | S | R |
| 52 | Cl | 7 | 1 | 0 | 1 | OH | $OCONH_2$ | R | S |
| 53 | Cl | 7 | 1 | 0 | 1 | OH | $OCONH_2$ | R | R |
| 54 | Cl | 7 | 1 | 0 | 1 | OH | $OCONH_2$ | S | S |
| 55 | F | 7 | 1 | 0 | 1 | OH | $OCONH_2$ | S | R |
| 56 | F | 7 | 1 | 0 | 1 | OH | $OCONH_2$ | R | S |
| 57 | Cl | 6 | 1 | 0 | 1 | OH | $OCONH_2$ | S | R |
| 58 | Cl | 6 | 1 | 0 | 1 | OH | $OCONH_2$ | R | S |
| 59 | Cl | 5, 7 | 2 | 0 | 1 | OH | $OCONH_2$ | S | R |
| 60 | Cl | 5, 7 | 2 | 0 | 1 | OH | $OCONH_2$ | R | S |
| 61 | Cl | 4 | 1 | 1 | 0 | OH | $OCONH_2$ | R | S |
| 62 | Cl | 4 | 1 | 1 | 0 | OH | $OCONH_2$ | S | R |
| 63 | Cl | 7 | 1 | 0 | 1 | $OCONH_2$ | OH | S | R |
| 64 | Cl | 7 | 1 | 0 | 1 | $OCONH_2$ | OH | R | S |
| 65 | Cl | 5, 7 | 1 | 0 | 1 | $OCONH_2$ | OH | S | R |
| 66 | Cl | 5, 7 | 1 | 0 | 1 | $OCONH_2$ | OH | R | S |
| 67 | Cl | 4 | 1 | 1 | 0 | $OCONH_2$ | OH | R | S |
| 68 | Cl | 4 | 1 | 1 | 0 | $OCONH_2$ | OH | S | R |
| 69 | F | 7 | 1 | 0 | 1 | $OCONH_2$ | OH | S | R |
| 70 | F | 7 | 1 | 0 | 1 | $OCONH_2$ | OH | R | S |
| 71 | Cl | 7 | 1 | 0 | 1 | OMOM | $OCONH_2$ | S | R |
| 72 | Cl | 7 | 1 | 0 | 1 | OMOM | $OCONH_2$ | R | S |
| 73 | F | 7 | 1 | 0 | 1 | OMOM | $OCONH_2$ | S | R |
| 74 | F | 7 | 1 | 0 | 1 | OMOM | $OCONH_2$ | R | S |
| 75 | Cl | 7 | 1 | 0 | 1 | $OCONH_2$ | OMOM | S | R |
| 76 | Cl | 7 | 1 | 0 | 1 | $OCONH_2$ | OMOM | R | S |
| 77 | Cl | 7 | 1 | 0 | 1 | $OCONH_2$ | $OCONH_2$ | S | R |
| 78 | Cl | 7 | 1 | 0 | 1 | $OCONH_2$ | $OCONH_2$ | R | S |
| 79 | Cl | 4 | 1 | 1 | 0 | $OCONH_2$ | $OCONH_2$ | R | S |
| 80 | Cl | 4 | 1 | 1 | 0 | $OCONH_2$ | $OCONH_2$ | S | R |
| 81 | Cl | 6 | 1 | 0 | 1 | $OCONH_2$ | $OCONH_2$ | S | R |
| 82 | Cl | 6 | 1 | 0 | 1 | $OCONH_2$ | $OCONH_2$ | R | S |
| 83 | Cl | 5, 7 | 2 | 0 | 1 | $OCONH_2$ | $OCONH_2$ | S | R |
| 84 | Cl | 5, 7 | 2 | 0 | 1 | $OCONH_2$ | $OCONH_2$ | R | S |
| 85 | F | 7 | 1 | 0 | 1 | $OCONH_2$ | $OCONH_2$ | S | R |
| 86 | F | 7 | 1 | 0 | 1 | $OCONH_2$ | $OCONH_2$ | R | S |
| 87 | Cl | 8 | 1 | 0 | 2 | OMe | $OCONH_2$ | S | R |
| 88 | Cl | 8 | 1 | 0 | 2 | OMe | OCONHisopropyl | S | R |
| 89 | Cl | 8 | 1 | 0 | 2 | OMOM | OCONHisopropyl | S | R |
| 90 | Cl | 8 | 1 | 0 | 2 | OH | OCONHisopropyl | S | R |
| 91 | Cl | 8 | 1 | 0 | 2 | OCONHisopropyl | OH | S | R |
| 92 | Cl | 8 | 1 | 0 | 2 | OCONHisopropyl | OMe | S | R |
| 93 | Cl | 8 | 1 | 0 | 2 | OCONHisopropyl | OMOM | S | R |

EXAMPLE 1

(1S, 2R)-8-chloro-1-hydroxy-1,2,3,4-tetrahydronaphthalen-2-yl carbamate

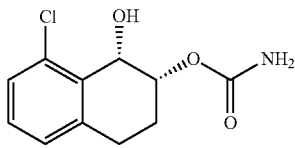 [SMILES: NC(=O)O[C@@H]1CCc2cccc(Cl)c2[C@@H]1O]

To a solution of (1S,2R)-8-chloro-1,2,3,4-tetrahydronaphthalene-1,2-diol (Preparation example 6, 3.57 g, 18.0 mmol) and 1,1'-carbonyldiimidazole (CDI, 7.29 g, 44.9 mmol) in THF was stirred at room temperature for 3 hr. The reaction mixture was diluted with EtOAc, and washed with 1N aq. HCl. The organic layer was dried over $MgSO_4$ and evaporated under reduced pressure. To a solution of the residue was added $NH_4OH$ (35 mL, 18.0 mmol). Then the mixture was stirred at room temperature for 6 hr. The reaction mixture was neutralized by 1N aq. HCl to pH 7, extracted with EtOAc. The combined organic layer was washed with water, dried over $MgSO_4$, and evaporated under reduced pressure. The concentrated residue was purified by a silica gel column chromatography, to obtain the title compound (1.88 g, 40-50%). mp 195-196; $^1$H NMR (400 MHz, $CDCl_3$) δ 1.99-2.03 (m, 1H), 2.24-2.33 (m, 1H), 2.35 (d, 1H, J=3.2 Hz), 2.92-3.06 (m, 2H), 4.78 (br s, 2H), 4.79 (td, 1H, J=3.6, 12.8 Hz), 5.26 (s, 1H), 7.09 (d, 1H, J=7.6 Hz), 7.21 (t, 1H, J=8.0 Hz), 7.29 (d, 1H, J=8.0 Hz).

EXAMPLE 2

(1R, 2S)-8-chloro-1-hydroxy-1,2,3,4-tetrahydronaphthalen-2-yl carbamate

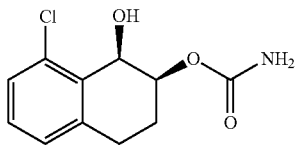 [SMILES: NC(=O)O[C@H]1CCc2cccc(Cl)c2[C@H]1O]

The substantially same method as described in Example 1 was conducted, except that (1R, 2S)-8-chloro-1,2,3,4-tetrahydronaphthalene-1,2-diol (Preparation example 7), was used instead of (1S, 2R)-8-chloro-1,2,3,4-tetrahydronaphthalene-1,2-diol (Preparation example 6), to obtain the title compound (1.3 g, 40-50%). $^1$H NMR (400 MHz, $CDCl_3$) δ 1.99-2.03 (m, 1H), 2.24-2.33 (m, 1H), 2.35 (d, 1H, J=3.2 Hz), 2.92-3.06 (m, 2H), 4.78 (br s, 2H), 4.79 (td, 1H, J=3.6, 12.8 Hz), 5.26 (s, 1H), 7.09 (d, 1H, J=7.6 Hz), 7.21 (t, 1H, J=8.0 Hz), 7.29 (d, 1H, J=8.0 Hz).

EXAMPLE 3

8-chloro-1-hydroxy-1,2,3,4-tetrahydronaphthalen-2-yl carbamate (mixture of SR & RS)

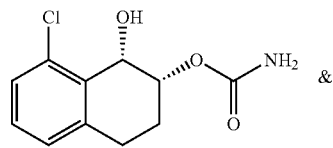 &

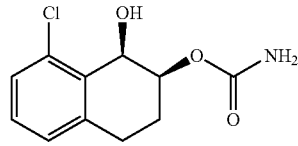

The substantially same method as described in Example 1 was conducted, except that 8-chloro-1,2,3,4-tetrahydronaphthalene-1,2-diol (Preparation example 23), was used instead of (1S, 2R)-8-chloro-1,2,3,4-tetrahydronaphthalene-1,2-diol (Preparation example 6), to obtain the title compound (0.86 g, 40-50%). $^1$H NMR (400 MHz, $CDCl_3$) δ 1.99-2.05 (m, 1H), 2.27-2.31 (m, 1H), 2.34 (d, J=3.3, 1H), 2.98-3.05 (m, 2H), 4.76 (br s, 2H), 4.93 (dt, J=3.6, 12.6, 1H), 5.24 (t, J=2.4, 1H), 7.07 (d, J=7.5, 1H), 7.19 (t, J=7.7, 1H), 7.27 (d, J=7.3, 1H).

EXAMPLE 4

(1R, 2R)-8-chloro-1-hydroxy-1,2,3,4-tetrahydronaphthalen-2-yl carbamate

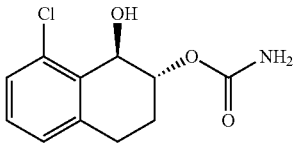 [SMILES: NC(=O)O[C@@H]1CCc2cccc(Cl)c2[C@H]1O]

To a stirred solution of (1R,2R)-1-((tert-butyldiphenylsilyl)oxy)-8-chloro-1,2,3,4-tetrahydronaphthalen-2-yl carbamate (Preparation example 27, 0.48 g, 1.00 mmol) in THF (10 mL) was added TBAF (1 M in THF, 1.0 mL, 1.00 mmol) at room temperature then stirred for 2 h. The resulting mixture was diluted with EtOAc, washed with $H_2O$ and brine, dried over $MgSO_4$, filtered and concentrated under reduced pressure. The crude product was purified by silica gel column chromatography to produce the title compound (73 mg, 61%). $^1$H NMR (400 MHz, $CDCl_3$) δ 1.91-1.98 (m, 1H), 2.02-2.10 (m, 1H), 2.74-2.81 (m, 1H), 2.95-3.03 (m, 1H), 4.28-4.31 (m, 1H), 4.76 (br s, 2H), 5.81 (d, J=3.6, 1H), 7.09 (d, J=7.6, 1H), 7.21 (t, J=7.6, 1H), 7.26-7.29 (m, 2H).

EXAMPLE 5

(1S, 2S)-8-chloro-1-hydroxy-1,2,3,4-tetrahydronaphthalen-2-yl carbamate

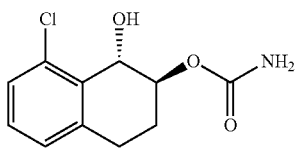 [SMILES: NC(=O)O[C@H]1CCc2cccc(Cl)c2[C@@H]1O]

The substantially same method as described in Example 4 was conducted, except that (1S,2S)-1-((tert-butyldiphenylsilyl)oxy)-8-chloro-1,2,3,4-tetrahydronaphthalen-2-yl carbamate (Preparation example 30), was used instead of (1R,2R)-1-((tert-butyldiphenylsilyl)oxy)-8-chloro-1,2,3,4-tetrahydronaphthalen-2-yl carbamate (Preparation example 27), to obtain the title compound (47 mg, 60%). $^1$H NMR (400 MHz, CDCl$_3$) δ 1.91-1.98 (m, 1H), 2.02-2.10 (m, 1H), 2.74-2.81 (m, 1H), 2.95-3.03 (m, 1H), 4.28-4.31 (m, 1H), 4.76 (br s, 2H), 5.81 (d, J=3.6, 1H), 7.09 (d, J=7.6, 1H), 7.21 (t, J=7.6, 1H), 7.26-7.29 (m, 2H).

EXAMPLE 6

(1S, 2R)-7-chloro-1-hydroxy-1,2,3,4-tetrahydronaphthalen-2-yl carbamate

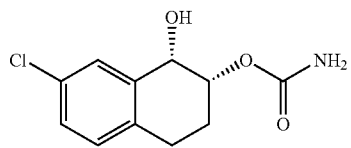 [SMILES: NC(=O)O[C@@H]1CCc2ccc(Cl)cc2[C@@H]1O]

The substantially same method as described in Example 1 was conducted, except that (1S,2R)-7-chloro-1,2,3,4-tetrahydronaphthalene-1,2-diol (Preparation example 34), was used instead of (1S, 2R)-8-chloro-1,2,3,4-tetrahydronaphthalene-1,2-diol (Preparation example 6), to obtain the title compound (2.1 g, 30%). $^1$H NMR (400 MHz, DMSO-d$_6$) δ 1.81-1.86 (m, 1H), 2.03-2.08 (m, 1H), 2.66-2.83 (m, 2H), 4.65 (br s, 1H), 4.83-4.87 (m, 1H), 5.44-5.48 (m, 1H), 6.44 (br s, 2H), 7.05 (d, J=8.0, 1H), 7.21 (dd, J=10.2, 2.4, 1H), 7.37 (d, J=2.4, 1H).

EXAMPLE 7

(1R, R)-7-chloro-1-hydroxy-1,2,3,4-tetrahydronaphthalen-2-yl carbamate

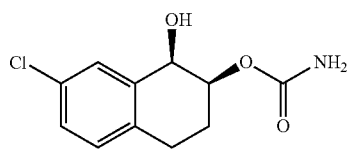 [SMILES: NC(=O)O[C@H]1CCc2ccc(Cl)cc2[C@H]1O]

The substantially same method as described in Example 1 was conducted, except that (1R,2S)-7-chloro-1,2,3,4-tetrahydronaphthalene-1,2-diol (Preparation example 35), was used instead of (1S, 2R)-8-chloro-1,2,3,4-tetrahydronaphthalene-1,2-diol (Preparation example 6), to obtain the title compound (2.1 g, 32%). $^1$H NMR (400 MHz, DMSO-d$_6$) δ 1.81-1.86 (m, 1H), 2.03-2.08 (m, 1H), 2.66-2.83 (m, 2H), 4.65 (br s, 1H), 4.83-4.87 (m, 1H), 5.44-5.48 (m, 1H), 6.44 (br s, 2H), 7.05 (d, J=8.0, 1H), 7.21 (dd, J=10.2, 2.4, 1H), 7.37 (d, J=2.4, 1H).

EXAMPLE 8

(1S, 2R)-6-chloro-1-hydroxy-1,2,3,4-tetrahydronaphthalen-2-yl carbamate

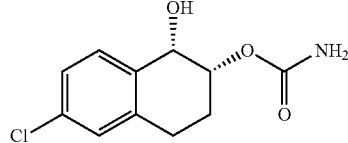 [SMILES: NC(=O)O[C@@H]1CCc2cc(Cl)ccc2[C@@H]1O]

The substantially same method as described in Example 1 was conducted, except that (1S,2R)-6-chloro-1,2,3,4-tetrahydronaphthalene-1,2-diol (Preparation example 39), was used instead of (1S, 2R)-8-chloro-1,2,3,4-tetrahydronaphthalene-1,2-diol (Preparation example 6), to obtain the title compound (0.29 g, 46%). $^1$H NMR (400 MHz, DMSO-d$_6$) δ 1.79-1.81 (m, 1H), 2.01-2.07 (m, 1H), 2.70-2.85 (m, 2H), 4.62 (s, 1H), 4.77-4.79 (m, 1H), 5.44 (s, 1H), 6.42 (br s, 2H), 7.15 (s, 1H), 7.20 (d, J=8.0, 1H), 7.35 (d, J=8.0, 1H).

EXAMPLE 9

(1R, 2S)-6-chloro-1-hydroxy-1,2,3,4-tetrahydronaphthalen-2-yl carbamate

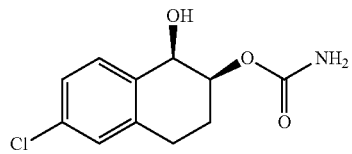 [SMILES: NC(=O)O[C@H]1CCc2cc(Cl)ccc2[C@H]1O]

The substantially same method as described in Example 1 was conducted, except that (1R,2S)-6-chloro-1,2,3,4-tetrahydronaphthalene-1,2-diol (Preparation example 40), was used instead of (1S, 2R)-8-chloro-1,2,3,4-tetrahydronaphthalene-1,2-diol (Preparation example 6), to obtain the title compound (0.22 g, 46%). $^1$H NMR (400 MHz, CDCl$_3$) δ 1.97-1.99 (m, 1H), 2.18-2.20 (m, 1H), 2.36-2.37 (br s, 1H), 2.81-2.83 (m, 1H), 2.95-2.97 (m, 1H), 4.72 (br s, 2H), 4.84-4.90 (m, 1H), 5.12-5.15 (m, 1H), 7.12-7.14 (m, 1H), 7.23-7.26 (m, 1H), 7.42-7.44 (m, 1H).

EXAMPLE 10

(1S, 2R)-8-fluoro-1-hydroxy-1,2,3,4-tetrahydronaphthalen-2-yl carbamate

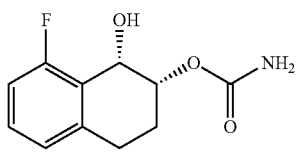 [SMILES: NC(=O)O[C@@H]1CCc2cccc(I)c2[C@@H]1O]

The substantially same method as described in Example 1 was conducted, except that (1S,2R)-8-fluoro-1,2,3,4-tetrahydronaphthalene-1,2-diol (Preparation example 43), was used instead of (1.5, 2R)-8-chloro-1,2,3,4-tetrahydronaphthalene-1,2-diol (Preparation example 6), to obtain the title compound (39 mg, 29%). $^1$H NMR (400 MHz, CDCl$_3$) δ 1.96-2.00 (m, 1H), 2.24 (d, J=3.5, 1H), 2.26-2.33 (m, 1H), 2.89-3.04 (m, 2H), 4.74 (br s, 2H), 4.95 (dt, J=3.5, 12.4, 1H), 5.23-5.28 (m, 1H), 6.90-6.95 (m, 2H), 7.21-7.24 (m, 1H).

EXAMPLE 11

(1R, 2S)-8-fluoro-1-hydroxy-1,2,3,4-tetrahydronaphthalen-2-yl carbamate

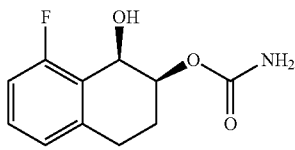 [SMILES: NC(=O)O[C@H]1CCc2cccc(I)c2[C@H]1O]

The substantially same method as described in Example 1 was conducted, except that (1R,2S)-8-fluoro-1,2,3,4-tetrahydronaphthalene-1,2-diol (Preparation example 44), was used instead of (1S, 2R)-8-chloro-1,2,3,4-tetrahydronaphthalene-1,2-diol (Preparation example 6), to obtain the title compound (0.41 g, 41%). $^1$H NMR (400 MHz, DMSO-d$_6$) δ 1.72-1.74 (m, 1H), 2.09-2.24 (m, 1H), 2.77-2.97 (m, 2H), 4.58 (d, J=12.4, 1H), 4.94 (s, 1H), 5.29 (d, J=4.8, 1H), 6.52 (br s, 2H), 6.96-7.01 (m, 2H), 7.23-7.29 (m, 1H).

EXAMPLE 12

(1S, 2R)-1-hydroxy-8-iodo-1,2,3,4-tetrahydronaphthalen-2-yl carbamate

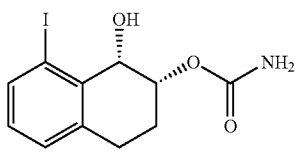

The substantially same method as described in Example 1 was conducted, except that (1S,2R)-8-iodo-1,2,3,4-tetrahydronaphthalene-1,2-diol (Preparation example 48), was used instead of (1S, 2R)-8-chloro-1,2,3,4-tetrahydronaphthalene-1,2-diol (Preparation example 6), to obtain the title compound (2.2 g, 37%). $^1$H NMR (400 MHz, DMSO-d$_6$) δ 1.68-1.72 (m, 1H), 2.07-2.18 (m, 1H), 2.84-2.88 (m, 2H), 4.43 (dt, J=12.8, 3.2, 1H), 4.70-4.72 (m, 1H), 5.14 (d, J=6.4, 1H), 6.52 (br s, 2H), 6.98 (t, J=7.6, 1H), 7.16 (d, J=7.6, 1H), 7.72 (d, J=6.8, 1H).

EXAMPLE 13

(1R, 2S)-1-hydroxy-8-iodo-1,2,3,4-tetrahydronaphthalen-2-yl carbamate

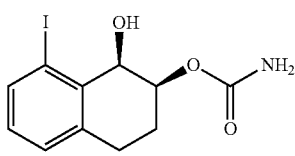

The substantially same method as described in Example 1 was conducted, except that (1R,2S)-8-iodo-1,2,3,4-tetrahydronaphthalene-1,2-diol (Preparation example 49), was used instead of (1S, 2R)-8-chloro-1,2,3,4-tetrahydronaphthalene-1,2-diol (Preparation example 6), to obtain the title compound (1.4 g, 27%). $^1$H NMR (400 MHz, DMSO-d$_6$) δ 1.68-1.72 (m, 1H), 2.07-2.18 (m, 1H), 2.84-2.88 (m, 2H), 4.43 (dt, J=12.8, 3.2, 1H), 4.70-4.72 (m, 1H), 5.14 (d, J=6.4, 1H), 6.52 (br s, 2H), 6.98 (t, J=7.6, 1H), 7.16 (d, J=7.6, 1H), 7.72 (d, J=6.8, 1H).

EXAMPLE 14

(1S, 2R)-1-hydroxy-1,2,3,4-tetrahydronaphthalen-2-yl carbamate

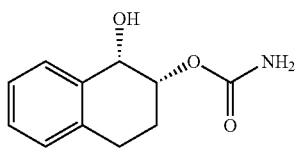 [SMILES: NC(=O)O[C@@H]1CCc2ccccc2[C@@H]1O]

The substantially same method as described in Example 1 was conducted, except that (1S,2R)-1,2,3,4-tetrahydronaphthalene-1,2-diol (Preparation example 51), was used instead of (1S, 2R)-8-chloro-1,2,3,4-tetrahydronaphthalene-1,2-diol (Preparation example 6), to obtain the title compound (1.04 g, 35%). $^1$H NMR (400 MHz, CDCl$_3$) δ 1.90-1.94 (m, 1H), 2.02-2.08 (m, 1H), 2.65-2.70 (m, 1H), 2.76-2.79 (m, 1H), 4.75 (d, J=3.7, 1H), 5.12-5.16 (m, 1H), 5.82 (br s, 2H), 7.06-7.09 (m, 2H), 7.12-7.15 (m, 1H), 7.24-7.26 (m, 1H).

EXAMPLE 15

(1R, 2S)-1-hydroxy-1,2,3,4-tetrahydronaphthalen-2-yl carbamate

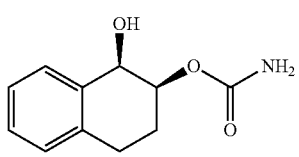 [SMILES: NC(=O)O[C@H]1CCc2ccccc2[C@H]1O]

The substantially same method as described in Example 1 was conducted, except that (1R,2S)-1,2,3,4-tetrahydronaphthalene-1,2-diol (Preparation example 52), was used instead of (1S, 2R)-8-chloro-1,2,3,4-tetrahydronaphthalene-1,2-diol (Preparation example 6), to obtain the title compound (0.86 g, 36%). $^1$H NMR (400 MHz, CDCl$_3$) δ 1.90-1.94 (m, 1H), 2.02-2.08 (m, 1H), 2.65-2.70 (m, 1H), 2.76-2.79 (m, 1H), 4.75 (d, J=3.7, 1H), 5.12-5.16 (m, 1H), 5.82 (br s, 2H), 7.06-7.09 (m, 2H), 7.12-7.15 (m, 1H), 7.24-7.26 (m, 1H).

EXAMPLE 16

(1S, 2R)-2-hydroxy-1,2,3,4-tetrahydronaphthalen-1-yl carbamate

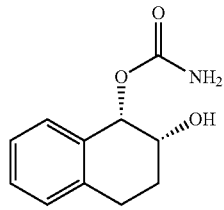 [SMILES: NC(=O)O[C@H]1c2ccccc2CC[C@H]1O]

The substantially same method as described in Example 1 was conducted, except that (1S,2R)-1,2,3,4-tetrahydronaphthalene-1,2-diol (Preparation example 51), was used instead of (1S, 2R)-8-chloro-1,2,3,4-tetrahydronaphthalene-1,2-diol (Preparation example 6), to obtain the title compound (1.01 g, 34%). $^1$H NMR (400 MHz, CDCl$_3$) δ 1.90-1.93 (m, 1H), 2.01-2.07 (m, 1H), 2.60-2.64 (m, 1H), 2.71-2.77 (m, 1H), 3.44-3.49 (m, 1H), 5.70 (d, J=10.1, 1H), 5.92 (br s, 2H), 7.07-7.10 (m, 1H), 7.15-7.19 (m, 2H), 7.25-7.27 (m, 1H).

EXAMPLE 17

(1R, 2S)-2-hydroxy-1,2,3,4-tetrahydronaphthalen-1-yl carbamate

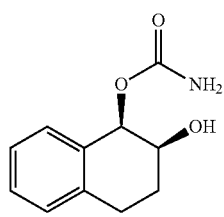 [SMILES: NC(=O)O[C@@H]1c2ccccc2CC[C@@H]1O]

The substantially same method as described in Example 1 was conducted, except that (1R,2S)-1,2,3,4-tetrahydronaphthalene-1,2-diol (Preparation example 52), was used instead of (1S, 2R)-8-chloro-1,2,3,4-tetrahydronaphthalene-1,2-diol (Preparation example 6), to obtain the title compound (0.88 g, 36%). $^1$H NMR (400 MHz, CDCl$_3$) δ 1.90-1.93 (m, 1H), 2.01-2.07 (m, 1H), 2.60-2.64 (m, 1H), 2.71-2.77 (m, 1H), 3.44-3.49 (m, 1H), 5.70 (d, J=10.1, 1H), 5.92 (br s, 2H), 7.07-7.10 (m, 1H), 7.15-7.19 (m, 2H), 7.25-7.27 (m, 1H).

EXAMPLE 18

(1S, 2R)-8-chloro-2-hydroxy-1,2,3,4-tetrahydronaphthalen-1-yl carbamate

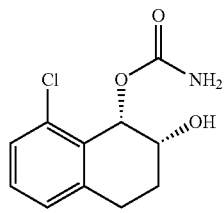

The substantially same method as described in Example 1 was conducted to obtain the title compound (2.1 g, 45%). $^1$H NMR (400 MHz, DMSO-d$_6$) δ 1.72-1.74 (m, 1H), 1.80-1.91 (m, 1H), 2.77-2.93 (m, 2H), 3.79-3.83 (m, 1H), 4.84 (d, J=4.0, 1H), 6.35 (br s, 2H), 7.12-7.14 (m, 1H), 7.25-7.31 (m, 2H).

EXAMPLE 19

(1R, 2S)-8-chloro-2-hydroxy-1,2,3,4-tetrahydronaphthalen-1-yl carbamate

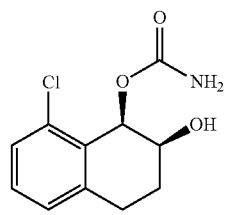

The substantially same method as described in Example 1 was conducted, except that (1R, 2S)-8-chloro-1,2,3,4-tetrahydronaphthalene-1,2-diol (Preparation example 7), was used instead of (1S, 2R)-8-chloro-1,2,3,4-tetrahydronaphthalene-1,2-diol (Preparation example 6), to obtain the title compound (2.4 g, 47%). $^1$H NMR (400 MHz, DMSO-d$_6$) δ 1.72-1.74 (m, 1H), 1.80-1.91 (m, 1H), 2.77-2.93 (m, 2H), 3.79-3.83 (m, 1H), 4.84 (d, J=4.0, 1H), 6.35 (br s, 2H), 7.12-7.14 (m, 1H), 7.25-7.31 (m, 2H).

EXAMPLE 20

8-chloro-2-hydroxy-1,2,3,4-tetrahydronaphthalen-1-yl carbamate (mixture of SR & RS)

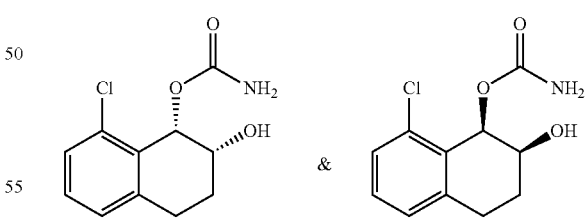

The substantially same method as described in Example 1 was conducted, except that 8-chloro-1,2,3,4-tetrahydronaphthalene-1,2-diol (Preparation example 23), was used instead of (1S, 2R)-8-chloro-1,2,3,4-tetrahydronaphthalene-1,2-diol (Preparation example 6), to obtain the title compound (0.98 g, 33%). $^1$H NMR (400 MHz, DMSO-d$_6$) δ 1.75-1.78 (m, 1H), 1.79-1.89 (m, 1H), 2.75-2.94 (m, 2H), 3.80-3.83 (m, 1H), 4.82 (d, J=4.0, 1H), 6.30 (br s, 2H), 7.11-7.15 (m, 1H), 7.27-7.32 (m, 2H).

EXAMPLE 21

(1S, 2R)-7-chloro-2-hydroxy-1,2,3,4-tetrahydronaphthalen-1-yl carbamate

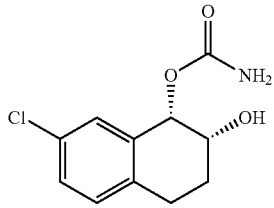 [SMILES: NC(=O)O[C@H]1c2cc(Cl)ccc2CC[C@H]1O]

The substantially same method as described in Example 1 was conducted, except that (1S,2R)-7-chloro-1,2,3,4-tetrahydronaphthalene-1,2-diol (Preparation example 34), was used instead of (1S, 2R)-8-chloro-1,2,3,4-tetrahydronaphthalene-1,2-diol (Preparation example 6), to obtain the title compound (2.1 g, 32%). $^1$H NMR (400 MHz, DMSO-$d_6$) δ 1.93-1.98 (m, 1H), 2.04-2.09 (m, 1H), 2.76-2.92 (m, 2H), 3.75 (br s, 1H), 4.98-5.0 (m, 1H), 5.79 (d, J=3.2, 1H), 6.59 (br s, 2H), 7.19 (d, J=8.4, 1H), 7.23 (d, J=2.0, 1H), 7.3 (dd, J=8.0, 2.4, 1H).

EXAMPLE 22

(1R, 2S)-7-chloro-2-hydroxy-1,2,3,4-tetrahydronaphthalen-1-yl carbamate

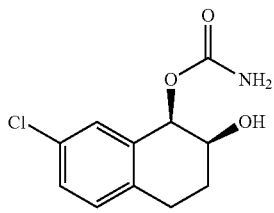 [SMILES: NC(=O)O[C@@H]1c2cc(Cl)ccc2CC[C@@H]1O]

The substantially same method as described in Example 1 was conducted, except that (1R,2S)-7-chloro-1,2,3,4-tetrahydronaphthalene-1,2-diol (Preparation example 35), was used instead of (1S, 2R)-8-chloro-1,2,3,4-tetrahydronaphthalene-1,2-diol (Preparation example 6), to obtain the title compound (2.3 g, 34%). $^1$H NMR (400 MHz, DMSO-$d_6$) δ 1.93-1.98 (m, 1H), 2.04-2.09 (m, 1H), 2.76-2.92 (m, 2H), 3.75 (br s, 1H), 4.98-5.0 (m, 1H), 5.79 (d, J=3.2, 1H), 6.59 (br s, 2H), 7.19 (d, J=8.4, 1H), 7.23 (d, J=2.0, 1H), 7.3 (dd, J=8.0, 2.4, 1H).

EXAMPLE 23

(1S, 2R)-6-chloro-2-hydroxy-1,2,3,4-tetrahydronaphthalen-1-yl carbamate

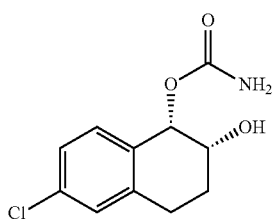 [SMILES: NC(=O)O[C@H]1c2ccc(Cl)cc2CC[C@H]1O]

The substantially same method as described in Example 1 was conducted, except that (1S,2R)-6-chloro-1,2,3,4-tetrahydronaphthalene-1,2-diol (Preparation example 39), was used instead of (1S, 2R)-8-chloro-1,2,3,4-tetrahydronaphthalene-1,2-diol (Preparation example 6), to obtain the title compound (0.25 g, 40%). $^1$H NMR (400 MHz, DMSO-$d_6$) δ 1.79-1.81 (m, 1H), 1.87-1.89 (m, 1H), 2.68-2.73 (m, 1H), 2.86-2.91 (m, 1H), 5.04 (s, 1H), 5.60 (s, 1H), 6.48 (br s, 2H), 7.18-7.24 (m, 3H).

EXAMPLE 24

(1R, 2S)-6-chloro-2-hydroxy-1,2,3,4-tetrahydronaphthalen-1-yl carbamate

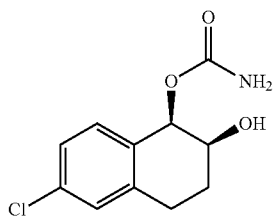 [SMILES: NC(=O)O[C@@H]1c2ccc(Cl)cc2CC[C@@H]1O]

The substantially same method as described in Example 1 was conducted, except that (1R,2S)-6-chloro-1,2,3,4-tetrahydronaphthalene-1,2-diol (Preparation example 40), was used instead of (1S, 2R)-8-chloro-1,2,3,4-tetrahydronaphthalene-1,2-diol (Preparation example 6), to obtain the title compound (0.19 g, 40%). $^1$H NMR (400 MHz, CDCl$_3$) δ 1.96-2.00 (m, 2H), 2.59-2.64 (m, 1H), 2.97-3.01 (m, 1H), 3.95-4.00 (m, 1H), 4.13-4.15 (m, 1H), 5.57 (br s, 2H), 5.81-5.85 (m, 1H), 7.07-7.12 (m, 2H), 7.29-7.32 (m, 1H).

EXAMPLE 25

(1S, 2R)-8-fluoro-2-hydroxy-1,2,3,4-tetrahydronaphthalen-1-yl carbamate

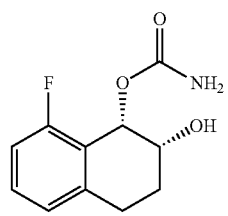

The substantially same method as described in Example 1 was conducted, except that (1S,2R)-8-fluoro-1,2,3,4-tetrahydronaphthalene-1,2-diol (Preparation example 43), was used instead of (1S, 2R)-8-chloro-1,2,3,4-tetrahydronaphthalene-1,2-diol (Preparation example 6), to obtain the title compound (0.65 g, 48%). $^1$H NMR (400 MHz, CDCl$_3$) δ 2.01-2.06 (m, 2H), 2.71-2.78 (m, 2H), 3.45-3.49 (m, 1H), 5.82 (d, J=10.0, 1H), 6.12 (br s, 2H), 6.91 (dd, J=1.2, 8.3, 1H), 6.94 (dd, J=1.2, 7.8, 1H), 7.20 (dd, J=7.7 , 8.4, 1H)

EXAMPLE 26

(1R, 2S)-8-fluoro-2-hydroxy-1,2,3,4-tetrahydronaphthalen-1-yl carbamate

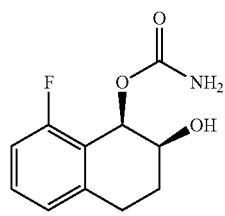 [SMILES: NC(=O)O[C@@H]1c2c(F)cccc2CC[C@@H]1O]

The substantially same method as described in Example 1 was conducted, except that (1R,2S)-8-fluoro-1,2,3,4-tetrahydronaphthalene-1,2-diol (Preparation example 44), was used instead of (1S, 2R)-8-chloro-1,2,3,4-tetrahydronaphthalene-1,2-diol (Preparation example 6) to obtain the title compound (0.45 g, 42%). $^1$H NMR (400 MHz, CDCl$_3$) δ 2.01-2.06 (m, 2H), 2.71-2.78 (m, 2H), 3.45-3.49 (m, 1H), 5.82 (d, J=10.0, 1H), 6.12 (br s, 2H), 6.91 (dd, J=1.2, 8.3, 1H), 6.94 (dd, J=1.2, 7.8, 1H), 7.20 (dd, J=7.7, 8.4, 1H)

EXAMPLE 27

(1S, 2R)-2-hydroxy-8-iodo-1,2,3,4-tetrahydronaphthalen-1-yl carbamate

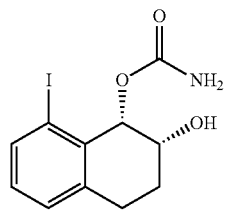 [SMILES: NC(=O)O[C@H]1c2c(I)cccc2CC[C@H]1O]

The substantially same method as described in Example 1 was conducted, except that (1S,2R)-8-iodo-1,2,3,4-tetrahydronaphthalene-1,2-diol (Preparation example 48), was used instead of (1S, 2R)-8-chloro-1,2,3,4-tetrahydronaphthalene-1,2-diol (Preparation example 6), to obtain the title compound (1.6 g, 38%). $^1$H NMR (400 MHz, DMSO-d$_6$) δ 1.67-1.70 (m, 1H), 1.79-1.90 (m, 1H), 2.77-2.87 (m, 2H), 3.78-3.85 (m, 1H), 4.79 (d, 1H, J=3.2), 5.76 (d, 1H, J=2.8), 6.96-7.03 (m, 1H), 7.16-7.19 (m, 1H), 7.72-7.77 (m, 1H).

EXAMPLE 28

(1R, 2S)-2-hydroxy-8-iodo-1,2,3,4-tetrahydronaphthalen-1-yl carbamate

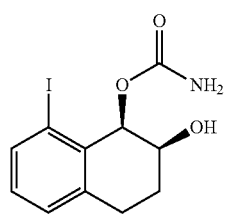 [SMILES: NC(=O)O[C@@H]1c2c(I)cccc2CC[C@@H]1O]

The substantially same method as described in Example 1 was conducted, except that (1R,2S)-8-iodo-1,2,3,4-tetrahydronaphthalene-1,2-diol (Preparation example 49), was used instead of (1S, 2R)-8-chloro-1,2,3,4-tetrahydronaphthalene-1,2-diol (Preparation example 6), to obtain the title compound (1.25 g, 39%). $^1$H NMR (400 MHz, DMSO-d$_6$) δ 1.67-1.70 (m, 1H), 1.79-1.90 (m, 1H), 2.77-2.87 (m, 2H), 3.78-3.85 (m, 1H), 4.79 (d, 1H, J=3.2), 5.76 (d, 1H, J=2.8), 6.96-7.03 (m, 1H), 7.16-7.19 (m, 1H), 7.72-7.77 (m, 1H).

EXAMPLE 29

(1S, 2R)-8-chloro-1,2,3,4-tetrahydronaphthalen-1,2-diyldicarbamate

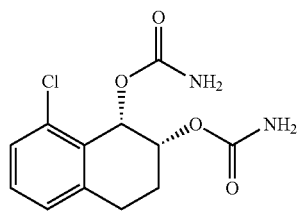 [SMILES: NC(=O)O[C@@H]1CCc2cccc(Cl)c2[C@@H]1OC(N)=O]

The substantially same method as described in Example 1 was conducted, except that (1S, 2R)-8-chloro-1-hydroxy-1,2,3,4-tetrahydronaphthalen-2-yl carbamate (Example 1), was used instead of (1S, 2R)-8-chloro-1,2,3,4-tetrahydronaphthalene-1,2-diol (Preparation example 6), to obtain the title compound (0.72 g, 63%). $^1$H NMR (400 MHz, DMSO-d$_6$) δ 7.32 (m, 2H), 7.17 (d, 1H, J=6.96 Hz), 6.44 (br s, 4H), 6.16 (d, 1H, J=2.88 Hz), 4.78 (dt, 1H, J=3.36, 12.80 Hz), 2.96 (m, 2H), 2.05 (m, 1H), 1.83 (m, 1H).

EXAMPLE 30

(1R, 2S)-8-chloro-1,2,3,4-tetrahydronaphthalen-1,2-diyl dicarbamate

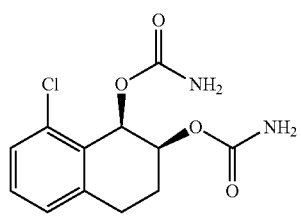 [SMILES: NC(=O)O[C@H]1CCc2cccc(Cl)c2[C@H]1OC(N)=O]

The substantially same method as described in Example 1 was conducted, except that (1R, 2S)-8-chloro-1-hydroxy-1,2,3,4-tetrahydronaphthalen-2-yl carbamate (Example 2), was used instead of (1S, 2R)-8-chloro-1,2,3,4-tetrahydronaphthalene-1,2-diol (Preparation example 6), to obtain the title compound (0.55 g, 68%). $^1$H NMR (400 MHz, DMSO-d$_6$) δ 7.32 (m, 2H), 7.17 (d, 1H, J=6.96 Hz), 6.44 (br s, 4H), 6.16 (d, 1H, J=2.88 Hz), 4.78 (dt, 1H, J=3.36, 12.80 Hz), 2.96 (m, 2H), 2.05 (m, 1H), 1.83 (m, 1H).

EXAMPLE 31

(1R, 2R)-8-chloro-1,2,3,4-tetrahydronaphthalen-1,2-diyl dicarbamate

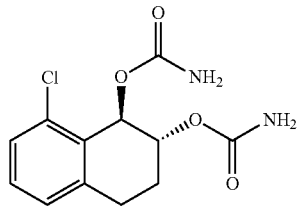 [SMILES: NC(=O)O[C@@H]1c2c(Cl)cccc2CC[C@H]1OC(N)=O]

The substantially same method as described in Example 1 was conducted, except that (1R, 2R)-8-chloro-1-hydroxy-1,2,3,4-tetrahydronaphthalen-2-yl carbamate (Example 4), was used instead of (1S, 2R)-8-chloro-1,2,3,4-tetrahydronaphthalene-1,2-diol (Preparation example 6), to obtain the title compound (0.95 g, 78%). $^1$H NMR (400 MHz, CDCl$_3$) δ 1.95-1.99 (m, 2H), 2.73-2.79 (m, 2H), 5.20-5.22 (m, 1H), 5.56 (br s, 4H), 5.87 (d, 1H, J=10.06 Hz), 6.97 (dd, 1H, J=8.06, 1.59 Hz), 7.11 (dd, 1H, J=7.99, 1.59 Hz), 7.30 (dd, 1H, J=8.09, 7.99 Hz).

EXAMPLE 32

(1S, 2R)-7-chloro-1,2,3,4-tetrahydronaphthalen-1,2-diyl dicarbamate

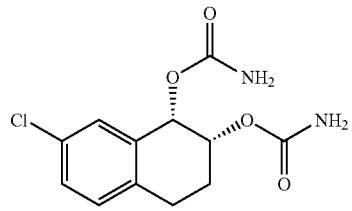 [SMILES: NC(=O)O[C@@H]1CCc2ccc(Cl)cc2[C@@H]1OC(N)=O]

The substantially same method as described in Example 1 was conducted, except that (1S, 2R)-7-chloro-1-hydroxy-1,2,3,4-tetrahydronaphthalen-2-yl carbamate (Example 6), was used instead of (1S, 2R)-8-chloro-1,2,3,4-tetrahydronaphthalene-1,2-diol (Preparation example 6), to obtain the title compound (0.45 g, 83%). $^1$H NMR (400 MHz, CDCl$_3$) δ 2.02-2.04 (m, 2H), 2.68-2.78 (m, 2H), 5.20-5.23 (m, 1H), 5.48 (br s, 4H), 5.86 (d, 1H, J=10.06 Hz), 7.16 (dd, 1H, J=8.06, 1.59 Hz), 7.29 (dd, 1H, J=7.99, 1.59 Hz), 7.44 (dd, 1H, J=8.09, 7.99 Hz).

EXAMPLE 33

(1R, 2S)-6-chloro-1,2,3,4-tetrahydronaphthalen-1,2-diyl dicarbamate

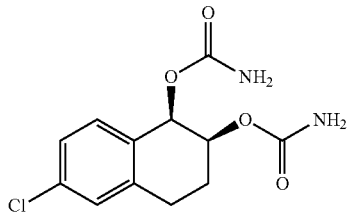 [SMILES: NC(=O)O[C@H]1CCc2cc(Cl)ccc2[C@H]1OC(N)=O]

The substantially same method as described in Example 1 was conducted, except that (1R, 2S)-6-chloro-1-hydroxy-1,2,3,4-tetrahydronaphthalen-2-yl carbamate (Example 9), was used instead of (1S, 2R)-8-chloro-1,2,3,4-tetrahydronaphthalene-1,2-diol (Preparation example 6), to obtain the title compound (0.45 g, 83%). $^1$H NMR (400 MHz, CDCl$_3$) δ 2.02-2.05 (m, 2H), 2.71-2.74 (m, 2H), 5.22-5.25 (m, 1H), 5.92 (br s, 4H), 5.88 (d, 1H, J=3.69 Hz), 7.10-7.14 (m, 2H), 7.39 (dd, 1H, J=8.27, 1.46 Hz).

EXAMPLE 34

(1S, 2R)-8-fluoro-1,2,3,4-tetrahydronaphthalen-1,2-diyl dicarbamate

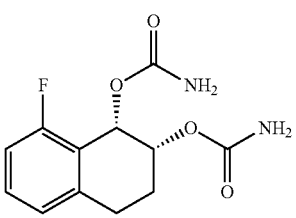 [SMILES: NC(=O)O[C@@H]1CCc2cccc(F)c2[C@@H]1OC(N)=O]

The substantially same method as described in Example 1 was conducted, except that (1S, 2R)-8-fluoro-1-hydroxy-1,2,3,4-tetrahydronaphthalen-2-yl carbamate (Example 10), was used instead of (1S, 2R)-8-chloro-1,2,3,4-tetrahydronaphthalene-1,2-diol (Preparation example 6), to obtain the title compound (0.89 g, 82%). $^1$H NMR (400 MHz, DMSO-d$_6$) δ 1.70-1.90 (m, 1H), 1.95-2.13 (m, 1H), 2.85-3.03 (m, 2H), 4.71-4.89 (m, 1H), 6.18 (d, J=3.6 Hz, 1H), 6.47 (br s, 4H), 6.94-7.11 (m, 2H), 7.25-7.39 (m, 1H).

EXAMPLE 35

(1R, 2S)-8-fluoro-1,2,3,4-tetrahydronaphthalen-1,2-diyl dicarbamate

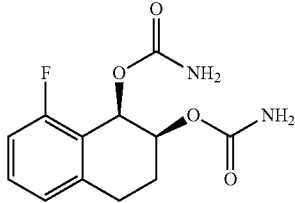

The substantially same method as described in Example 1 was conducted, except that (1R, 2S)-8-fluoro-1-hydroxy-1,2,3,4-tetrahydronaphthalen-2-yl carbamate (Example 11), was used instead of (1S, 2R)-8-chloro-1,2,3,4-tetrahydronaphthalene-1,2-diol (Preparation example 6), to obtain the title compound (1.20 g, 80%). $^1$H NMR (400 MHz, DMSO-$d_6$) δ 1.70-1.90 (m, 1H), 1.95-2.13 (m, 1H), 2.85-3.03 (m, 2H), 4.71-4.89 (m, 1H), 6.18 (d, J=3.6 Hz, 1H), 6.47 (br s, 4H), 6.94-7.11 (m, 2H), 7.25-7.39 (m, 1H).

EXAMPLE 36

(1S, 2R)-8-iodo-1,2,3,4-tetrahydronaphthalen-1,2-diyl dicarbamate

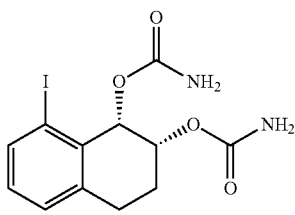 [SMILES: NC(=O)O[C@@H]1CCc2cccc(I)c2[C@@H]1OC(N)=O]

The substantially same method as described in Example 1 was conducted, except that (1S, 2R)-1-hydroxy-8-iodo-1,2,3,4-tetrahydronaphthalen-2-yl carbamate (Example 12), was used instead of (1S, 2R)-8-chloro-1,2,3,4-tetrahydronaphthalene-1,2-diol (Preparation example 6), to obtain the title compound (0.86 g, 67%). $^1$H NMR (400 MHz, DMSO-$d_6$) δ 1.92-1.98 (m, 1H), 2.13-2.19 (m, 1H), 2.98 (d, J=6.8, 1H), 4.11-4.16 (m, 1H), 4.64 (br s, 2H), 4.68 (br s, 2H), 5.03-5.06 (m, 1H), 6.12 (s, 1H), 6.99 (t, J=7.2, 1H), 7.15-7.17 (m, 1H), 7.80 (d, J=7.2, 1H).

EXAMPLE 37

(1R, 2S)-8-iodo-1,2,3,4-tetrahydronaphthalen-1,2-diyl dicarbamate

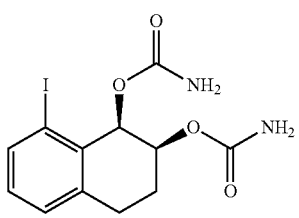 [SMILES: NC(=O)O[C@H]1CCc2cccc(I)c2[C@H]1OC(N)=O]

The substantially same method as described in Example 1 was conducted, except that (1R, 2S)-1-hydroxy-8-iodo-1,2,3,4-tetrahydronaphthalen-2-yl carbamate (Example 13), was used instead of (1S, 2R)-8-chloro-1,2,3,4-tetrahydronaphthalene-1,2-diol (Preparation example 6), to obtain the title compound (0.73 g, 65%). $^1$H NMR (400 MHz, DMSO-$d_6$) δ 1.92-1.98 (m, 1H), 2.13-2.19 (m, 1H), 2.98 (d, J=6.8, 1H), 4.11-4.16 (m, 1H), 4.64 (br s, 2H), 4.68 (br s, 2H), 5.03-5.06 (m, 1H), 6.12 (s, 1H), 6.99 (t, J=7.2, 1H), 7.15-7.17 (m, 1H), 7.80 (d, J=7.2, 1H).

EXAMPLE 38

(1S, 2R)-1,2,3,4-tetrahydronaphthalen-1,2-diyl dicarbamate

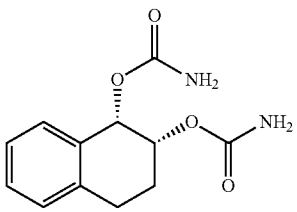 [SMILES: NC(=O)O[C@@H]1CCc2ccccc2[C@@H]1OC(N)=O]

The substantially same method as described in Example 1 was conducted, except that (1S, 2R)-1-hydroxy-1,2,3,4-tetrahydronaphthalen-2-yl carbamate (Example 14), was used instead of (1S, 2R)-8-chloro-1,2,3,4-tetrahydronaphthalene-1,2-diol (Preparation example 6), to obtain the title compound (0.48 g, 80%). $^1$HNMR (400 MHz, CDCl$_3$) δ 1.98-2.01 (m, 2H), 2.68-2.77 (m, 2H), 5.20-5.25 (m, 1H), 5.76 (d, J=10.1, 1H), 5.88 (br s, 2H), 5.91 (br s, 2H), 7.07-7.12 (m, 2H), 7.19-7.23 (m, 1H), 7.25-7.28 (m, 1H).

EXAMPLE 39

(1R, 2S)-1,2,3,4-tetrahydronaphthalen-1,2-diyl dicarbamate

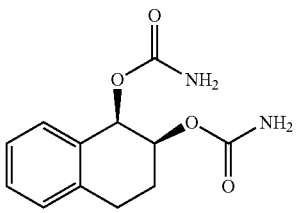 [SMILES: NC(=O)O[C@H]1CCc2ccccc2[C@H]1OC(N)=O]

The substantially same method as described in Example 1 was conducted, except that (1R, 2S)-1-hydroxy-1,2,3,4-tetrahydronaphthalen-2-yl carbamate (Example 15), was used instead of (1S, 2R)-8-chloro-1,2,3,4-tetrahydronaphthalene-1,2-diol (Preparation example 6), to obtain the title compound (0.96 g, 75%). $^1$H NMR (400 MHz, CDCl$_3$) δ 1.98-2.01 (m, 2H), 2.68-2.77 (m, 2H), 5.20-5.25 (m, 1H), 5.76 (d, J=10.1, 1H), 5.88 (br s, 2H), 5.91 (br s, 2H), 7.07-7.12 (m, 2H), 7.19-7.23 (m, 1H), 7.25-7.28 (m, 1H).

EXAMPLE 40

(1S, 2R)-8-chloro-1-(methoxymethoxy)-1,2,3,4-tetrahydronaphthalen-2-yl carbamate

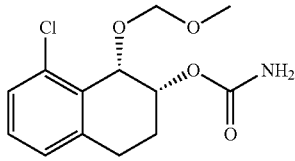 [SMILES: COCO[C@H]1c2c(Cl)cccc2CC[C@H]1OC(N)=O]

To a stirred solution of (1S,2R)-8-chloro-1-hydroxy-1,2,3,4-tetrahydronaphthalen-2-yl carbamate (Example 1, 0.5 g, 2.07 mmol) in $CH_2Cl_2$ (5 mL) was sequentially added DIPEA (1.8 mL, 10.34 mmol) and MOM-Cl (0.78 mL, 10.34 mmol) at 0° C. The mixture was slowly warmed to room temperature then stirred for 6 h. The resulting mixture was diluted with $CH_2Cl_2$, washed with water, dried over $MgSO_4$, filtered and concentrated under reduced pressure. The crude product was purified by silica gel column chromatography to produce the title compound (0.53 g, 78%). $^1$H NMR (400 MHz, DMSO-$d_6$) δ 1.79-1.88 (m, 1H), 2.10-2.24 (m, 1H), 2.83-2.96 (m, 1H), 2.96-3.05 (m, 1H), 3.29 (s, 3H), 4.62-4.70 (m, 1H), 4.72 (d, J=6.0, 1H), 4.86 (d, J=5.6, 1H), 5.03 (d, J=1.6, 1H), 6.56 (br s, 1H), 6.72 (br s, 1H), 7.12-7.18 (m, 1H), 7.25-7.35 (m, 2H).

EXAMPLE 41

(1R, 2S)-8-chloro-1-(methoxymethoxy)-1,2,3,4-tetrahydronaphthalen-2-yl carbamate

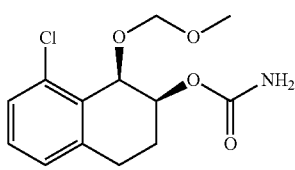 [SMILES: COCO[C@@H]1c2c(Cl)cccc2CC[C@@H]1OC(N)=O]

The substantially same method as described in Example 40 was conducted, except that (1R,2S)-8-chloro-1-hydroxy-1,2,3,4-tetrahydronaphthalen-2-yl carbamate (Example 2), was used instead of (1S,2R)-8-chloro-1-hydroxy-1,2,3,4-tetrahydronaphthalen-2-yl carbamate (Example 1), to obtain the title compound (0.47 g, 80%). $^1$H NMR (400 MHz, DMSO-$d_6$) δ 1.79-1.88 (m, 1H), 2.10-2.24 (m, 1H), 2.83-2.96 (m, 1H), 2.96-3.05 (m, 1H), 3.29 (s, 3H), 4.62-4.70 (m, 1H), 4.72 (d, J=6.0, 1H), 4.86 (d, J=5.6, 1H), 5.03 (d, J=1.6, 1H), 6.56 (br s, 1H), 6.72 (br s, 1H), 7.12-7.18 (m, 1H), 7.25-7.35 (m, 2H).

EXAMPLE 42

(1R, 2R)-8-chloro-1-(methoxymethoxy)-1,2,3,4-tetrahydronaphthalen-2-yl carbamate

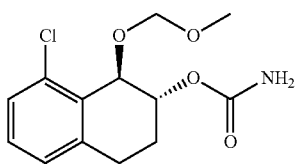 [SMILES: COCO[C@@H]1c2c(Cl)cccc2CC[C@H]1OC(N)=O]

The substantially same method as described in Example 40 was conducted, except that (1R, 2R)-8-chloro-1-hydroxy-1,2,3,4-tetrahydronaphthalen-2-yl carbamate (Example 4), was used instead of (1S,2R)-8-chloro-1-hydroxy-1,2,3,4-tetrahydronaphthalen-2-yl carbamate (Example 1), to obtain the title compound (0.85 g, 63%). $^1$H NMR (400 MHz, DMSO-$d_6$) δ 1.85-1.99 (m, 2H), 2.82-2.97 (m, 2H), 3.30 (s, 3H), 3.83-3.88 (m, 1H), 4.53 (d, J=6.8 Hz, 1H), 4.81 (d, J=6.8 Hz, 1H), 6.11 (d, J=3.2 Hz, 1H), 6.33 (br s, 2H), 7.14-7.16 (m, 1H), 7.27-7.33 (m, 2H).

EXAMPLE 43

(1S, 2R)-8-fluoro-1-(methoxymethoxy)-1,2,3,4-tetrahydronaphthalen-2-yl carbamate

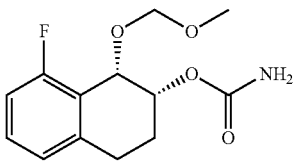 [SMILES: COCO[C@H]1c2c(F)cccc2CC[C@H]1OC(N)=O]

The substantially same method as described in Example 40 was conducted, except that (1S, 2R)-8-fluoro-1-hydroxy-1,2,3,4-tetrahydronaphthalen-2-yl carbamate (Example 10), was used instead of (1S ,2R)-8-chloro-1-hydroxy-1,2,3,4-tetrahydronaphthalen-2-yl carbamate (Example 1), to obtain the title compound (1.08 g, 60%). $^1$H NMR (400 MHz, CDCl$_3$) δ 1.94-2.00 (m, 1H), 2.30-2.41 (m, 1H), 2.89-3.10 (m, 2H), 3.41 (s, 3H), 4.71 (br s, 2H), 4.78 (d, J=6.4 Hz, 1H), 4.87 (d, J=6.8 Hz, 1H), 4.92 (td, J=12.4, 3.2 Hz, 1H), 5.15 (d, J=3.2 Hz, 1H), 6.88-6.94 (m, 2H), 7.19-7.24 (m, 1H).

EXAMPLE 44

(1R, 2S)-8-fluoro-1-(methoxymethoxy)-1,2,3,4-tetrahydronaphthalen-2-yl carbamate

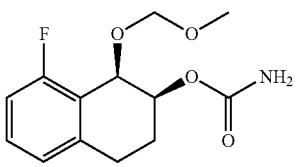 [SMILES: COCO[C@@H]1c2c(F)cccc2CC[C@@H]1OC(N)=O]

The substantially same method as described in Example 40 was conducted, except that (1R, 2S)-8-fluoro-1-hydroxy-1,2,3,4-tetrahydronaphthalen-2-yl carbamate (Example 11), was used instead of (1S ,2R)-8-chloro-1-hydroxy-1,2,3,4-tetrahydronaphthalen-2-yl carbamate (Example 1), to obtain the title compound (1.24 g, 56%). $^1$H NMR (400 MHz, CDCl$_3$) δ 1.94-2.00 (m, 1H), 2.30-2.41 (m, 1H), 2.89-3.10 (m, 2H), 3.41 (s, 3H), 4.71 (br s, 2H), 4.78 (d, J=6.4 Hz, 1H), 4.87 (d, J=6.8 Hz, 1H), 4.92 (td, J=12.4, 3.2 Hz, 1H), 5.15 (d, J=3.2 Hz, 1H), 6.88-6.94 (m, 2H), 7.19-7.24 (m, 1H).

EXAMPLE 45

(1S, 2R)-8-chloro-2-(methoxymethoxy)-1,2,3,4-tetrahydronaphthalen-1-yl carbamate

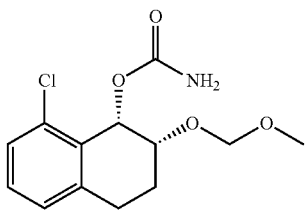 [SMILES: COCO[C@@H]1CCc2cccc(Cl)c2[C@@H]1OC(N)=O]

The substantially same method as described in Example 40 was conducted, except that (1S, 2R)-8-chloro-2-hydroxy-1,2,3,4-tetrahydronaphthalen-1-yl carbamate (Example 18), was used instead of (1S,2R)-8-chloro-1-hydroxy-1,2,3,4-tetrahydronaphthalen-2-yl carbamate (Example 1), to obtain the title compound (0.58 g, 54%). $^1$H NMR 1.83-1.88 (m, 2H), 2.73-2.77 (m, 2H), 3.22 (s, 3H), 4.01-4.05 (m, 1H), 4.55-4.59 (m, 2H), 5.05 (br s, 2H), 5.81 (d, 1H, J=10.06 Hz), 6.98-7.16 (m, 2H), 7.27-7.29 (m, 1H).

EXAMPLE 46

(1R, 2S)-8-chloro-2-(methoxymethoxy)-1,2,3,4-tetrahydronaphthalen-1-yl carbamate

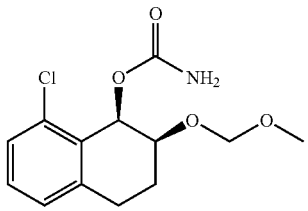 [SMILES: COCO[C@H]1CCc2cccc(Cl)c2[C@H]1OC(N)=O]

The substantially same method as described in Example 40 was conducted, except that (1R, 2S)-8-chloro-2-hydroxy-1,2,3,4-tetrahydronaphthalen-1-yl carbamate (Example 19), was used instead of (1S,2R)-8-chloro-1-hydroxy-1,2,3,4-tetrahydronaphthalen-2-yl carbamate (Example 1), to obtain the title compound (0.77 g, 55%). $^1$H NMR δ 1.83-1.88 (m, 2H), 2.73-2.77 (m, 2H), 3.22 (s, 3H), 4.01-4.05 (m, 1H), 4.55-4.59 (m, 2H), 5.05 (br s, 2H), 5.81 (d, 1H, J=10.06 Hz), 6.98-7.16 (m, 2H), 7.27-7.29 (m, 1H).

EXAMPLE 47

(1S, 2R)-8-fluoro-2-(methoxymethoxy)-1,2,3,4-tetrahydronaphthalen-1-yl carbamate

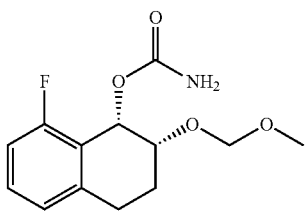 [SMILES: COCO[C@@H]1CCc2cccc(F)c2[C@@H]1OC(N)=O]

The substantially same method as described in Example 40 was conducted, except that (1S, 2R)-8-fluoro-2-hydroxy-1,2,3,4-tetrahydronaphthalen-1-yl carbamate (Example 25), was used instead of (1S,2R)-8-chloro-1-hydroxy-1,2,3,4-tetrahydronaphthalen-2-yl carbamate (Example 1), to obtain the title compound (0.89 g, 57%). $^1$H NMR (400 MHz, CDCl$_3$) δ 1.91-2.01 (m, 1H), 2.02-2.18 (m, 1H), 2.82-2.94 (m, 1H), 2.97-3.08 (m, 1H), 3.43 (s, 3H), 3.94-4.03 (m, 1H), 4.50-4.45 (m, 3H), 4.93 (d, J=7.2 Hz, 1H), 6.35 (d, J=3.6 Hz, 1H), 6.87-6.97 (m, 2H), 7.20-7.28 (m, 1H).

EXAMPLE 48

(1R, 2S)-8-fluoro-2-(methoxymethoxy)-1,2,3,4-tetrahydronaphthalen-1-yl carbamate

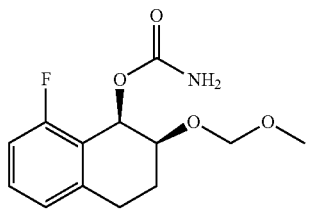 [SMILES: COCO[C@H]1CCc2cccc(F)c2[C@H]1OC(N)=O]

The substantially same method as described in Example 40 was conducted, except that (1R, 2S)-8-fluoro-2-hydroxy-1,2,3,4-tetrahydronaphthalen-1-yl carbamate (Example 26), was used instead of (1S,2R)-8-chloro-1-hydroxy-1,2,3,4-tetrahydronaphthalen-2-yl carbamate (Example 1), to obtain the title compound (1.1 g, 58%). $^1$H NMR (400 MHz, CDCl$_3$) δ 1.91-2.01 (m, 1H), 2.02-2.18 (m, 1H), 2.82-2.94 (m, 1H), 2.97-3.08 (m, 1H), 3.43 (s, 3H), 3.94-4.03 (m, 1H), 4.50-4.45 (m, 3H), 4.93 (d, J=7.2 Hz, 1H), 6.35 (d, J=3.6 Hz, 1H), 6.87-6.97 (m, 2H), 7.20-7.28 (m, 1H).

EXAMPLE 49

(1S, 2R)-8-iodo-2-(methoxymethoxy)-1,2,3,4-tetrahydronaphthalen-1-yl carbamate

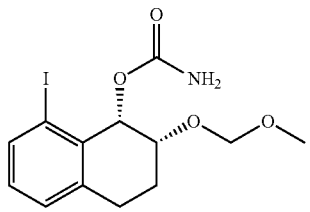 [SMILES: COCO[C@@H]1CCc2cccc(I)c2[C@@H]1OC(N)=O]

The substantially same method as described in Example 40 was conducted, except that (1S, 2R)-2-hydroxy-8-iodo-1,2,3,4-tetrahydronaphthalen-1-yl carbamate (Example 27), was used instead of (1S,2R)-8-chloro-1-hydroxy-1,2,3,4-tetrahydronaphthalen-2-yl carbamate (Example 1), to obtain the title compound (0.48 g, yield 63%). $^1$H NMR (400 MHz, DMSO-d$_6$) δ 1.77-1.80 (m, 1H), 1.89-2.00 (m, 1H), 2.86-2.90 (m, 2H), 3.30 (s, 3H), 3.82-3.87 (m, 1H), 4.50 (d, J=6.8 Hz, 1H), 4.83 (d, J=6.8 Hz, 1H), 5.86 (d, J=2.8 Hz, 1H), 6.36 (br s, 2H), 7.01 (t, J=7.6 Hz, 1H), 7.18 (d, J=7.6 Hz, 1H), 7.76 (d, J=7.6 Hz, 1H).

EXAMPLE 50

(1R, 2S)-8-iodo-2-(methoxymethoxy)-1,2,3,4-tetrahydronaphthalen-1-yl carbamate

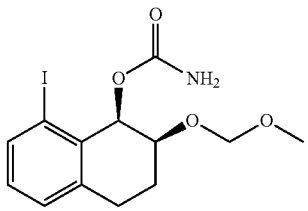 [SMILES: COCO[C@H]1CCc2cccc(I)c2[C@H]1OC(N)=O]

The substantially same method as described in Example 40 was conducted, except that (1R, 2S)-2-hydroxy-8-iodo-1,2,3,4-tetrahydronaphthalen-1-yl carbamate (Example 28), was used instead of (1S,2R)-8-chloro-1-hydroxy-1,2,3,4-tetrahydronaphthalen-2-yl carbamate (Example 1), to obtain the title compound (0.34 g, yield 60%). $^1$H NMR (400 MHz, DMSO-$d_6$) δ 1.77-1.80 (m, 1H), 1.89-2.00 (m, 1H), 2.86-2.90 (m, 2H), 3.30 (s, 3H), 3.82-3.87 (m, 1H), 4.50 (d, J=6.8 Hz, 1H), 4.83 (d, J=6.8 Hz, 1H), 5.86 (d, J=2.8 Hz, 1H), 6.36 (br s, 2H), 7.01 (t, J=7.6 Hz, 1H), 7.18 (d, J=7.6 Hz, 1H), 7.76 (d, J=7.6 Hz, 1H).

EXAMPLE 51

(1S, 2R)-7-chloro-1-hydroxy-2,3-dihydro-1H-inden-2-yl carbamate

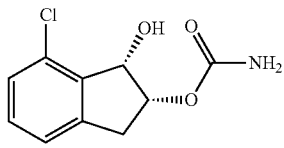 [SMILES: NC(=O)O[C@@H]1Cc2cccc(F)c2[C@@H]1O]

The substantially same method as described in Example 1 was conducted, except that (1S,2R)-7-chloro-2,3-dihydro-1H-inden-1,2-diol (Preparation example 11), was used instead of (1S, 2R)-8-chloro-1,2,3,4-tetrahydronaphthalene-1,2-diol (Preparation example 6), to obtain the title compound (0.87 g, 34%). $^1$H NMR (400 MHz, DMSO-$d_6$) δ 2.93-3.02 (m, 1H), 3.01-3.15 (m, 2H), 5.02-5.08 (m, 1H), 5.28 (s, 1H), 6.55 (s, 2H), 7.20-7.33 (m, 3H).

EXAMPLE 52

(1R, 2S)-7-chloro-1-hydroxy-2,3-dihydro-1H-inden-2-yl carbamate

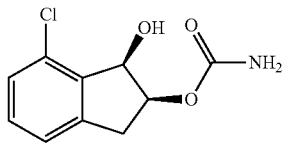

The substantially same method as described in Example 1 was conducted, except that (1R,2S)-7-chloro-2,3-dihydro-1H-inden-1,2-diol (Preparation example 14), was used instead of (1S, 2R)-8-chloro-1,2,3,4-tetrahydronaphthalene-1,2-diol (Preparation example 6), to obtain the title compound (1.22 g, 48%). $^1$H NMR (400 MHz, DMSO-$d_6$) δ 2.93-3.02 (m, 1H), 3.01-3.15 (m, 2H), 5.02-5.08 (m, 1H), 5.28 (s, 1H), 6.55 (s, 2H), 7.20-7.33 (m, 3H).

EXAMPLE 53

(1R, 2R)-7-chloro-1-hydroxy-2,3-dihydro-1H-inden-2-yl carbamate

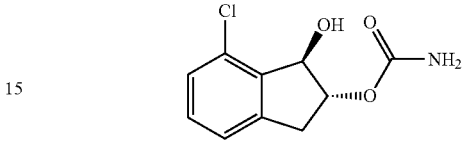

The substantially same method as described in Example 4 was conducted, except that (1R,2R)-1-((tert-butyldiphenylsilyl)oxy)-7-chloro-2,3-dihydro-1H-inden-2-yl carbamate (Preparation example 55), was used instead of (1R,2R)-1-((tert-butyldiphenylsilyl)oxy)-8-chloro-1,2,3,4-tetrahydronaphthalen-2-yl carbamate (Preparation example 27), to obtain the title compound (0.86 g, 44%). $^1$H NMR (400 MHz, CDCl$_3$) δ 3.15-3.19 (m, 2H), 4.97-5.01 (m, 1H), 5.47 (d, 1H, J=6.57 Hz), 6.11 (br s, 2H), 6.98-7.01 (m, 1H), 7.10-7.13 (m, 1H), 7.23-7.31 (m, 1H).

EXAMPLE 54

(1S, 2S)-7-chloro-1-hydroxy-2,3-dihydro-1H-inden-2-yl carbamate

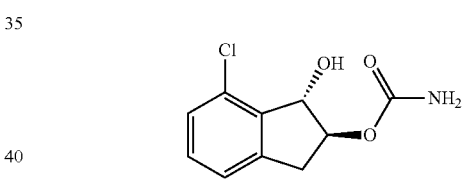

The substantially same method as described in Example 4 was conducted, except that (1S,2S)-1-((tert-butyldiphenylsilyl)oxy)-7-chloro-2,3-dihydro-1H-inden-2-yl carbamate (Preparation example 57), was used instead of (1R,2R)-1-((tert-butyldiphenylsilyl)oxy)-8-chloro-1,2,3,4-tetrahydronaphthalen-2-yl carbamate (Preparation example 27), to obtain the title compound (0.73 g, 41%). $^1$H NMR (400 MHz, CDCl$_3$) δ 3.15-3.19 (m, 2H), 4.97-5.01 (m, 1H), 5.47 (d, 1H, J=6.57 Hz), 6.11 (br s, 2H), 6.98-7.01 (m, 1H), 7.10-7.13 (m, 1H), 7.23-7.31 (m, 1H).

EXAMPLE 55

(1S, 2R)-7-fluoro-1-hydroxy-2,3-dihydro-1H-inden-2-yl carbamate

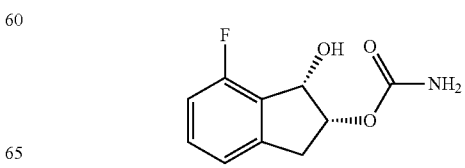

The substantially same method as described in Example 1 was conducted, except that (1S,2R)-7-fluoro-2,3-dihydro-1H-indene-1,2-diol (Preparation example 60), was used instead of (1S, 2R)-8-chloro-1,2,3,4-tetrahydronaphthalene-1,2-diol (Preparation example 6), to obtain the title compound (0.11 g, 45%). $^1$H NMR (400 MHz, CDCl$_3$) δ 2.48 (d, J=5.2, 1H), 3.14-3.28 (m, 2H), 4.83 (br s, 2H), 5.31 (q, J=6.4, 1H), 5.48 (t, J =5.2, 1H), 6.96 (t, J=8.6, 1H), 7.06 (d, J=7.6, 1H), 7.26-7.33 (m, 1H).

EXAMPLE 56

(1R, 2S)-7-fluoro-1-hydroxy-2,3-dihydro-1H-inden-2-yl carbamate

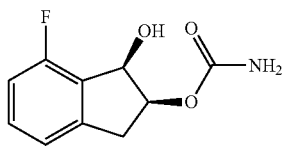 [SMILES: NC(=O)O[C@H]1Cc2cccc(F)c2[C@H]1O]

The substantially same method as described in Example 1 was conducted, except that (1R,2S)-7-fluoro-2,3-dihydro-1H-indene-1,2-diol (Preparation example 61), was used instead of (1S, 2R)-8-chloro-1,2,3,4-tetrahydronaphthalene-1,2-diol (Preparation example 6), to obtain the title compound (0.10 g, 44%). $^1$H NMR (400 MHz, CDCl$_3$) δ 2.48 (d, J=5.2, 1H), 3.14-3.28 (m, 2H), 4.83 (br s, 2H), 5.31 (q, J=6.4, 1H), 5.48 (t, J=5.2, 1H), 6.96 (t, J=8.6, 1H), 7.06 (d, J=7.6, 1H), 7.26-7.33 (m, 1H).

EXAMPLE 57

(1S, 2R)-6-chloro-1-hydroxy-2,3-dihydro-1H-inden-2-yl carbamate

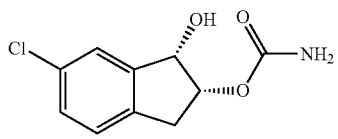 [SMILES: NC(=O)O[C@@H]1Cc2ccc(Cl)cc2[C@@H]1O]

The substantially same method as described in Example 1 was conducted, except that (1S,2R)-6-chloro-2,3-dihydro-1H-indene-1,2-diol (Preparation example 64), was used instead of (1S, 2R)-8-chloro-1,2,3,4-tetrahydronaphthalene-1,2-diol (Preparation example 6), to obtain the title compound (0.97 g, 41%). $^1$H NMR (400 MHz, CDCl$_3$) δ 3.09-3.11 (m, 2H), 4.97-5.01 (m, 1H), 5.39 (d, 1H, J=6.57 Hz), 5.88 (br s, 2H), 7.23-7.30 (m, 2H), 7.35-7.39 (m, 1H).

EXAMPLE 58

(1R, 2S)-6-chloro-1-hydroxy-2,3-dihydro-1H-inden-2-yl carbamate

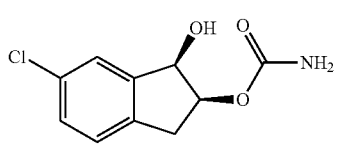 [SMILES: NC(=O)O[C@H]1Cc2ccc(Cl)cc2[C@H]1O]

The substantially same method as described in Example 1 was conducted, except that (1R,2S)-6-chloro-2,3-dihydro-1H-indene-1,2-diol (Preparation example 65), was used instead of (1S, 2R)-8-chloro-1,2,3,4-tetrahydronaphthalene-1,2-diol (Preparation example 6), to obtain the title compound (1.02 g, 43%). $^1$H NMR (400 MHz, CDCl$_3$) δ 3.09-3.11 (m, 2H), 4.97-5.01 (m, 1H), 5.39 (d, 1H, J=6.57 Hz), 5.88 (br s, 2H), 7.23-7.30 (m, 2H), 7.35-7.39 (m, 1H).

EXAMPLE 59

(1S, 2R)-5,7-dichloro-1-hydroxy-2,3-dihydro-1H-inden-2-yl carbamate

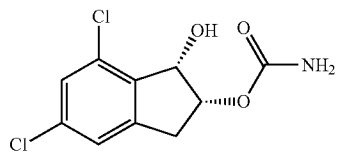 [SMILES: NC(=O)O[C@@H]1Cc2cc(Cl)cc(Cl)c2[C@@H]1O]

The substantially same method as described in Example 1 was conducted, except that (1S,2R)-5,7-dichloro-2,3-dihydro-1H-indene-1,2-diol (Preparation example 68), was used instead of (1S, 2R)-8-chloro-1,2,3,4-tetrahydronaphthalene-1,2-diol (Preparation example 6), to obtain the title compound (0.58 g, 54%). $^1$H NMR (400 MHz, CDCl$_3$) δ 2.94 (dd, J=8.0, 15.8, 1H), 3.13 (dd, J=6.6, 15.8, 1H), 3.45-3.53 (m, 1H), 4.82-4.90 (m, 1H), 5.01 (d, J=8.0, 1H), 5.80 (br s, 2H), 7.09 (d, J=1.6, 1H), 7.57 (d, J=1.58, 1H).

EXAMPLE 60

(1R, 2S)-5,7-dichloro-1-hydroxy-2,3-dihydro-1H-inden-2-yl carbamate

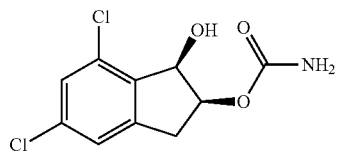 [SMILES: NC(=O)O[C@H]1Cc2cc(Cl)cc(Cl)c2[C@H]1O]

The substantially same method as described in Example 1 was conducted, except that (1R,2S)-5,7-dichloro-2,3-dihydro-1H-indene-1,2-diol (Preparation example 69), was used instead of (1S, 2R)-8-chloro-1,2,3,4-tetrahydronaphthalene-1,2-diol (Preparation example 6), to obtain the title compound (0.45 g, 47%). $^1$H NMR (400 MHz, CDCl$_3$) δ 2.94 (dd, J=8.0, 15.8, 1H), 3.13 (dd, J=6.6, 15.8, 1H), 3.45-3.53 (m, 1H), 4.82-4.90 (m, 1H), 5.01 (d, J=8.0, 1H), 5.80 (br s, 2H), 7.09 (d, J=1.6, 1H), 7.57 (d, J=1.58, 1H).

EXAMPLE 61

(1R, 2S)-4-chloro-2-hydroxy-2,3-dihydro-1H-inden-1-yl carbamate

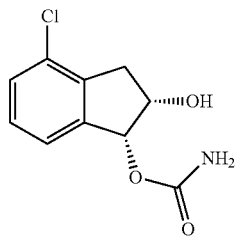 [SMILES: NC(=O)O[C@@H]1c2cccc(Cl)c2C[C@@H]1O]

The substantially same method as described in Example 1 was conducted, except that (1R,2S)-4-chloro-2,3-dihydro-1H-indene-1,2-diol (Preparation example 72), was used instead of (1S, 2R)-8-chloro-1,2,3,4-tetrahydronaphthalene-1,2-diol (Preparation example 6), to obtain the title compound (0.28 g, 26%). $^1$H NMR (400 MHz, CDCl$_3$) δ 3.03 (dd, J=6.7, 15.6, 1H), 3.08 (dd, J=1.6, 15.6, 1H), 4.60-4.67 (m, 1H), 5.97 (d, J=1.6, 1H), 6.52 (br s, 2H), 7.22 (dd, J=7.7, 8.0, 1H), 7.23 (dd, J=1.6, 8.0, 1H), 7.28 (dd, J=1.6, 7.7, 1H).

EXAMPLE 62

(1S, 2R)-4-chloro-2-hydroxy-2,3-dihydro-1H-inden-1-yl carbamate

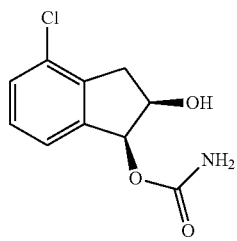 [SMILES: NC(=O)O[C@H]1c2cccc(Cl)c2C[C@H]1O]

The substantially same method as described in Example 1 was conducted, except that (1S,2R)-4-chloro-2,3-dihydro-1H-indene-1,2-diol (Preparation example 73), was used instead of (1S, 2R)-8-chloro-1,2,3,4-tetrahydronaphthalene-1,2-diol (Preparation example 6), to obtain the title compound (0.37 g, 34%). $^1$H NMR (400 MHz, CDCl$_3$) δ 3.03 (dd, J=6.7, 15.6, 1H), 3.08 (dd, J=1.6, 15.6, 1H), 4.60-4.67 (m, 1H), 5.97 (d, J=1.6, 1H), 6.52 (br s, 2H), 7.22 (dd, J=7.7, 8.0, 1H), 7.23 (dd, J=1.6, 8.0, 1H), 7.28 (dd, J=1.6, 7.7, 1H).

EXAMPLE 63

(1S, 2R)-7-chloro-2-hydroxy-2,3-dihydro-1H-inden-1-yl carbamate

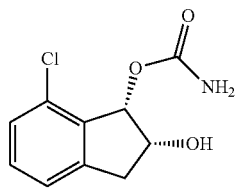 [SMILES: NC(=O)O[C@H]1c2c(Cl)cccc2C[C@H]1O]

The substantially same method as described in Example 1 was conducted, except that (1S,2R)-7-chloro-2,3-dihydro-1H-inden-1,2-diol (Preparation example 11), was used instead of (1S, 2R)-8-chloro-1,2,3,4-tetrahydronaphthalene-1,2-diol (Preparation example 6), to obtain the title compound (1.22 g, 48%). $^1$H NMR (400 MHz, CDCl$_3$) δ 2.74 (d, J=3.6, 1H), 3.03-3.13 (m, 1H), 3.18-3.27 (m, 1H), 4.62-4.68 (m, 1H), 4.8 (br s, 2H), 6.09 (d, J=5.6, 1H), 7.16 (d, J=7.2, 1H), 7.21-7.32 (m, 2H).

EXAMPLE 64

(1R, 2S)-7-chloro-2-hydroxy-2,3-dihydro-1H-inden-1-yl carbamate

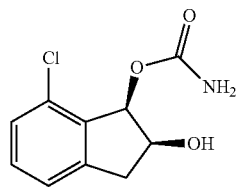 [SMILES: NC(=O)O[C@@H]1c2c(Cl)cccc2C[C@@H]1O]

The substantially same method as described in Example 1 was conducted, except that (1R,2S)-7-chloro-2,3-dihydro-1H-inden-1,2-diol (Preparation example 14), was used instead of (1S, 2R)-8-chloro-1,2,3,4-tetrahydronaphthalene-1,2-diol (Preparation example 6), to obtain the title compound (0.87 g, 34%). $^1$H NMR (400 MHz, CDCl$_3$) δ 2.74 (d, J=3.6, 1H), 3.03-3.13 (m, 1H), 3.18-3.27 (m, 1H), 4.62-4.68 (m, 1H), 4.8 (br s, 2H), 6.09 (d, J=5.6, 1H), 7.16 (d, J=7.2, 1H), 7.21-7.32 (m, 2H).

EXAMPLE 65

(1S, 2R)-5,7-dichloro-2-hydroxy-2,3-dihydro-1H-inden-1-yl carbamate

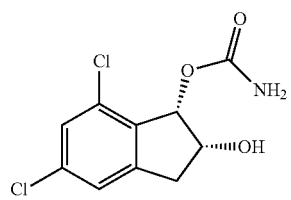 [SMILES: NC(=O)O[C@H]1c2c(Cl)cc(Cl)cc2C[C@H]1O]

The substantially same method as described in Example 1 was conducted, except that (1S,2R)-5,7-dichloro-2,3-dihydro-1H-indene-1,2-diol (Preparation example 68), was used instead of (1S, 2R)-8-chloro-1,2,3,4-tetrahydronaphthalene-1,2-diol (Preparation example 6), to obtain the title compound (0.25 g, 24%). $^1$H NMR (400 MHz, CDCl$_3$) δ 2.84 (dd, J=7.6, 16.4, 1H), 3.01 (dd, J=7.0, 16.2, 1H), 4.34-4.44 (m, 1H), 5.28 (d, J=5.6, 1H), 5.92 (d, J=5.6, 1H), 6.48 (br s, 2H), 7.33-7.37 (m, 1H), 7.43-7.47 (m, 1H).

EXAMPLE 66

(1R, 2S)-5,7-dichloro-2-hydroxy-2,3-dihydro-1H-inden-1-yl carbamate

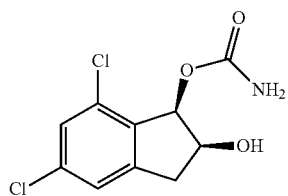 [SMILES: NC(=O)O[C@@H]1c2c(Cl)cc(Cl)cc2C[C@@H]1O]

The substantially same method as described in Example 1 was conducted, except that (1R,2S)-5,7-dichloro-2,3-dihydro-1H-indene-1,2-diol (Preparation example 69), was used instead of (1S, 2R)-8-chloro-1,2,3,4-tetrahydronaphthalene-1,2-diol (Preparation example 6), to obtain the title compound (0.34 g, 33%). $^1$H NMR (400 MHz, CDCl$_3$) δ 2.84 (dd, J=7.6, 16.4, 1H), 3.01 (dd, J=7.0, 16.2, 1H), 4.34-4.44 (m, 1H), 5.28 (d, J=5.6, 1H), 5.92 (d, J=5.6, 1H), 6.48 (br s, 2H), 7.33-7.37 (m, 1H), 7.43-7.47 (m, 1H).

EXAMPLE 67

(1R, 2S)-4-chloro-1-hydroxy-2,3-dihydro-1H-inden-2-yl carbamate

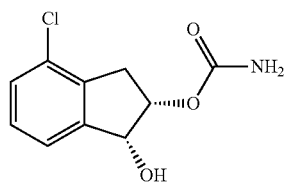 [SMILES: NC(=O)O[C@H]1Cc2c(Cl)cccc2[C@H]1O]

The substantially same method as described in Example 1 was conducted, except that (1R,2S)-4-chloro-2,3-dihydro-1H-indene-1,2-diol (Preparation example 72), was used instead of (1S, 2R)-8-chloro-1,2,3,4-tetrahydronaphthalene-1,2-diol (Preparation example 6), to obtain the title compound (0.59 g, 35%). $^1$H NMR (400 MHz, CDCl$_3$) δ 2.91 (dd, J=8.0, 15.6, 1H), 3.14 (dd, J=6.6, 15.6, 1H), 4.80-4.88 (m, 1H), 5.02 (d, J=8.0, 1H), 6.41 (br s, 2H), 7.11 (dd, J=1.7, 8.0, 1H), 7.23 (dd, J=1.7, 7.7, 1H), 7.26 (dd, J=7.7 , 8.0, 1H).

EXAMPLE 68

(1S, 2R)-4-chloro-1-hydroxy-2,3-dihydro-1H-inden-2-yl carbamate

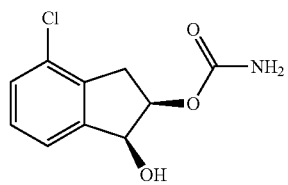 [SMILES: NC(=O)O[C@@H]1Cc2c(Cl)cccc2[C@@H]1O]

The substantially same method as described in Example 1 was conducted, except that (1S,2R)-4-chloro-2,3-dihydro-1H-indene-1,2-diol (Preparation example 73), was used instead of (1S, 2R)-8-chloro-1,2,3,4-tetrahydronaphthalene-1,2-diol (Preparation example 6), to obtain the title compound (0.28 g, 26%). $^1$H NMR (400 MHz, CDCl$_3$) δ 2.91 (dd, J=8.0, 15.6, 1H), 3.14 (dd, J=6.6, 15.6, 1H), 4.80-4.88 (m, 1H), 5.02 (d, J=8.0, 1H), 6.41 (br s, 2H), 7.11 (dd, J=1.7, 8.0, 1H), 7.23 (dd, J=1.7, 7.7, 1H), 7.26 (dd, J=7.7 , 8.0, 1H).

EXAMPLE 69

(1S, 2R)-7-fluoro-2-hydroxy-2,3-dihydro-1H-inden-1-yl carbamate

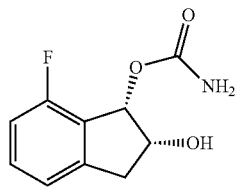

The substantially same method as described in Example 1 was conducted, except that (1S,2R)-7-fluoro-2,3-dihydro-1H-indene-1,2-diol (Preparation example 60), was used instead of (1S, 2R)-8-chloro-1,2,3,4-tetrahydronaphthalene-1,2-diol (Preparation example 6), to obtain the title compound (0.08 g, 30%). $^1$NMR (400 MHz, CDCl$_3$) δ 2.68 (d, J=3.6, 1H), 3.08 (dd, J=7.0, 15.8, 1H), 3.23 (dd, J=6.8, 16.0, 1H), 4.67-4.73 (m, 1H), 4.80 (br s, 2H), 6.16 (d, J=5.2, 1H), 6.94-6.98 (m, 1H), 7.08 (d, J=7.2, 1H), 7.32-7.37 (m, 1H).

EXAMPLE 70

(1R, 2S)-7-chloro-2-hydroxy-2,3-dihydro-1H-inden-1-yl carbamate

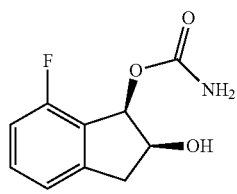 [SMILES: NC(=O)O[C@@H]1c2c(F)cccc2C[C@@H]1O]

The substantially same method as described in Example 1 was conducted, except that (1R,2S)-7-fluoro-2,3-dihydro-1H-indene-1,2-diol (Preparation example 61), was used instead of (1S, 2R)-8-chloro-1,2,3,4-tetrahydronaphthalene-1,2-diol (Preparation example 6), to obtain the title compound (0.11 g, 40%). $^1$H NMR (400 MHz, CDCl$_3$) δ 2.68 (d, J=3.6, 1H), 3.08 (dd, J=7.0, 15.8, 1H), 3.23 (dd, J=6.8, 16.0, 1H), 4.67-4.73 (m, 1H), 4.80 (br s, 2H), 6.16 (d, J=5.2, 1H), 6.94-6.98 (m, 1H), 7.08 (d, J=7.2, 1H), 7.32-7.37 (m, 1H).

EXAMPLE 71

(1S, 2R)-7-chloro-1-(methoxymethoxy)-2,3-dihydro-1H-inden-2-yl carbamate

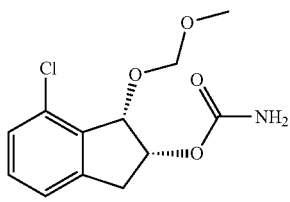 [SMILES: COCO[C@H]1c2c(Cl)cccc2C[C@H]1OC(N)=O]

The substantially same method as described in Example 40 was conducted, except that (1S, 2R)-7-chloro-1-hydroxy-2,3-dihydro-1H-inden-2-yl carbamate (Example 51), was used instead of (1S,2R)-8-chloro-1-hydroxy-1,2,3,4-tetrahydronaphthalen-2-yl carbamate (Example 1), to obtain the title compound (1.22 g, 65%). $^1$H NMR (400 MHz, CDCl$_3$) δ 3.15-3.29 (m, 2H), 3.45 (s, 3H), 4.73 (br s, 2H), 4.81 (d, J=6.4 Hz, 1H), 4.92 (d, J=6.4 Hz, 1H), 5.23-5.30 (m, 2H), 7.14-7.16 (m, 1H), 7.23-7.25 (m, 2H).

EXAMPLE 72

(1R, 2S)-7-chloro-1-(methoxymethoxy)-2,3-dihydro-1H-inden-2-yl carbamate

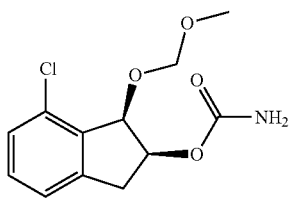 [SMILES: COCO[C@@H]1c2c(Cl)cccc2C[C@@H]1OC(N)=O]

The substantially same method as described in Example 40 was conducted, except that (1R, 2S)-7-chloro-1-hydroxy-2,3-dihydro-1H-inden-2-yl carbamate (Example 52), was used instead of (1S,2R)-8-chloro-1-hydroxy-1,2,3,4-tetrahydronaphthalen-2-yl carbamate (Example 1), to obtain the title compound (1.13 g, 62%). $^1$H NMR (400 MHz, CDCl$_3$) δ 3.15-3.29 (m, 2H), 3.45 (s, 3H), 4.73 (br s, 2H), 4.81 (d, J=6.4 Hz, 1H), 4.92 (d, J=6.4 Hz, 1H), 5.23-5.30 (m, 2H), 7.14-7.16 (m, 1H), 7.23-7.25 (m, 2H).

EXAMPLE 73

(1S, 2R)-7-fluoro-1-(methoxymethoxy)-2,3-dihydro-1H-inden-2-yl carbamate

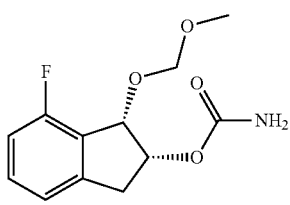 [SMILES: COCO[C@H]1c2c(F)cccc2C[C@H]1OC(N)=O]

The substantially same method as described in Example 40 was conducted, except that (1S, 2R)-7-fluoro-1-hydroxy-2,3-dihydro-1H-inden-2-yl carbamate (Example 55), was used instead of (1S,2R)-8-chloro-1-hydroxy-1,2,3,4-tetrahydronaphthalen-2-yl carbamate (Example 1), to obtain the title compound (0.28 g, 45%). $^1$H NMR (400 MHz, DMSO-d$_6$) δ 2.99 (dd, J=6.8, 15.6, 1H), 3.15 (dd, J=6.8, 15.6, 1H), 3.30 (s, 3H), 4.67 (q, J=6.5, 2H), 5.07-5.16 (m, 1H), 5.24 (d, J=4.8, 1H), 6.53-6.78 (br s, 2H), 7.05 (t, J=8.8, 1H), 7.13 (d, J=7.6, 1H), 7.32-7.38 (m, 1H).

EXAMPLE 74

(1R, 2S)-7-fluoro-1-(methoxymethoxy)-2,3-dihydro-1H-inden-2-yl carbamate

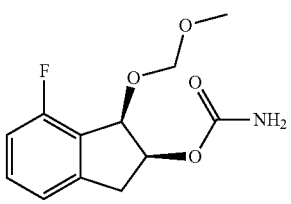 [SMILES: COCO[C@@H]1c2c(F)cccc2C[C@@H]1OC(N)=O]

The substantially same method as described in Example 40 was conducted, except that (1R, 2S)-7-fluoro-1-hydroxy-2,3-dihydro-1H-inden-2-yl carbamate (Example 56), was used instead of (1S,2R)-8-chloro-1-hydroxy-1,2,3,4-tetrahydronaphthalen-2-yl carbamate (Example 1), to obtain the title compound (0.14 g, 45%). $^1$H NMR (400 MHz, DMSO-d$_6$) δ 2.99 (dd, J=6.8, 15.6, 1H), 3.15 (dd, J=6.8, 15.6, 1H), 3.30 (s, 3H), 4.67 (q, J=6.5, 2H), 5.07-5.16 (m, 1H), 5.24 (d, J=4.8, 1H), 6.53-6.78 (br s, 2H), 7.05 (t, J=8.8, 1H), 7.13 (d, J=7.6, 1H), 7.32-7.38 (m, 1H).

EXAMPLE 75

(1S, 2R)-7-chloro-2-(methoxymethoxy)-2,3-dihydro-1H-inden-1-yl carbamate

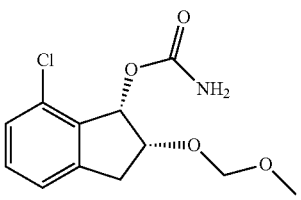 [SMILES: COCO[C@@H]1Cc2cccc(Cl)c2[C@@H]1OC(N)=O]

The substantially same method as described in Example 40 was conducted, except that (1S, 2R)-7-chloro-2-hydroxy-2,3-dihydro-1H-inden-1-yl carbamate (Example 63), was used instead of (1S,2R)-8-chloro-1-hydroxy-1,2,3,4-tetrahydronaphthalen-2-yl carbamate (Example 1), to obtain the title compound (1.44 g, 62%). $^1$H NMR (400 MHz, CDCl$_3$) δ 3.10-3.24 (m, 2H), 3.40 (s, 3H), 4.41-4.50 (m, 1H), 4.66 (d, J=6.8, 1H), 4.84 (d, J=6.8, 1H), 4.99 (br s, 2H), 6.27 (d, J=5.6, 1H), 7.14 (d, J=6.8, 1H), 7.20-7.29 (m, 2H).

EXAMPLE 76

(1R, 2S)-7-chloro-2-(methoxymethoxy)-2,3-dihydro-1H-inden-1-yl carbamate

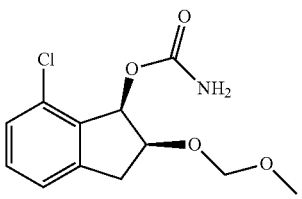 [SMILES: COCO[C@H]1Cc2cccc(Cl)c2[C@H]1OC(N)=O]

The substantially same method as described in Example 40 was conducted, except that (1R, 2S)-7-chloro-2-hydroxy-2,3-dihydro-1H-inden-1-yl carbamate (Example 64), was used instead of (1S,2R)-8-chloro-1-hydroxy-1,2,3,4-tetrahydronaphthalen-2-yl carbamate (Example 1), to obtain the title compound (1.62 g, 68%). $^1$H NMR (400 MHz, CDCl$_3$) δ 3.10-3.24 (m, 2H), 3.40 (s, 3H), 4.41-4.50 (m, 1H), 4.66 (d, J=6.8, 1H), 4.84 (d, J=6.8, 1H), 4.99 (br s, 2H), 6.27 (d, J=5.6, 1H), 7.14 (d, J=6.8, 1H), 7.20-7.29 (m, 2H).

EXAMPLE 77

(1S, 2R)-7-chloro-2,3-dihydro-1H-inden-1,2-diyl dicarbamate

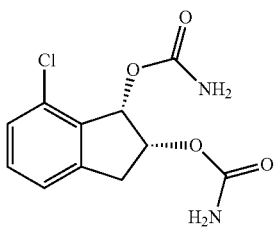 [SMILES: NC(=O)O[C@@H]1Cc2cccc(Cl)c2[C@@H]1OC(N)=O]

The substantially same method as described in Example 1 was conducted, except that (1S, 2R)-7-chloro-1-hydroxy-2,3-dihydro-1H-inden-2-yl carbamate (Example 51), was used instead of (1S, 2R)-8-chloro-1,2,3,4-tetrahydronaphthalene-1,2-diol (Preparation example 6), to obtain the title compound (0.22 g, 48%). $^1$H NMR (400 MHz, DMSO-d$_6$) δ 2.96-3.01 (m, 1H), 5.30 (q, 1H, J=6.8 Hz), 6.16 (d, 1H, J=5.6 Hz), 6.51 (br s, 4H), 7.27-7.38 (m, 3H).

EXAMPLE 78

(1R, 2S)-7-chloro-2,3-dihydro-1H-inden-1,2-diyl dicarbamate

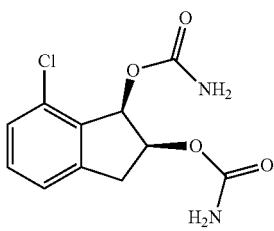 [SMILES: NC(=O)O[C@H]1Cc2cccc(Cl)c2[C@H]1OC(N)=O]

The substantially same method as described in Example 1 was conducted, except that (1R, 2S)-7-chloro-1-hydroxy-2,3-dihydro-1H-inden-2-yl carbamate (Example 52), was used instead of (1S, 2R)-8-chloro-1,2,3,4-tetrahydronaphthalene-1,2-diol (Preparation example 6), to obtain the title compound (0.15 g, 41%). $^1$H NMR (400 MHz, DMSO-d$_6$) δ 2.96-3.01 (m, 1H), 5.30 (q, 1H, J=6.8 Hz), 6.16 (d, 1H, J=5.6 Hz), 6.51 (br s, 4H), 7.27-7.38 (m, 3H).

EXAMPLE 79

(1R, 2S)-4-chloro-2,3-dihydro-1H-inden-1,2-diyl dicarbamate

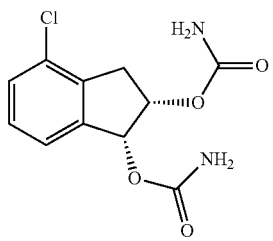 [SMILES: NC(=O)O[C@H]1Cc2c(Cl)cccc2[C@H]1OC(N)=O]

The substantially same method as described in Example 1 was conducted, except that (1R, 2S)-4-chloro-2-hydroxy-2,3-dihydro-1H-inden-1-yl carbamate (Example 61), was used instead of (1S, 2R)-8-chloro-1,2,3,4-tetrahydronaphthalene-1,2-diol (Preparation example 6), to obtain the title compound (0.45 g, 80%). $^1$H NMR (400 MHz, DMSO-d$_6$) δ 2.88 (dd, J=3.8, 16.6, 1H), 3.24 (dd, J=5.8, 16.6, 1H), 5.33-5.37 (m, 1H), 6.00 (d, J=5.2, 1H), 6.62 (br s, 4H), 7.25-7.32 (m, 2H), 7.38 (dd, J=1.2, 7.6, 1H).

EXAMPLE 80

(1S, 2R)-4-chloro-2,3-dihydro-1H-inden-1,2-diyl dicarbamate

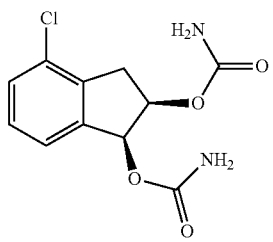 [SMILES: NC(=O)O[C@@H]1Cc2c(Cl)cccc2[C@@H]1OC(N)=O]

The substantially same method as described in Example 1 was conducted, except that (1S, 2R)-4-chloro-2-hydroxy-2,3-dihydro-1H-inden-1-yl carbamate (Example 62), was used instead of (1S, 2R)-8-chloro-1,2,3,4-tetrahydronaphthalene-1,2-diol (Preparation example 6), to obtain the title compound (0.49 g, 83%). $^1$H NMR (400 MHz, DMSO-d$_6$) δ 2.88 (dd, J=3.8, 16.6, 1H), 3.24 (dd, J=5.8, 16.6, 1H), 5.33-5.37 (m, 1H), 6.00 (d, J=5.2, 1H), 6.62 (br s, 4H), 7.25-7.32 (m, 2H), 7.38 (dd, J=1.2, 7.6, 1H).

EXAMPLE 81

(1S, 2R)-6-chloro-2,3-dihydro-1H-inden-1,2-diyl dicarbamate

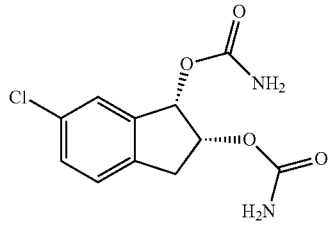 [SMILES: NC(=O)O[C@@H]1Cc2ccc(Cl)cc2[C@@H]1OC(N)=O]

The substantially same method as described in Example 1 was conducted, except that (1S, 2R)-6-chloro-1-hydroxy-2,3-dihydro-1H-inden-2-yl carbamate (Example 57), was used instead of (1S, 2R)-8-chloro-1,2,3,4-tetrahydronaphthalene-1,2-diol (Preparation example 6), to obtain the title compound (0.56 g, 78%). $^1$H NMR (400 MHz, CDCl$_3$) δ 2.88 (dd, J=4.4, 16.4, 1H), 3.17 (dd, J=6.0, 16.4, 1H), 5.27-5.34 (m, 1H), 5.92 (d, J=5.2, 1H), 6.38-6.75 (m, 4H), 7.28-7.38 (m, 3H).

EXAMPLE 82

(1R, 2S)-6-chloro-2,3-dihydro-1H-inden-1,2-diyl dicarbamate

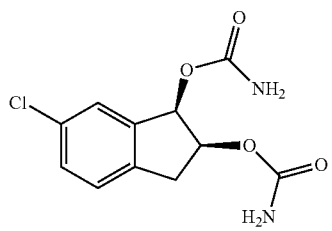 [SMILES: NC(=O)O[C@H]1Cc2ccc(Cl)cc2[C@H]1OC(N)=O]

The substantially same method as described in Example 1 was conducted, except that (1R, 2S)-6-chloro-1-hydroxy-2,3-dihydro-1H-inden-2-yl carbamate (Example 58), was used instead of (1S, 2R)-8-chloro-1,2,3,4-tetrahydronaphthalene-1,2-diol (Preparation example 6), to obtain the title compound (0.48 g, 75%). $^1$H NMR (400 MHz, CDCl$_3$) δ 2.88 (dd, J=4.4, 16.4, 1H), 3.17 (dd, J=6.0, 16.4, 1H), 5.27-5.34 (m, 1H), 5.92 (d, J=5.2, 1H), 6.38-6.75 (m, 4H), 7.28-7.38 (m, 3H).

EXAMPLE 83

(1S, 2R)-5,7-dichloro-2,3-dihydro-1H-inden-1,2-diyl dicarbamate

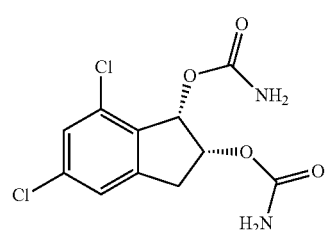

The substantially same method as described in Example 1 was conducted, except that (1S, 2R)-5,7-dichloro-1-hydroxy-2,3-dihydro-1H-inden-2-yl carbamate (Example 59), was used instead of (1S, 2R)-8-chloro-1,2,3,4-tetrahydronaphthalene-1,2-diol (Preparation example 6), to obtain the title compound (1.1 g, 83%). $^1$H NMR (400 MHz, CDCl$_3$) δ 2.96 (dd, J=6.8, 16.4, 1H), 3.25 (dd, J=7.2, 16.4, 1H), 5.25-5.32 (m, 1H), 6.14 (d, J=5.6, 1H), 6.55 (s, 4H), 7.39-7.42 (m, 1H), 7.47-7.50 (m, 1H).

EXAMPLE 84

(1R, 2S)-5,7-dichloro-2,3-dihydro-1H-inden-1,2-diyl dicarbamate

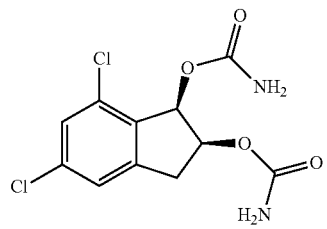 [SMILES: NC(=O)O[C@H]1Cc2cc(Cl)cc(Cl)c2[C@H]1OC(N)=O]

The substantially same method as described in Example 1 was conducted, except that (1R, 2S)-5,7-dichloro-1-hydroxy-2,3-dihydro-1H-inden-2-yl carbamate (Example 60), was used instead of (1S, 2R)-8-chloro-1,2,3,4-tetrahydronaphthalene-1,2-diol (Preparation example 6), to obtain the title compound (0.89 g, 81%). $^1$H NMR (400 MHz, CDCl$_3$) δ 2.96 (dd, J=6.8, 16.4, 1H), 3.25 (dd, J=7.2, 16.4, 1H), 5.25-5.32 (m, 1H), 6.14 (d, J=5.6, 1H), 6.55 (s, 4H), 7.39-7.42 (m, 1H), 7.47-7.50 (m, 1H).

EXAMPLE 85

(1S, 2R)-7-fluoro-2,3-dihydro-1H-inden-1,2-diyl dicarbamate

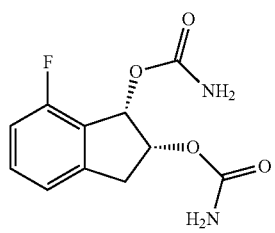 [SMILES: NC(=O)O[C@@H]1Cc2cccc(F)c2[C@@H]1OC(N)=O]

The substantially same method as described in Example 1 was conducted, except that (1S, 2R)-7-fluoro-1-hydroxy-2,3-dihydro-1H-inden-2-yl carbamate (Example 55), was used instead of (1S, 2R)-8-chloro-1,2,3,4-tetrahydronaphthalene-1,2-diol (Preparation example 6), to obtain the title compound (0.85 g, 77%). $^1$H NMR (400 MHz, DMSO-d$_6$) δ 2.94 (dd, J=5.8, 16.2, 1H), 3.22 (dd, J=4.6, 18.2, 1H), 5.30 (q, J=5.9, 1H), 6.22 (d, J=5.2, 1H), 6.53 (br s, 4H), 7.05 (t, J=8.8, 1H), 7.14 (d, J=7.6, 1H), 7.34-7.39 (m, 1H).

EXAMPLE 86

(1R, 2S)-7-fluoro-2,3-dihydro-1H-inden-1,2-diyl dicarbamate

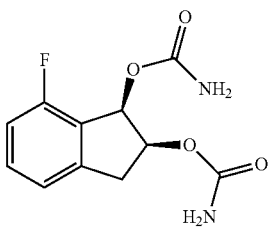 [SMILES: NC(=O)O[C@H]1Cc2cccc(F)c2[C@H]1OC(N)=O]

The substantially same method as described in Example 1 was conducted, except that (1R, 2S)-7-fluoro-1-hydroxy-2,3-dihydro-1H-inden-2-yl carbamate (Example 56), was used instead of (1S, 2R)-8-chloro-1,2,3,4-tetrahydronaphthalene-1,2-diol (Preparation example 6), to obtain the title compound (0.94 g, 78%). $^1$H NMR (400 MHz, DMSO-d$_6$) δ 2.94 (dd, J=5.8, 16.2, 1H), 3.22 (dd, J=4.6, 18.2, 1H), 5.30 (q, J=5.9, 1H), 6.22 (d, J=5.2, 1H), 6.53 (br s, 4H), 7.05 (t, J=8.8, 1H), 7.14 (d, J=7.6, 1H), 7.34-7.39 (m, 1H).

EXAMPLE 87

(1S,2R)-8-chloro-1-methoxy-1,2,3,4-tetrahydronaphthalen-2-yl carbamate

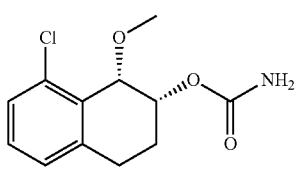 [SMILES: CO[C@H]1c2c(Cl)cccc2CC[C@H]1OC(N)=O]

To a stirred solution of (1S,2R)-8-chloro-1-methoxy-1,2,3,4-tetrahydronaphthalen-2-ol (Preparation example 76, 0.9 g, 4.42 mmol) in THF (21 mL) was added 1,1'-carbonyldiimidazole (1.4 g, 8.84 mmol) at room temperature for 14 hr. The mixture was added NH$_4$OH (14.5 mL, 88.30 mmol) then the mixture was stirred at room temperature for 14 hr. The resulting mixture was neutralized by 1N aq. HCl to pH 7, extracted with EtOAc. The combined organic layer was washed with water, dried over MgSO$_4$, and evaporated under reduced pressure. The concentrated residue was purified by a silica gel column chromatography, to obtain the title compound (0.9 g, yield 84%). $^1$H NMR (400 MHz, DMSO-d$_6$) δ 1.78-1.83 (m, 1H), 1.98-2.13 (m, 1H), 2.81-2.96 (m, 2H), 3.57 (s, 3H), 4.63-4.64 (m, 1H), 4.71 (td, J=12.5, 3.3 Hz, 1H), 7.11-7.13 (m, 1H), 7.26 (t, J=7.6 Hz, 1H), 7.31-7.33 (m, 1H).

EXAMPLE 88

(1S,2R)-8-chloro-1-methoxy-1,2,3,4-tetrahydronaphthalen-2-yl isopropylcarbamate

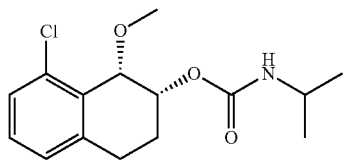 [SMILES: CO[C@H]1c2c(Cl)cccc2CC[C@H]1OC(=O)NC(C)C]

To a stirred solution of (1S,2R)-8-chloro-1-methoxy-1,2,3,4-tetrahydronaphthalen-2-ol (Preparation example 76, 1.0 g, 4.75 mmol) in THF (24 mL) was added 1,1'-carbonyldiimidazole (1.0 g, 9.50 mmol) at room temperature for 14 hr. The mixture was added isopropylamine (0.8 mL, 9.50 mmol) then the mixture was stirred at room temperature for 14 hr. The resulting mixture was diluted with EtOAc, washed with water, dried over MgSO$_4$, and evaporated under reduced pressure. The concentrated residue was purified by a silica gel column chromatography, to obtain the title compound (0.9 g, yield 83%). $^1$H NMR (400 MHz, DMSO-d$_6$) δ 1.07 (d, J=6.4 Hz, 6H), 1.80-1.82 (m, 1H), 2.03-2.09 (m, 1H), 2.81-2.96 (m, 2H), 3.56 (s, 3H), 3.61-3.65 (m, 1H), 4.65-4.66 (m, 1H), 4.73 (td, J=12.5, 3.3 Hz, 1H), 7.11-7.13 (m, 1H), 7.26 (t, J=7.6 Hz, 1H), 7.31-7.32 (m, 1H).

EXAMPLE 89

(1S,2R)-8-chloro-1-(methoxymethoxy)-1,2,3,4-tetrahydronaphthalen-2-yl isopropylcarbamate

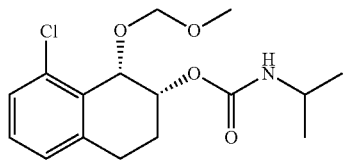 [SMILES: COCO[C@H]1c2c(Cl)cccc2CC[C@H]1OC(=O)NC(C)C]

To a stirred solution of (1S,2R)-8-chloro-1-(methoxymethoxy)-1,2,3,4-tetrahydronaphthalen-2-ol (Preparation example 78, 2.3 g, 9.27 mmol) in THF (46 mL) was added 1,1'-carbonyldiimidazole (3.0 g, 18.54 mmol) at room temperature for 14 hr. The mixture was added isopropylamine (1.6 mL, 18.54 mmol) then the mixture was stirred at room temperature for 14 hr. The resulting mixture was diluted with EtOAc, washed with water, dried over MgSO$_4$, and evaporated under reduced pressure. The concentrated residue was purified by a silica gel column chromatography, to obtain the title compound (2.5 g, yield 92%). $^1$H NMR (400 MHz, DMSO-d$_6$) δ 1.07-1.09 (m, 6H), 1.83-1.86 (m, 1H), 2.13-2.20 (m, 1H), 2.86-2.95 (m, 1H), 2.99-3.04 (m, 1H), 3.29 (s, 3H), 3.61-3.67 (m, 1H), 4.66-4.70 (m, 2H), 4.86 (d, J=6.0 Hz, 1H), 5.07 (d, J=1.6 Hz, 1H), 7.14-7.20 (m, 2H), 7.26-7.33 (m, 2H).

EXAMPLE 90

(1S,2R)-8-chloro-1-hydroxy-1,2,3,4-tetrahydronaphthalen-2-yl isopropylcarbamate

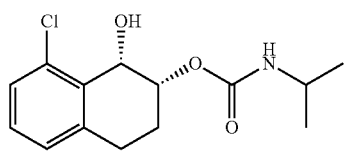 [SMILES: CC(C)NC(=O)O[C@@H]1CCc2cccc(Cl)c2[C@@H]1O]

To a stirred solution of (1S,2R)-8-chloro-1-(methoxymethoxy)-1,2,3,4-tetrahydronaphthalen-2-yl isopropylcarbamate (Example 89, 1.6 g, 4.85 mmol) in MeOH (24 mL) was added 6N HCl solution (3.2 mL, 19.08 mmol) at room temperature for 14 hr. The resulting mixture was neutralized with sat. NaHCO$_3$, extracted with EtOAc, washed with water and brine, dried over MgSO$_4$, and concentrated under reduced pressure. The concentrated residue was purified by a silica gel column chromatography, to obtain the title compound (1.2 g, yield 87%). $^1$H NMR (400 MHz, DMSO-d$_6$) δ 1.05-1.09 (m, 6H), 1.71-1.74 (m, 1H), 2.08-2.20 (m, 1H), 2.82-2.96 (m, 2H), 3.60-3.65 (m, 1H), 4.61 (td, J=12.7, 3.3 Hz, 1H), 4.94 (br s, 1H), 5.23 (d, J=6.0 Hz, 1H), 7.09-7.12 (m, 2H), 7.22-7.30 (m, 2H).

EXAMPLE 91

(1S,2R)-8-chloro-2-hydroxy-1,2,3,4-tetrahydronaphthalen-1-yl isopropylcarbamate

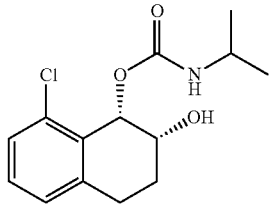 [SMILES: CC(C)NC(=O)O[C@H]1c2c(Cl)cccc2CC[C@H]1O]

To a stirred solution of (1S,2R)-2-((tert-butyldimethylsilyl)oxy)-8-chloro-1,2,3,4-tetrahydronaphthalen-1-yl isopropylcarbamate (Preparation example 79, 2.9 g, 7.29 mmol) in MeOH (73 mL) was added 6N HCl solution (2.4 mL, 14.57 mmol) at room temperature for 14 hr. The resulting mixture was neutralized with sat. NaHCO$_3$, extracted with EtOAc, washed with water and brine, dried over MgSO$_4$, and concentrated under reduced pressure. The concentrated residue was purified by a silica gel column chromatography, to obtain the title compound (1.8 g, yield 89%). $^1$H NMR (400 MHz, CDCl$_3$) δ 1.16-1.18 (m, 6H), 1.92-1.98 (m, 2H), 2.79-2.88 (m, 1H), 2.93-2.97 (m, 1H), 3.67 (s, 1H), 3.81-3.90 (m, 1H), 4.02-4.04 (m, 1H), 4.71 (d, J=7.2 Hz, 1H), 6.13 (d, J=3.2 Hz, 1H), 7.07 (d, J=7.2 Hz, 1H), 7.19-7.27 (m, 2H).

EXAMPLE 92

(1S,2R)-8-chloro-2-methoxy-1,2,3,4-tetrahydronaphthalen-1-yl isopropylcarbamate

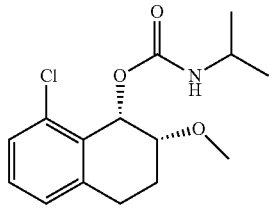 [SMILES: CO[C@@H]1CCc2cccc(Cl)c2[C@@H]1OC(=O)NC(C)C]

To a stirred solution of (1S,2R)-8-chloro-2-hydroxy-1,2,3,4-tetrahydronaphthalen-1-yl isopropylcarbamate (Preparation example 91, 0.9 g, 3.00 mmol) in THF (13 mL) was portionwise added potassium tert-butoxide (0.5 g, 4.49 mmol) at 0° C. then allowed to stir for 10 min. The mixture was added CH$_3$I (0.9 mL, 14.98 mmol) at 0° C. When the reaction was completed, the resulting mixture was diluted with EtOAc, washed with water, dried over Na$_2$SO$_4$, filtered, and concentrated under reduced pressure to produce the title compound (0.5 g, yield 55%). $^1$H NMR (400 MHz, CDCl$_3$) δ 1.15 (d, J=6.4 Hz, 6H), 1.94-2.07 (m, 2H), 2.82-2.89 (m, 1H), 2.96-3.01 (m, 1H), 3.45 (td, J=11.7, 3.7 Hz, 1H), 3.57 (s, 3H), 3.84 (br s, 1H), 6.42 (d, J=1.6 Hz, 1H), 7.05 (d, J=7.6 Hz, 1H), 7.19 (t, J=7.8 Hz, 1H), 7.27 (d, J=6.0 Hz, 1H).

EXAMPLE 93

(1S,2R)-8-chloro-2-(methoxymethoxy)-1,2,3,4-tetrahydronaphthalen-1-yl isopropylcarbamate

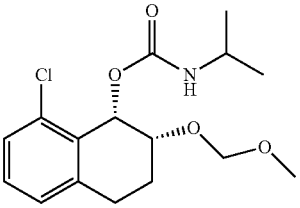 [SMILES: COCO[C@@H]1CCc2cccc(Cl)c2[C@@H]1OC(=O)NC(C)C]

To a stirred solution of (1S,2R)-8-chloro-2-hydroxy-1,2,3,4-tetrahydronaphthalen-1-yl isopropylcarbamate (Example 91, 0.8 g, 2.83 mmol) in dichloromethane (14 mL) was added diisopropylethylamine (1.8 mL, 14.13 mmol) at 0° C. then allowed to stir for 20 min. The mixture was added chloromethyl methyl ether (1.1 mL, 14.13 mmol) 0° C. When the reaction was completed, the resulting mixture was quenched with water, diluted with EtOAc, washed with water and brine, dried over MgSO$_4$, filtered and concentrated under reduced pressure. The crude product was purified by silica gel column chromatography, to obtain the title compound (0.5 g, yield 49%). $^1$H NMR (400 MHz, CDCl$_3$) δ 1.15 (d, J=6.4 Hz, 6H), 1.92-1.96 (m, 1H), 2.02-2.13 (m, 1H), 2.87-2.93 (m, 1H), 2.95-3.03 (m, 1H), 3.44 (s, 3H), 3.83-3.84 (m, 1H), 3.96 (td, J=12.4, 3.6 Hz, 1H), 4.47 (br s, 1H), 4.63 (d, J=7.2 Hz, 1H), 5.01 (d, J=7.2 Hz, 1H), 6.33 (br s, 1H), 7.06 (d, J=7.6 Hz, 1H), 7.20 (t, J=7.8 Hz, 1H), 7.26-7.28 (m, 1H).

BIOLOGICAL EXPERIMENTAL EXAMPLE 1

Evaluation of Antiallodynic Activity on Post Operative-Induced Pain Model (PO)

Male Sprague-Dawley rats (Orient Bio, Korea, 230-250g) were habituated at least 3 days before surgery, and were allowed free access to food and water throughout the experimentation. Room temperature and humidity were maintained at 24±2 and 50±10%, respectively. The process of performing the post-operation model's surgery was adapted from Brennan et al (1996). At first, rats with allodynia (threshold valueless than 8 g) were excluded in Pre-von Frey Test. During the post-operation surgery, rats were anesthetized under gaseous anesthesia with 2% isoflurane. The rat was placed, lying face down, on 37 degree warm plate to prevent against hypothermia. The ipsilateral plantar aspect (left side) of the hind paw was prepared in a sterile manner with a 10% povidone-iodine solution. A 1 cm longitudinal incision was made with a number 10 blade, through the skin and fascia of the ipsilateral plantar aspect of the foot, starting from 0.5 cm from the proximal edge of the heel and extending toward the toes. Rats' plantar muscles were elevated and incised longitudinally. After hemostasis with gentle pressure, the skin was opposed with 2 mattress sutures of 4-0 Dafilon.

After 24 hr of recovery, rats with a good response (threshold less than 4 g) in Pre-von Frey Test were selected. According to this response, we made three groups with each group having equal average responses: Group 1, post-operation and drug treated; Group 2, post-operation and vehicle treated; Group 3, no post-operation and vehicle treated. In this study, Group 3 was the sham control (positive) group. The group 2 was used to check for possible failures to generate post-operative pain.

For efficacy measure, the threshold value of group C was assigned 100% efficacy, and the percentage of the threshold values of group A compared to group C (for each different dose level) were calculated as the efficacies. Base on these efficacy values, ED50 was calculated using log fitting. If there was no clear ED50, then we marked the percent efficacy at the highest tested dose or larger than highest tested dose.

For pain threshold test, all animals were placed in a stainless steel meshed chamber and habituated for 30 min in the test cage. The tactile sensitivity of the ipsilateral hind paw was measured using the up-and-down method (Dixon, 1980) with seven von Frey monofilaments (0.4, 1, 2, 4, 6, 8, and 15 g) using 3 trials. The 50% paw withdrawal threshold for each paw was calculated using the following formula: [Xth] log=[vFr] log+ky, where [vFr] is the force of the last von Frey filament used, k=0.2249 which is the average interval (in log units) between the von Frey monofilaments, y which is a value that depends upon the pattern of withdrawal responses, and Xth which is the threshold value (Dixon, 1980). If an animal did not respond to the highest von Frey hair (15 g), then the threshold value was assigned as 18.4g.

Drugs were dissolved 30% PEG400 or 20% tween80 for compounds.

The relative values compared to the sham (% control) were calculated and shown in Table 2, which show an antiallodynic effect of the compound of examples on Post operation-induced pain model in rats.

TABLE 2

Antiallodynic effect of compound examples on PO model

| Compound No. | Post OperationEfficacy dose(mg/kg) |
|---|---|
| 1 | 200 (29.8%) |

BIOLOGICAL EXPERIMENTAL EXAMPLE 2

Writhing Test

To examine the pain relief effect of the carbamate compounds, a writhing test was conducted, referring to Fischer, L. G. et al. (2008).

ICR mice (male, 24-28g; Orient Bio, Korea) were habituated before test (in test room) for 1 hour. Animals were fasted 2 hr before administration of compounds. Each of compounds was orally administered at the three dose, 10 ul/g, bw (n=3-5/group). All compounds were dissolved in a vehicle of 30% (v/v) PEG 400 or 20% (v/v) Tween 80. The control group was treated the vehicle without compounds.

0.2-2 hour after the administration of compounds, 0.6% acetic acid at the dose of 10 ul/g by bodyweight was injected into the mice Animals were habituated in the cage for 5 min. 5 min after habituation, the number of writhes (abdominal constriction) was counted for 15 min, referring to Korzeniewska-Rybicka, I. et al. (1998) and compared with that of a control.

The relative values compared to the control (% control) were calculated and shown in
Table 3.

TABLE 3

Effect of compound examples in writhing test.

| | Writhing test(po) | |
|---|---|---|
| Example No. | ED50(mg/kg) | Peak Time(hr) |
| 1 | 46.1 | 1 |
| 18 | 55.6 | 0.5 |
| 19 | 30 | 1 |

BIOLOGICAL EXPERIMENTAL EXAMPLE 3

Evaluation of Antiallodynic Activity on Chung Model

Male Sprague-Dawley rats (100-130 g, Orient Bio, Korea) were habituated for 1 week before the experiment, and allowed free access to food and water throughout the experimentation. Room temperature and humidity were maintained at 24±2 and 50±10%, respectively. The neuropathic surgery (SNL, Spinal nerve ligation) model was done as described in Kim and Chung (1992). Briefly, an animal was put under gaseous anesthesia with isoflurane. The left lumber spinal nerve L5 and L6 were isolated and tightly ligated with 6-0 silk thread. The wound muscle was closed with Catgut® chrom 3/0 thread and skin was closed with Dafilon 3/0 tread Sham controls were prepared in the same manner with the spinal nerves were exposed, but with no ligated L5 and L6 nerves. Preparation of the vehicle controls were indetical to the group treated with compound, except for administration of vehicles without compound in the vehicle control group.

Tactile sensitivity (Mechanical allodynia) was evaluated using von Frey monofilaments before and after treatment, and animals were included in the study only if the withdrawal threshold value was less than 4 g. One week after surgery, SNL-operated animals, sham-operated animals and vehicle control animals were tested for tactile sensitivity with von Frey monofilaments 3 trials in each animal All Animals were placed in a stainless steel mash chamber and habituated for 30 min in the test cage. The tactile sensitivity for the ipsilateral hind paw was measured using the up-and-down method (Dixon, 1980) with seven von Frey monofilaments (0.4, 1, 2, 4, 6, 8, and 15 g) in 3 trials. The tactile sensitivity test was followed by Dixon's method (Dixon, 1980). The 50% paw withdrawal threshold for each paw was calculated using the following formula: [Xth]log=[vFr]log+ky where [vFr] is the force of the last von Frey used, k=0.2249 which is the average interval (in log units) between the von Frey monofilaments, and y is a value that depends upon the pattern of withdrawal responses (Dixon, 1980). If an animal did not respond to the highest von Frey hair (15 g), then the paw was assigned a value of 18.4 g.

All animals were fasted 18 h before the administration of the compounds. Antiallodynic effect of tested compounds were evaluated at the three dose, orally administered in a volume of 5 ul/g, bw in a vehicle of 30% (v/v) PEG 400 or 20% (v/v) Tween 80. The test was performed at the peak time of efficacy) after compound administration.

The relative values compared to the sham group (% control) were calculated and shown in Table 4, which show an antiallodynic effect of the test compounds on SNL model in rats.

TABLE 4

Antiallodynic effect of compound examples on SNL model

| Example No. | SNL ED50(mg/kg) | Peak Time(h) |
|---|---|---|
| 1 | 35.5 | 1 |
| 19 | 30(17.8%) | — |

*( ) is efficacy %

BIOLOGICAL EXPERIMENTAL EXAMPLE 4

Evaluation of Antiallodynic Activity on Complete Freund's Adjuvant (CFA)-Induced Inflammatory Pain Model Male, Sprague-Dawley rats (210-250 g, Nara Bio, Korea) were habituated for 1 week before surgery and allowed free access to food and water throughout the experimentation. Room temperature and humidity were maintained at 24±2 and 50±10%, respectively.

CFA-induced inflammatory pain was induced by the procedure of Nagakura et al. (2003) and Gregory P. et al. (2010) with minor modifications. CFA (sigma, USA) was injected in the right plantar with a 100 ul volume under gaseous anesthesia with isoflurane. Sham controls were injected with 100 ul of saline, and preparation of the vehicle controls were identical to the group treated with compound, except for administration of vehicles without indentical to the vihecle control group.

Tactile sensitivity (Mechanical allodynia) was evaluated using von Frey monofilaments before and after treatment, and animals were include in the study only if the withdrawal threshold value was less than 4 g. One week after CFA injection, CFA-infused animals, sham-operated animal, and vehicle-operated animals were tested for tactile sensitivity with von Frey monofilaments, with 3 trials for each animal. All Animals were placed in a stainless steel mashe chamber and habituated for 30 min in the test cage. The tactile sensitivity for ipsilateral hind paw was measured using the up-and-down method (Dixon, 1980) with seven von Frey monofilaments (0.4, 1, 2, 4, 6, 8, and 15 g) to 3 trials. The tactile sensitivity test was followed by Dixon's method (Dixon, 1980). The 50% paw withdrawal threshold for each paw was calculated using the following formula: [Xth]log=[vFr]log+ky where [vFr] is the force of the last von Frey used, k=0.2249 which is the average interval (in log units) between the von Frey monofilaments, and y is a value that depends upon the pattern of withdrawal responses (Dixon, 1980). If an animal did not respond to the highest von Frey hair (15 g), then the paw was assigned a value of 18.4 g.

Antiallodynic effect of compounds was evaluated at the dose of 50 mg/kg (n=4-6), intraperitoneally administrated in a volume of 5 ul/g bw in a vehicle of 30% (v/v) PEG or 20% (v/v) Tween 80. The test was performed peak time of efficacy (0.5 hr) after compound administration.

The relative values compared to the sham (% control) were calculated and shown in Table 5, which show an antiallodynic effect of Compound 1 on CFA-induced pain model in rats.

TABLE 5

Antiallodynic effect of CFA-induced pain model

| Example No. | Efficacy of 50 mg/kg(%) | Peak Time(h) |
|---|---|---|
| 1 | 74.9 | 0.5 |
| 2 | 23.2 | 0.5 |
| 3 | 22.9 | 0.5 |
| 5 | 30.0 | 0.5 |
| 6 | 26.8 | 0.5 |
| 7 | 28.6 | 0.5 |
| 9 | 27.5 | 0.5 |
| 10 | 35.2 | 0.5 |
| 12 | 38.5 | 0.5 |
| 13 | 43.1 | 0.5 |
| 18 | 50.2 | 0.5 |
| 19 | 51.6 | 0.5 |
| 20 | 40.2 | 0.5 |
| 21 | 28.9 | 0.5 |
| 22 | 35.7 | 0.5 |
| 27 | 37.8 | 0.5 |
| 28 | 42.1 | 0.5 |
| 29 | 30.3 | 0.5 |
| 30 | 28.4 | 0.5 |
| 36 | 72.2 | 0.5 |
| 51 | 40.1 | 0.5 |
| 52 | 34.7 | 0.5 |
| 55 | 34.4 | 0.5 |
| 56 | 43.2 | 0.5 |
| 63 | 53.1 | 0.5 |
| 64 | 43.7 | 0.5 |
| 72 | 21.4 | 0.5 |
| 76 | 59.2 | 0.5 |
| 78 | 62.3 | 0.5 |

BIOLOGICAL EXPERIMENTAL EXAMPLE 5

Hot-Plate Test

To examine the pain relief effect of the carbamate compounds, a hot-plate test was conducted in referring to Current Protocols in Neuroscience; Behavioral Neuroscience Unit 8.9.

ICR mice (male, 25-28 g; Orient Bio, Korea) were habituated before test (in test room) for 1 hour. Animals were fasted 2 hr before administration of compounds. Compounds were orally administered at the three dose, 10 ul/g, by bodyweight (n=4-6/group). All compounds were dissolved in a vehicle of 30% (v/v) PEG 400 or 20% (v/v) Tween 80. The control group was treated the vehicle without compounds.

0.25-2.0 hr after the administration of compounds, the mice were put on a hot plate pre-heated to 55±1 (Hu, X. et al, 2008), and then, the withdrawal latency time was measured (cut-off time: 30 sec) until the point when each mouse was taking a paw off from the plate, shaking, licking a paw or hind leg, or jumping from the plate. The relative values compared to the control (% control) were calculated and shown in Table 6.

TABLE 6

Effect of the compound of examples in hot-plate test

| Compound No. | ED50(mg/kg) | Peak Time(hr) |
|---|---|---|
| 1 | 101.1 | 1 |
| 19 | >100 | — |
| 52 | 118.9 | 0.5 |

BIOLOGICAL EXPERIMENTAL EXAMPLE 6

Tail-Flick Test

To examine the pain relief effect of the carbamate compounds, a tail-flick test was conducted, referring to Current Protocols in Neuroscience; Behavioral Neuroscience Unit 8.9.

ICR mice (male, 25-30g; Orient Bio, Korea) were habituated before test (in test room) for 1 hour. Animals were fasted 2 hr before administration of compounds. Each of Compound was orally administered at the 1-3 dose, 10 ul/g, by bodyweight (n=4-6/group). All compounds were dissolved in a vehicle of 30% (v/v) PEG 400 or 20% (v/v) Tween 80. The control group was treated the vehicle without compounds.

After the administration of compounds, the mice tail were put on a tail-flick analgesia meter. To avoid tissue damage, maximal exposure time to pain stimuli was restricted to 15 s. The withdrawal latency was measured to the time to the point when each mouse responded. The relative values compared to the control (% control) were calculated.

The relative values compared to the sham were calculated and shown in Table 7, which show effect of the compound of examples on tail-flick test in Mice.

TABLE 7

Effect of the compound of examples in tail-flick test

| Compound No. | Dose(mg/kg) |
|---|---|
| 1 | >150 |
| 19 | >200 |
| 52 | >200 |
| 54 | >200 |
| 64 | >200 |

BIOLOGICAL EXPERIMENTAL EXAMPLE 7

Measurement of Anti-Epilepsy Activity (MES-test)

In the MES test (Ref., G. Villetti et al. Neuropharmacology 40(2001) 866-878), an electrical stimulus (mice: 50 mA, 60 Hz, 0.2 sec, and rats: 150 mA, 60 Hz, 0.2 sec in the test animal) supplied by an 11A Shocker (IITC Life Science Company) was delivered through corneal electrodes. All mice or rats assigned to any electroshock at peak time were treated with each test compound sample which was dissolved in 20% tween 80 prepared by saline solvent applied orally before the test. If the test animal's stretching of its hind limb in a straight line wasn't observed in the MES test, these results indicated that the test samples had anti-epilepsy activity. Three doses of the test sample were administered orally to 9-18 animals (3-6 mice per dose) for evaluating the respective doses at which 50% of the animals were protected from seizure (ED50). The ED50 value (median effective dose) was calculated by Litchfield and Wicoxon log-probit method which is a dose-response relationship. Experimental animals, male ICR mice and male SD rats, were purchased from OrientBio, Samtako, or Nara Biotech, Korea, and housed in cages (4-5 mice or 3 rats per cage) for 4-5 days. The range of mice body weight was between 19 and 25 grams and range of rats body weight was between 100 and 130 grams. The obtained results are shown in following Table 8 and 9.

BIOLOGICAL EXPERIMENTAL EXAMPLE 8

Measurement of Anti-Epilepsy Activity (scPTZ)

In this experiment, each test compound sample was formulated as described in Biological Experimental Example 1, and administered intraperitoneally to the test animals (mice; ICR or Rat; SD); Experimental animals, male ICR mice and male SD rats, were purchased from OrientBio or Nara biotech, Korea, and housed 4-5 mice per a cage for 4-5 days. The range of mice body weight was used between 19 and 26 grams and range of rats body weight was used between 100 and 130 grams. After Peak time (0.5, 1, 2 and 4 hr) from the administration, PTZ (Pentylenetetrazol) was administered subcutaneously in the concentration capable of inducing 97% intermittent convulsions (mice: 100-110 mg/kg?bw, 10 μl/g, or rats: 90-110 mg/kg?bw, 2 μl/g). If clonic seizure was not observed for at least 30 minutes in the PTZ administered animal, it can be considered that the test compound has anti-epilepsy activity. The median effective dose (ED50) is determined using 6 animals per a concentration (total three different concentrations), and calculated by Litchfield and Wicoxon log-probit method which is a dose-response relationship. The obtained results are shown in following Table 8 and 9.

BIOLOGICAL EXPERIMENTAL EXAMPLE 9

Lithium-Pilocarpine Induced Epilepsy Test(LI-PILO Test) Prevention Test

Male Sprague-Dawley rats (purchased from Orient Bio Inc. Korea) of body weight 175 grams were used for these studies and 3 rats per cage were housed for 4-5 days. On the day prior to SE, rats received 127 mg/kg lithium chloride (Sigma, St. Louis, Mo., U.S.A.) intraperitoneally (i.p.). Approximately 18-20 h following this treatment, rats were given an i.p. injection of the concentration capable of inducing 97% intermittent convulsions pilocarpine(Sigma, 30-43 mg/kg). An i.p. injection of 2 mg/kg methyl-scopolamine (Sigma) was administered 30 min prior to pilocarpine to block the effects of the muscarinic agonist on peripheral cholinergic receptors. Test drugs were dissolved in 20% tween80 (Sigma).

The drugs were administered intraperitoneally (i.p.) in a volume of 2 µl/g body weight. Pharmacological effects of all of the test materials were evaluated to compare test groups (n=6) with a control group (n=6). Control group was administered vehicle only. The efficacy was measured 0.5, 1, 2, or 4 hours after the administration of the test material. The time point that the most animals were protected was defined as peak time and the ED50 was determined at peak time. The animals were then transferred to observation cages and observed continuously for 90 min Seizure was elicited in approximately 95% of the control group. Protection was defined as complete absence of seizure grade 3-5 (Racine scale; Racine, 1972) over the 90-min observation period. The effective dose of the compound necessary to protect 50% of the animals against seizures compared to controls (i.e., ED50) was determined by a curve fitting program (Excel 2007, Microsoft). The obtained results are shown in following Table 9.

TABLE 8

Pharmacological profile of compounds in mouse

| No. | MES test (po) ED50 (mg/kg) | Peak time (h) | PTZ test (ip) ED50 (mg/kg) | Peak time (h) |
|---|---|---|---|---|
| 1 | 12.1 | 0.5 | 12.5 | 0.5 |
| 2 | 41.0 | 0.5 | 26.6 | 0.5 |
| 3 | 27.3 | 1 | 25.2 | 0.5 |
| 4 | 80.6 | 4 | — | — |
| 5 | 100(100%) | 2 | 100(16.6%) | 2 |
| 6 | 100(33.3%) | 4 | — | — |
| 7 | 150(100%) | 2 | — | — |
| 8 | 100(100%) | 1 | — | — |
| 10 | 100(100%) | 1 | — | — |
| 12 | 100(100%) | 4 | — | — |
| 13 | 100(33.3%) | 1 | — | — |
| 14 | 100(100%) | 1 | — | — |
| 16 | 100(50%) | 0.5 | — | — |
| 18 | 45.8 | 1 | — | — |
| 19 | 22.4 | 1 | — | — |
| 20 | 31.4 | 0.5 | — | — |
| 21 | 100(33.3%) | 3 | — | — |
| 22 | 100(100%) | 2 | — | — |
| 23 | 100(33.3%) | 2 | — | — |
| 25 | 50(75%) | 1 | — | — |
| 27 | 200(100%) | 2, 4 | — | — |
| 28 | 100(100%) | 1, 2, 4 | — | — |
| 29 | 100(66.6%) | 1 | — | — |
| 30 | 400(33.3%) | 4 | — | — |
| 36 | 300(33.3%) | 2 | — | — |
| 37 | 300(33.3%) | 2 | — | — |
| 38 | 100(25%) | — | — | — |
| 40 | 100(100%) | 1, 2 | — | — |
| 51 | 37 | 0.5 | — | — |
| 52 | 24.3 | 0.5 | — | — |
| 54 | 26.7 | 0.5 | — | — |
| 55 | 51.9 | 2 | — | — |
| 56 | 45.6 | 0.5 | — | — |
| 59 | 56.5 | 2 | — | — |
| 62 | 53.1 | 1 | — | — |
| 63 | 51.9 | 0.5 | — | — |
| 64 | 48.4 | 2 | — | — |
| 68 | 61.2 | 1 | — | — |
| 69 | 100(33.3%) | 2 | — | — |
| 76 | 100(100%) | 1, 4 | — | — |
| 78 | 100(33.3%) | 4 | — | — |

*( ) is efficacy %

TABLE 9

Pharmacological profile of compounds in rats.

| No. | MES test (po) ED50 (mg/kg) | scPTZ test (ip) ED50 (mg/kg) | Lithium pilocarpine model (pre) ED50 (mg/kg) | Lithium pilocarpine model(inter) ED50 (mg/kg) |
|---|---|---|---|---|
| 1 | 5.9 (1 h) | 36.3 (0.5 h) | 22.0 (1 h) | 24.5 |
| 2 | 11.6 (0.5 h) | 39.7 (1 h) | 50 (1 h) | — |
| 3 | 12.1 (1 h) | — | — | — |
| 10 | 17.5 (4 h) | — | 100 (66.6%, 1, 2 h) | — |
| 18 | 18.8 (1 h) | 50 (33.3%, 0.5 h) | 100 (16.6%, 1, 2 h) | — |
| 19 | 4.6 (2 h) | 50 (4 h) | 50 (50%, 0.5 h) | — |
| 25 | 10 (33.3%, 1 h) | | 10 (33.3%, 1 h) | |
| 40 | | | 100 (66.6%, 0.5 h) | |
| 51 | 17.1 (4 h) | 100 (33.3%, 1 h) | | |
| 52 | 10.9 (2 h) | 100 (33.3%, 1, 2 h) | 63.0 (0.5 h) | |
| 54 | 10 (33.3%, 2 h) | | 100 (83.3%, 0.5 h) | |
| 55 | | | 100 (33.3%, 1 h) | |
| 62 | 24.5 (1 h) | | | |
| 63 | 19.1 (0.5 h) | 100 (83.3%, 0.5 h) | | |
| 64 | 17.8 (1 h) | 50 (50%, 0.5 h) | 100 (50%, 1 h) | |
| 68 | 14.4 (1 h) | | | |

*The number in ( ) indicates the efficacy & and peak time.

BIOLOGICAL EXPERIMENTAL EXAMPLE 10

The Neuroprotection SE Model

In the neuroprotection model, the seizure induction method was the same as in Lithium-pilocarpine induced epilepsy test(LI-PILO test) except that compound was administered by ip route at 30 min after seizure onset (Racine scale 4-5). For 14 days, the bodyweight and mortality were monitored.

On the 14th day, the rats were deeply anesthetized using Ketamine with Rumpun, 7:3 (v/v) i.p., and perfused transcardially with 150 ml of ice-cold 0.01 M phosphate buffer followed by 250 ml of freshly prepared ice-cold 4% paraformaldehyde (PFA) in 0.1 M phosphate buffer, pH 7.4. The brains were removed and postfixed in the same fixative for an additional 22-24 h at 4° C., and then transferred to 30% sucrose for cryoprotection until the samples were precipitated. Brains were frozen in methyl butane with dry ice and stored at −80° C. Serial coronal 25-mm slices were cut in a cryostat (Microtome HM 1850, Leica, Germany) and the sections were put onto slides, and air-dried before thionine staining. Every fifth section was selected for morphometric analysis. The stained hippocampus was imaged under a microscopic and enlarged 200- or 400-fold. The number of cells in the region of interest (dorsal hippocampus-CA1CA3, DG) was counted by observers blinded to the animals' treatment. The mean number was recorded. As a normal group, four naive rats were used. The obtained results are shown in following FIG. 1.

BIOLOGICAL EXPERIMENTAL EXAMPLE 11

The Chemical Induced Seizure Model (PIC)

Picrotoxin (PIC) were used to induce the behavioral seizures in the experiments. Male ICR mice (purchased from Orient Bio Inc. Korea) of body weight 19-26 g (mice) were used for these studies. The test materials were administered intraperitoneal (ip) route in a volume of 10 ul/g (mice) weight in rats or mice, respectively. Pharmacological effects of the test materials were evaluated to compared test groups (n=6) with a control group (n=6). Control group was administrated vehicle, only. The peak time was determined by administration of test material's random dose for 0.5, 1, 2, 4 hour. The time that the most protect was defined as a peak time and ED50 was determined by other dose administration at the peak time. Chemical (PIC) was dissolved in 0.9% saline and administered subcutaneously (s.c.) at its CD97 (convulsive dose 97%), the dose of Chemical (PIC) that produced clonic seizures in 97% into a loose fold of skin in the midline of the neck in a volume of 10 ul/g (mice) body weight. The animals were then transferred to observation cages and observed continuously for 45 min. Clonic seizure was elicited in approximately 97% of control group. Protection was defined as a complete absence of clonic seizure over the 45-min observation period. The effective dose of compound necessary to protect against generalized convulsive seizures to 50% of controls (i.e., ED50) was determined by log probit analysis using SPSS software program (SPSS Inc.). The obtained results are shown in following Table 1. (Reference; White H. S., J. H. Woodhead, K. S. Wilcox, J. P. Stables, H. J. Kupferberg, and H. H. Wolf. General Principles; Discovery and Preclinical Development of Antiepileptic Drugs. In: R. H. Levy, R. H. Mattson, B. S. Meldrum, and E. Perucca, eds. Antiepileptic Drugs, 5$^{th}$ Ed. Lippincott Williams & Wilkins, Philadelphia 2002: pp. 36-48.) The obtained results are shown in following Table 10.

TABLE 10

Pharmacological profile of compounds in the test animals (Mice)

| | PIC(ip) | |
|---|---|---|
| Compound No. | ED50(mg/kg) | Peak Time(h) |
| 1 | 23.7 | 2 |
| 2 | 50 (66.6%) | 1 |
| 19 | 120 (16.6%) | 2 |

*( ) is efficacy %

BIOLOGICAL EXPERIMENTAL EXAMPLE 12

The chemical Induced Seizure Model (BIC)

Male ICR mice (purchased from Orient Bio Inc. Korea) of body weight 19-26 g were used for these studies. The test materials were administered intraperitoneal route in a volume of 10 ul/g weight. Pharmacological effects of all the test materials were evaluated to compared test groups (n=6) with a control group (n=6). Control group was administrated vehicle, only. The peak time was determined by administration test material's random dose for 0.5 and 1 hour. The time that the most protect was defined peak time and ED50 was determined by other dose administration at peak time. BIC was dissolved in 0.9% saline and administered subcutaneously (s.c.) at its CD97 (convulsive dose 97%) the dose of BIC that produced clonic seizures in 97% into a loose fold of skin in the midline of the neck in a volume of 10 ul/g body weight. The animals were then transferred to observation cages and observed continuously for 30 min. Clonic seizure was elicited in approximately 95% of control group. Protection was defined as complete absence of a clonic seizure over the 30-min observation period. The time that the most protect was defined peak time and ED50 was determined by other dose administration at peak time. The effective dose of compound necessary to protect against seizures to 50% of controls (i.e., ED50) was determined by log probit analysis using Excel 2007 (Microsoft). The obtained results are shown in following Table 11.

TABLE 11

Pharmacological profile of compounds in the test animals (Mice)

| | BIC(ip) | |
|---|---|---|
| Compound No. | ED50(mg/kg) | Peak Time(h) |
| 1 | 28.9 | 1 |

BIOLOGICAL EXPERIMENTAL EXAMPLE 13

Corneal Kindling (CK) Rat Model

Male Sprague-Dawley rats (purchased from Orient Bio Inc. Korea) of body weight 85-100 g were used for these studies. The MES test using the electroshock seizure apparatus designed by Rodent Shocker Type221 (Hugo Sachs Elektronik, Germany). The kindled rat models were electrically stimulated (8 mA, 60 Hz, 2 s, corneal electrodes) twice daily for 21 days until stage 5 seizure scored by Racine's scale (Racine, 1972) were evoked. The kindled rats were fasted and adapted to test condition, for at least 1 hour before the administration of test material. The drugs were administered orally (p.o.) in a volume of 4 μl/g body weight. The corneally kindled rat model test is a model for generalized absence seizures or bipolar disorder and identifies the compound which prevents seizure or bipolar disorder spread. The shock level was set at 8 mA, 60 Hz and the duration was set at 2 s. A drop of 0.9% saline was placed in each eye, the electrodes were placed over the eyes, and the shock was administered immediately. Pharmacological effects of the test materials were evaluated to compare the test groups (n=6) with a control group (n=6). Control group was administrated vehicle, only. The peak time was determined by administration test material's random dose for 0.5, 1, 2, 4 hour. The time that the most protect was defined peak time and ED50 was determined by other dose administration at peak time. The effective dose of compound necessary to protect against seizures to 50% of controls (ED50) was determined by log probit analysis using SPSS software program (SPSS Inc.). The obtained results are shown in following Table 12. (Reference; Ewart A. William E. Bondinell (1991)). Anticonvuls ant profiles of the potent and orally active GABA uptake inhibitors SK&F 89976-A and SK&F 100330-A and four prototype antiepileptic drugs in mice and rats. Epilepsia, 32: 569-577./Hinko C. N., Crider A. M., Kliem M. A., Steinmiler C. L., Seo T. H., Bin Ho., Venkatarangan P., El-Assadi A. A., Chang H., Burns C. M., Tietz E. I., Andersen P. H., Klitgaard H. (1996). Anticonvulsant activity of novel derivatives of 2- and 3-pieridinecarboxylix acid in mice and rats. Neuropharmacology, 35: 1721-1735). The obtained results are shown in following Table 12.

TABLE 12

Pharmacological profile of compounds in the test animals (Rats)

| Compound No. | CK ED50(mg/kg) | Peak Time(h) |
|---|---|---|
| 1 | 7.5 | 2 |
| 59 | 21.4 | 4 |

BIOLOGICAL EXPERIMENTAL EXAMPLE 14

Multiple-Hit Rat Model of IS (Infantile Spasms)

This study was used male offspring of timed pregnant Sprague-Dawley rats (Nara biotech, Seoul, Korea) Animal preparation and surgical procedures were as described before (Scantlebury et al., 2010). At postnatal day 3 (PN3), doxorubicin (right intracerebroventricular) and lipopolysaccharide (right intraparietal) were infused stereotactically, under isoflurane anesthesia. At PN4, rats were separated for video monitoring as described (Scantlebury et al., 2010). The monitoring session consisted of 1 hour before injection and 5 hour after injection. The test materials were administered subcutaneously in a volume of 10 ul/g weight. Behavioral spasms were considered the sudden and synchronous high-amplitude movements of all limbs and body to a flexion or extension posture. Flexion or extension events that had asynchronous limb movements or appeared as an attempt of the pup to reposition were excluded to minimize false-positive events(Reference; Scantlebury M. H., Galanopoulou A. G., Chudomelova L., Raffo E., Betancourth D. and Moshe S. L. (2010). A model of symptomatic infantile spasm syndrome. Neurobiol. Dis. 37: 604-612./Ono T., Moshe S. L. and Galanopoulou A. G. (2011). Carisbamate acutely suppresses spasm in a rat model of symptomatic infantile spasms. Epilepsia 52: 1678-1684.) The test result was shown in FIG. 2.

Provided are non-human mammals treated with doxorubicin, lipopolysaccharide (LPS), and p-chlorophenylalanine (PCPA), where the mammal exhibits a symptom characteristic of infantile spasms. Also provided are methods of making a non-human mammal exhibit a symptom of infantile spasms. Additionally, methods are provided for screening a compound for the potential to attenuate a symptom of infantile spasms. The obtained results are shown in following FIG. 2.

The invention claimed is:
1. A compound having the formula 1 or a pharmaceutically acceptable salt thereof:

[Chemical formula 1]

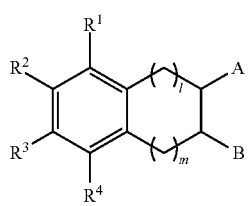

wherein,
$R^1$, $R^2$, $R^3$ and $R^4$ are each independently selected from the group consisting of hydrogen and halogen;
A and B are each independently selected from the group consisting of

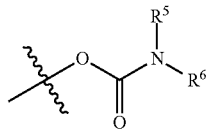

and $-OR^7$;
$R^5$ and $R^6$ are each independently selected from the group consisting of hydrogen, $C_1$-$C_{10}$alkyl, $C_3$-$C_8$cycloalkyl and $C_6$-$C_{10}$aryl;
$R^7$ is selected from hydrogen, $C_1$-$C_{10}$alkyl, $C_1$-$C_5$alkoxy$C_1$-$C_5$alkyl, $C_6$-$C_{10}$arylalkyloxy$C_1$-$C_5$alkyl, $C_1$-$C_5$alkoxy($C_1$-$C_5$alkoxy)$C_1$-$C_5$alkyl, $C_3$-$C_5$heterocyclyl, $C_1$-$C_5$alkylthio$C_1$-$C_5$alkyl; trialkyl silyl groups and trialkylaryl silyl groups (in trialkyl silyl groups and trialkylaryl silyl groups, each alkyl group is independently selected from the group consisting of linear, branched, or cyclic a $C_1$-$C_5$alkyl groups and each aryl group is independently selected from the group consisting of $C_6$-$C_{10}$aryl groups); and
l and m are each independently selected from an integer from 0 to 2.
wherein either of A or B is

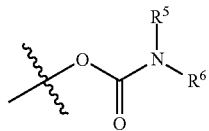

and both A and B cannot be OH at the same time, and when l is 0 and m is 1, or l is 1 and m is 0, one or more of $R^1$, $R^2$, $R^3$ and $R^4$ is halogen.

2. The compound or a pharmaceutically acceptable salt thereof according to claim 1, wherein $R^1$, $R^2$, $R^3$ and $R^4$ are each independently selected from the group consisting of hydrogen, F, Br, Cl and I; and if $R^1$, $R^2$, $R^3$ and $R^4$ are hydrogen, l+m is not 1.

3. The compound or a pharmaceutically acceptable salt thereof according to claim 1, wherein at least one of A and B is

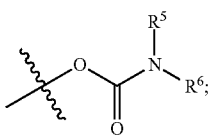

and $R^5$ and $R^6$ are each independently selected from the group consisting of hydrogen, $C_1$-$C_{10}$alkyl, $C_3$-$C_8$cycloalkyl and $C_6$-$C_{10}$aryl.

4. The compound or a pharmaceutically acceptable salt thereof according to claim 1, wherein $R^5$ and $R^6$ are each independently selected from the group consisting of hydrogen, methyl, ethyl, propyl, iso-propyl, t-butyl, cyclopropyl, cyclohexyl, bicycloheptanyl, phenyl and benzyl.

5. The compound or a pharmaceutically acceptable salt thereof according to claim 1, $R^7$ is selected from hydrogen, trimethyl silyl, triethyl silyl, triisopropyl silyl, t-butyl dimethyl silyl, trimethylsilylethoxymethyl (SEM), methoxymethyl (MOM), methoxyethoxymethyl (MEM), ethoxyethyl (EE), therahydropyranyl (THP) methylthiomethyl (MTM) and benzyloxymethyl (BOM).

6. The compound or a pharmaceutically acceptable salt thereof according to claim 1, wherein $R^5$ and $R^6$ are each independently selected from the group consisting of hydrogen, methyl, ethyl, propyl, iso-propyl and t-butyl; and
$R^7$ is selected from hydrogen, methyl, ethyl, propyl, iso-propyl, t-butyl and methoxymethyl (MOM); and
l and m are independently an integer from 0 to 2.

7. The compound or a pharmaceutically acceptable salt thereof according to claim 1, wherein at least one of A and B is

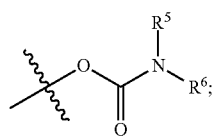

when l is an integer 0, m is an integer from 1 or 2; or when m is an integer 0, l is an integer from 1 or 2.

8. A compound according to claim 1, wherein the compound is selected from the group consisting of:
(1) (1S, 2R)-8-chloro-1-hydroxy-1,2,3,4-tetrahydronaphthalen-2-yl carbamate;
(2) (1R, 2S)-8-chloro-1-hydroxy-1,2,3,4-tetrahydronaphthalen-2-yl carbamate;
(3) racemate of (1S, 2R)-8-chloro-1-hydroxy-1,2,3,4-tetrahydronaphthalen-2-yl carbamate and (1R, 2S)-8-chloro-1-hydroxy-1,2,3,4-tetrahydronaphthalen-2-yl carbamate;
(4) (1R, 2R)-8-chloro-1-hydroxy-1,2,3,4-tetrahydronaphthalen-2-yl carbamate;
(5) (1S, 2S)-8-chloro-1-hydroxy-1,2,3,4-tetrahydronaphthalen-2-yl carbamate;
(6) (1S, 2R)-7-chloro-1-hydroxy-1,2,3,4-tetrahydronaphthalen-2-yl carbamate;
(7) (1R, R)-7-chloro-1-hydroxy-1,2,3,4-tetrahydronaphthalen-2-yl carbamate;
(8) (1S, 2R)-6-chloro-1-hydroxy-1,2,3,4-tetrahydronaphthalen-2-yl carbamate;
(9) (1R, 2S)-6-chloro-1-hydroxy-1,2,3,4-tetrahydronaphthalen-2-yl carbamate;
(10) (1S, 2R)-8-fluoro-1-hydroxy-1,2,3,4-tetrahydronaphthalen-2-yl carbamate;
(11) (1R, 2S)-8-fluoro-1-hydroxy-1,2,3,4-tetrahydronaphthalen-2-yl carbamate;
(12) (1S, 2R)-1-hydroxy-8-iodo-1,2,3,4-tetrahydronaphthalen-2-yl carbamate;
(13) (1R, 2S)-1-hydroxy-8-iodo-1,2,3,4-tetrahydronaphthalen-2-yl carbamate;
(14) (1S, 2R)-1-hydroxy-1,2,3,4-tetrahydronaphthalen-2-yl carbamate;
(15) (1R, 2S)-1-hydroxy-1,2,3,4-tetrahydronaphthalen-2-yl carbamate;
(16) (1S, 2R)-2-hydroxy-1,2,3,4-tetrahydronaphthalen-1-yl carbamate;
(17) (1R, 2S)-2-hydroxy-1,2,3,4-tetrahydronaphthalen-1-yl carbamate;
(18) (1S, 2R)-8-chloro-2-hydroxy-1,2,3,4-tetrahydronaphthalen-1-yl carbamate;
(19) (1R, 2S)-8-chloro-2-hydroxy-1,2,3,4-tetrahydronaphthalen-1-yl carbamate;
(20) racemate of (1S, 2R)-8-chloro-2-hydroxy-1,2,3,4-tetrahydronaphthalen-1-yl carbamate and (1R, 2S)-8-chloro-2-hydroxy-1,2,3,4-tetrahydronaphthalen-1-yl carbamate;
(21) (1S, 2R)-7-chloro-2-hydroxy-1,2,3,4-tetrahydronaphthalen-1-yl carbamate;
(22) (1R, 2S)-7-chloro-2-hydroxy-1,2,3,4-tetrahydronaphthalen-1-yl carbamate;
(23) (1S, 2R)-6-chloro-2-hydroxy-1,2,3,4-tetrahydronaphthalen-1-yl carbamate;
(24) (1R, 2S)-6-chloro-2-hydroxy-1,2,3,4-tetrahydronaphthalen-1-yl carbamate;
(25) (1S, 2R)-8-fluoro-2-hydroxy-1,2,3,4-tetrahydronaphthalen-1-yl carbamate;
(26) (1R, 2S)-8-fluoro-2-hydroxy-1,2,3,4-tetrahydronaphthalen-1-yl carbamate;
(27) (1S, 2R)-2-hydroxy-8-iodo-1,2,3,4-tetrahydronaphthalen-1-yl carbamate;
(28) (1R, 2S)-2-hydroxy-8-iodo-1,2,3,4-tetrahydronaphthalen-1-yl carbamate;
(29) (1S, 2R)-8-chloro-1,2,3,4-tetrahydronaphthalen-1,2-diyl di-carbamate;
(30) (1R, 2S)-8-chloro-1,2,3,4-tetrahydronaphthalen-1,2-diyl di-carbamate;
(31) (1R, 2R)-8-chloro-1,2,3,4-tetrahydronaphthalen-1,2-diyl di-carbamate;
(32) (1S, 2R)-7-chloro-1,2,3,4-tetrahydronaphthalen-1,2-diyl di-carbamate;
(33) (1R, 2S)-6-chloro-1,2,3,4-tetrahydronaphthalen-1,2-diyl di-carbamate;
(34) (1S, 2R)-8-fluoro-1,2,3,4-tetrahydronaphthalen-1,2-diyl di-carbamate;
(35) (1R, 2S)-8-fluoro-1,2,3,4-tetrahydronaphthalen-1,2-diyl di-carbamate;
(36) (1S, 2R)-8-iodo-1,2,3,4-tetrahydronaphthalen-1,2-diyldicarbamate;
(37) (1R, 2S)-8-iodo-1,2,3,4-tetrahydronaphthalen-1,2-diyldicarbamate;
(38) (1S, 2R)-1,2,3,4-tetrahydronaphthalen-1,2-diyl dicarbamate;
(39) (1R, 2S)-1,2,3,4-tetrahydronaphthalen-1,2-diyl dicarbamate;
(40) (1S, 2R)-8-chloro-1-(methoxymethoxy)-1,2,3,4-tetrahydronaphthalen-2-yl carbamate;
(41) (1R, 2S)-8-chloro-1-(methoxymethoxy)-1,2,3,4-tetrahydronaphthalen-2-yl carbamate;
(42) (1R, 2R)-8-chloro-1-(methoxymethoxy)-1,2,3,4-tetrahydronaphthalen-2-yl carbamate;
(43) (1S, 2R)-8-fluoro-1-(methoxymethoxy)-1,2,3,4-tetrahydronaphthalen-2-yl carbamate;
(44) (1R, 2S)-8-fluoro-1-(methoxymethoxy)-1,2,3,4-tetrahydronaphthalen-2-yl carbamate;
(45) (1S, 2R)-8-chloro-2-(methoxymethoxy)-1,2,3,4-tetrahydronaphthalen-1-yl carbamate;
(46) (1R, 2S)-8-chloro-2-(methoxymethoxy)-1,2,3,4-tetrahydronaphthalen-1-yl carbamate;
(47) (1S, 2R)-8-fluoro-2-(methoxymethoxy)-1,2,3,4-tetrahydronaphthalen-1-yl carbamate;
(48) (1R,2S)-8-fluoro-2-(methoxymethoxy)-1,2,3,4-tetrahydronaphthalen-1-yl carbamate;
(49) (1S, 2R)-8-iodo-2-(methoxymethoxy)-1,2,3,4-tetrahydronaphthalen-1-yl carbamate;
(50) (1R, 2S)-8-iodo-2-(methoxymethoxy)-1,2,3,4-tetrahydronaphthalen-1-yl carbamate;
(51) (1S, 2R)-7-chloro-1-hydroxy-2,3-dihydro-1H-inden-2-yl carbamate;

(52) (1R, 2S)-7-chloro-1-hydroxy-2,3-dihydro-1H-inden-2-yl carbamate;
(53) (1R, 2R)-7-chloro-1-hydroxy-2,3-dihydro-1H-inden-2-yl carbamate;
(54) (1S, 2S)-7-chloro-1-hydroxy-2,3-dihydro-1H-inden-2-yl carbamate;
(55) (1S, 2R)-7-fluoro-1-hydroxy-2,3-dihydro-1H-inden-2-yl carbamate;
(56) (1R, 2S)-7-fluoro-1-hydroxy-2,3-dihydro-1H-inden-2-yl carbamate;
(57) (1S, 2R)-6-chloro-1-hydroxy-2,3-dihydro-1H-inden-2-yl carbamate;
(58) (1R, 2S)-6-chloro-1-hydroxy-2,3-dihydro-1H-inden-2-yl carbamate;
(59) (1S, 2R)-5,7-dichloro-1-hydroxy-2,3-dihydro-1H-inden-2-yl carbamate;
(60) (1R, 2S)-5,7-dichloro-1-hydroxy-2,3-dihydro-1H-inden-2-yl carbamate;
(61) (1R, 2S)-4-chloro-2-hydroxy-2,3-dihydro-1H-inden-1-yl carbamate;
(62) (1S, 2R)-4-chloro-2-hydroxy-2,3-dihydro-1H-inden-1-yl carbamate;
(63) (1S, 2R)-7-chloro-2-hydroxy-2,3-dihydro-1H-inden-1-yl carbamate;
(64) (1R, 2S)-7-chloro-2-hydroxy-2,3-dihydro-1H-inden-1-yl carbamate;
(65) (1S, 2R)-5,7-dichloro-2-hydroxy-2,3-dihydro-1H-inden-1-yl carbamate;
(66) (1R, 2S)-5,7-dichloro-2-hydroxy-2,3-dihydro-1H-inden-1-yl carbamate;
(67) (1R, 2S)-4-chloro-1-hydroxy-2,3-dihydro-1H-inden-2-yl carbamate;
(68) (1S, 2R)-4-chloro-1-hydroxy-2,3-dihydro-1H-inden-2-yl carbamate;
(69) (1S, 2R)-7-fluoro-2-hydroxy-2,3-dihydro-1H-inden-1-yl carbamate;
(70) (1R, 2S)-7-chloro-2-hydroxy-2,3-dihydro-1H-inden-1-yl carbamate;
(71) (1S, 2R)-7-chloro-1-(methoxymethoxy)-2,3-dihydro-1H-inden-2-yl carbamate;
(72) (1R, 2S)-7-chloro-1-(methoxymethoxy)-2,3-dihydro-1H-inden-2-yl carbamate;
(73) (1S, 2R)-7-fluoro-1-(methoxymethoxy)-2,3-dihydro-1H-inden-2-yl carbamate;
(74) (1R, 2S)-7-fluoro-1-(methoxymethoxy)-2,3-dihydro-1H-inden-2-yl carbamate;
(75) (1S, 2R)-7-chloro-2-(methoxymethoxy)-2,3-dihydro-1H-inden-1-yl carbamate;
(76) (1R, 2S)-7-chloro-2-(methoxymethoxy)-2,3-dihydro-1H-inden-1-yl carbamate;
(77) (1S, 2R)-7-chloro-2,3-dihydro-1H-inden-1,2-diyldicarbamate;
(78) (1R, 2S)-7-chloro-2,3-dihydro-1H-inden-1,2-diyldicarbamate;
(79) (1R, 2S)-4-chloro-2,3-dihydro-1H-inden-1,2-diyldicarbamate;
(80) (1S, 2R)-4-chloro-2,3-dihydro-1H-inden-1,2-diyldicarbamate;
(81) (1S, 2R)-6-chloro-2,3-dihydro-1H-inden-1,2-diyldicarbamate;
(82) (1R, 2S)-6-chloro-2,3-dihydro-1H-inden-1,2-diyldicarbamate;
(83) (1S, 2R)-5,7-dichloro-2,3-dihydro-1H-inden-1,2-diyl dicarbamate;
(84) (1R, 2S)-5,7-dichloro-2,3-dihydro-1H-inden-1,2-diyl dicarbamate;
(85) (1S, 2R)-7-fluoro-2,3-dihydro-1H-inden-1,2-diyl dicarbamate;
(86) (1R, 2S)-7-fluoro-2,3-dihydro-1H-inden-1,2-diyl dicarbamate;
(87) (1S,2R)-8-chloro-1-methoxy-1,2,3,4-tetrahydronaphthalen-2-yl carbamate;
(88) (1S,2R)-8-chloro-1-methoxy-1,2,3,4-tetrahydronaphthalen-2-yl isopropylcarbamate;
(89) (1S,2R)-8-chloro-1-(methoxymethoxy)-1,2,3,4-tetrahydronaphthalen-2-yl isopropylcarbamate;
(90) (1S,2R)-8-chloro-1-hydroxy-1,2,3,4-tetrahydronaphthalen-2-yl isopropylcarbamate;
(91) (1S,2R)-8-chloro-2-hydroxy-1,2,3,4-tetrahydronaphthalen-1-yl isopropylcarbamate;
(92) (1S,2R)-8-chloro-2-methoxy-1,2,3,4-tetrahydronaphthalen-1-yl isopropylcarbamate; and
(93) (1S,2R)-8-chloro-2-(methoxymethoxy)-1,2,3,4-tetrahydronaphthalen-1-yl isopropylcarbamate.

9. A method of preventing or treating CNS disorders and/or pain, comprising administering a therapeutically effective amount of the compound having the formula 1 according to claim 1, or a pharmaceutically acceptable salt thereof as an active ingredient, to a subject in need of treatment:
wherein the CNS disorders are selected from epilepsy or epilepsy-related syndrome, pediatric epilepsy or pediatric epilepsy-related syndrome, memory loss related disease, psychiatric disorder, movement disorder, neurodegenerative disease, Autism spectrum disease, prion disease and stroke; and wherein the memory loss related disease is Alzheimer's disease; the movement disorder is selected from the group consisting of Tremors, Essential tremor, Parkinsonian tremor, and Parkinson's disease; and the neurodegenerative disease is selected from the group consisting of Huntington's disease, Pick's disease, Shy-Drager syndrome, Spinocerebellar ataxia, Tay-Sach's disease, and Sandhoff disease.

10. The method according to claim 9, wherein the pain is one or more selected from nociceptive pain, psychogenic pain, inflammatory pain, pathological pain, neuropathic pain, cancer pain, postoperative pain, trigeminal neuralgia pain, idiopathic pain, diabetic neuropathic pain, and migraine.

11. The method according to claim 9, wherein the epilepsy is an intractable epilepsy, localization-related epilepsy, cortical epilepsy, frontal lobe epilepsy, parietal lobe epilepsy, occipital lobe epilepsy, temporal lobe epilepsy, generalized epilepsy and syndromes thereof.

12. The method according to claim 9, wherein the epilepsy-related syndrome is an epileptic seizure, an intractable localization-related epilepsy, an intractable secondary generalized seizure, an intractable complex partial seizure or an intractable status epilepticus.

13. The method according to claim 9, wherein the pediatric epilepsy or pediatric epilepsy-related syndrome is selected from the group consisting of Benign Myoclonic Epilepsy (BME), Severe Myoclonic Epilepsy of Infancy Borderland (SMEB), Severe Infantile Multifocal Epilepsy (SIMFE), and Intractable Childhood Epilepsy with Generalized Tonic Clonic Seizures (ICE-GTC), Dravet syndrome (Ds), Severe Myoclonic Epilepsy of Infancy (SMEI), Benign neonatal convulsions, Benign neonatal familial convulsions, Miscellaneous neonatal seizures, Febrile seizures, Early infantile epileptic encephalopathy, Early myoclonic encephalopathy, Infantile spasm, West syndromes, Severe myoclonic epilepsy of infancy, Benign myoclonic epilepsy of infancy, Benign partial epilepsy of infancy, Benign infantile familial convulsion, Symptomatic/cryptogenic partial epilepsies, Epilepsy with myoclonic absences, Lennox-Gastaut syndrome, Epilepsy with myoclonic-astatic seizures (Doose syndrome), Acquired epileptic aphasia (Landaw-Kleffner syndrome), Epilepsy with continuous spikewave during low-wave sleep, Epilepsy with gastric seizures and hypothalamic hamartoma, Symptomatic/cryptogenic partial epilepsies and Childhood absence epilepsy.

14. The method according to claim 9, wherein the compound is in the form of racemate, enantiomer, diastereomer, a mixture of enantiomer, or a mixture of diastereomer.

15. The pharmaceutical composition comprising a therapeutically effective amount of the compound having the formula 1 according to claim 1, or a pharmaceutically acceptable salt thereof as an active ingredient.

16. The pharmaceutical composition according to claim 15 for treating CNS disorders and/or pain, wherein the CNS disorders are selected from epilepsy or epilepsy-related syndrome, pediatric epilepsy or pediatric epilepsy-related syndrome, memory loss related disease, psychiatric disorder, movement disorder, neurodegenerative disease, Autism spectrum disease, prion disease and stroke; wherein the memory loss related disease is Alzheimer's disease; the movement disorder is selected from the group consisting of Tremors, Essential tremor, Parkinsonian tremor, and Parkinson's disease; and the neurodegenerative disease is selcted from the group consisting of Huntington's disease, Pick's disease, Shy-Drager syndrome, Spinocerebellar ataxia, Tay-Sach's disease, and Sandhoff disease.

* * * * *